United States Patent
Scott et al.

(10) Patent No.: US 9,782,160 B2
(45) Date of Patent: *Oct. 10, 2017

(54) SYSTEM FOR INTRA-ABDOMINALLY MOVING AN ORGAN

(71) Applicant: Freehold Surgical, Inc., New Hope, PA (US)

(72) Inventors: J. Stephen Scott, Wentzville, MO (US); Jeffrey Smith, New Hope, PA (US)

(73) Assignee: Freehold Surgical, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/604,366

(22) Filed: May 24, 2017

(65) Prior Publication Data

US 2017/0252029 A1 Sep. 7, 2017

Related U.S. Application Data

(63) Continuation of application No. 15/298,144, filed on Oct. 19, 2016, now Pat. No. 9,687,218, which is a (Continued)

(51) Int. Cl.
*A61B 17/02* (2006.01)
*A61B 17/04* (2006.01)
(Continued)

(52) U.S. Cl.
CPC ...... *A61B 17/0218* (2013.01); *A61B 17/0401* (2013.01); *A61B 17/0466* (2013.01);
(Continued)

(58) Field of Classification Search
CPC ............ A61B 17/0218; A61B 17/0643; A61B 17/0487; A61B 2017/0225; A61B 2017/0496; A61B 2017/0464
See application file for complete search history.

(56) References Cited

U.S. PATENT DOCUMENTS 302,509 A 7/1884 Mauthner
3,695,271 A 10/1972 Chodorow
(Continued)

FOREIGN PATENT DOCUMENTS

EP 1568326 8/2005
JP 2008142516 6/2008
(Continued)

OTHER PUBLICATIONS

Sakaguchi, et. al., New technique for the retraction of the liver in laparoscopic gastrectomy, 22 Surgical Endoscopy 2532 (2008).
(Continued)

*Primary Examiner* — Christine H Matthews
*Assistant Examiner* — Kaylee Wilson
(74) *Attorney, Agent, or Firm* — K. David Crockett, Esq.; Crockett & Crockett, PC

(57) ABSTRACT

A surgical tissue connector system for moving a first internal body tissue to a position away from a second internal body tissue and then holding the first internal body tissue in the position. Tissue connectors are secured to cords such that the length of cord between the tissue connectors can be easily adjusted in a laparoscopic work space.

17 Claims, 49 Drawing Sheets

Related U.S. Application Data continuation of application No. 14/240,928, filed as application No. PCT/US2011/001494 on Aug. 25, 2011, now abandoned.

(51) Int. Cl.
  *A61B 17/064* (2006.01)
  *A61B 17/062* (2006.01)
  *A61B 17/08* (2006.01)
  *A61B 17/06* (2006.01)

(52) U.S. Cl.
  CPC ...... *A61B 17/0482* (2013.01); *A61B 17/0487* (2013.01); *A61B 17/062* (2013.01); *A61B 17/0643* (2013.01); *A61B 17/083* (2013.01); *A61B 2017/0225* (2013.01); *A61B 2017/0417* (2013.01); *A61B 2017/0448* (2013.01); *A61B 2017/0461* (2013.01); *A61B 2017/0464* (2013.01); *A61B 2017/0496* (2013.01); *A61B 2017/0647* (2013.01); *A61B 2017/06057* (2013.01); *A61B 2017/06071* (2013.01)

(56) References Cited

U.S. PATENT DOCUMENTS

| | | | |
|---|---|---|---|
| 5,193,955 | A | 3/1993 | Chou |
| 5,362,294 | A | 11/1994 | Seitzinger |
| 5,383,904 | A | 1/1995 | Totakura et al. |
| 5,415,666 | A | 5/1995 | Gourlay et al. |
| 5,582,577 | A | 12/1996 | Lund et al. |
| 6,042,534 | A | 3/2000 | Gellman et al. |
| 8,251,889 | B2 | 8/2012 | Scott |
| 8,888,679 | B2 | 11/2014 | Scott |
| 2001/0041916 | A1 | 11/2001 | Bonutti |
| 2004/0225305 | A1 | 11/2004 | Ewers et al. |
| 2005/0043580 | A1 | 2/2005 | Watschke et al. |
| 2005/0203344 | A1 | 9/2005 | Orban et al. |
| 2005/0216040 | A1 | 9/2005 | Gertner et al. |
| 2005/0250980 | A1 | 11/2005 | Swanstrom et al. |
| 2006/0106423 | A1 | 5/2006 | Weisel et al. |
| 2007/0250116 | A1 | 10/2007 | Raju |
| 2008/0021485 | A1 | 1/2008 | Catanese et al. |
| 2009/0018552 | A1 | 1/2009 | Lam et al. |
| 2009/0137862 | A1 | 5/2009 | Evans et al. |
| 2010/0081864 | A1 | 4/2010 | Hess et al. |
| 2010/0256678 | A1 | 10/2010 | Ducharme |
| 2010/0261950 | A1 | 10/2010 | Lund et al. |
| 2010/0292540 | A1 | 11/2010 | Hess et al. |
| 2010/0292732 | A1 | 11/2010 | Hirotsuka et al. |
| 2011/0112357 | A1 | 5/2011 | Chapman et al. |
| 2011/0172682 | A1 | 7/2011 | Brady et al. |
| 2012/0078298 | A1 | 3/2012 | Sklar |
| 2012/0116153 | A1 | 5/2012 | Scott |

FOREIGN PATENT DOCUMENTS

| | | |
|---|---|---|
| WO | WO9807374 | 2/1998 |
| WO | WO0230293 | 4/2002 |
| WO | WO03096907 | 11/2003 |
| WO | WO2007149593 | 12/2007 |
| WO | WO2009064866 | 5/2009 |
| WO | WO2009140298 | 11/2009 |
| WO | WO2010099327 | 9/2010 |
| WO | WO2013028145 | 2/2013 |

OTHER PUBLICATIONS

European Search Report dated Apr. 26, 2016 from European Application 13809773.8.

Patent Examination Report dated Apr. 15, 2016 from Australian Patent Application No. 2011375467.

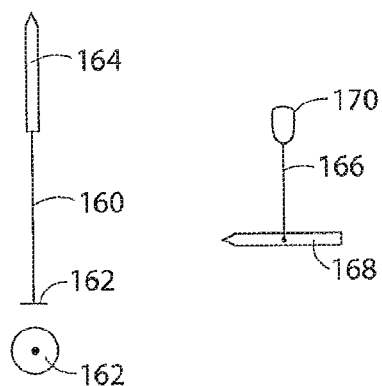
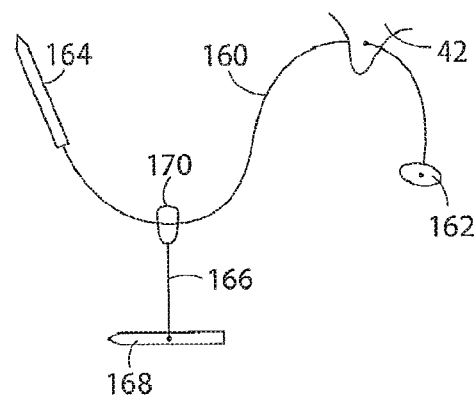
FIG. 20A  FIG. 20B
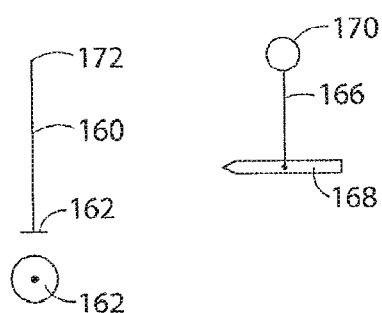
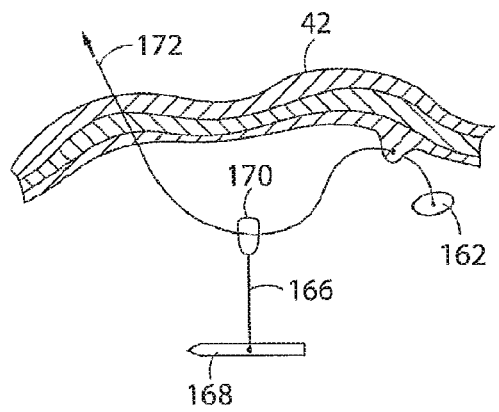
FIG. 21A  FIG. 21B
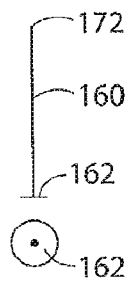
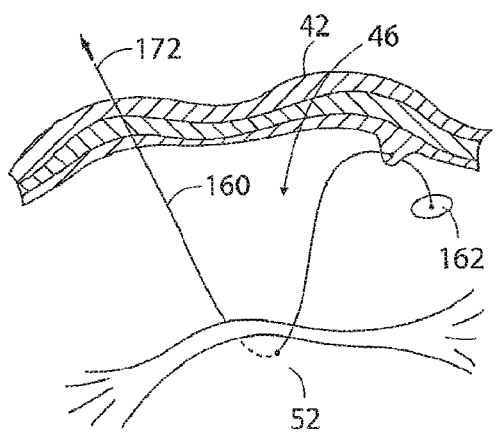
FIG. 22A  FIG. 22B

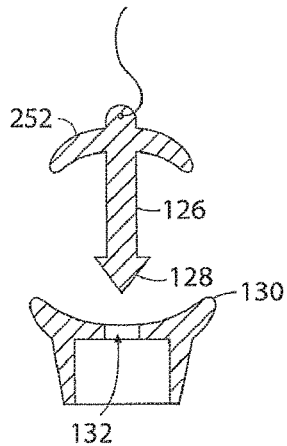
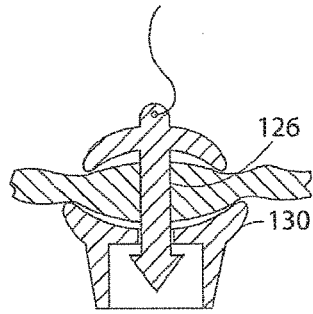
FIG. 44A
FIG. 44B
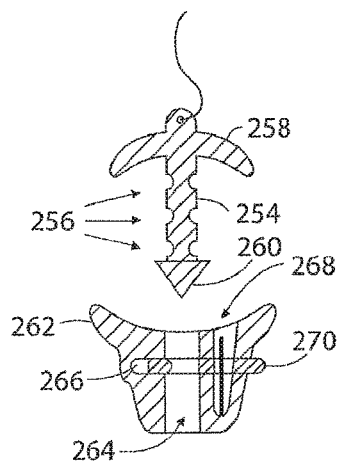
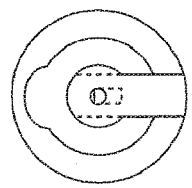
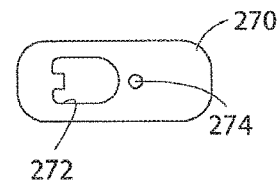
FIG. 45A
FIG. 45B
FIG. 45C
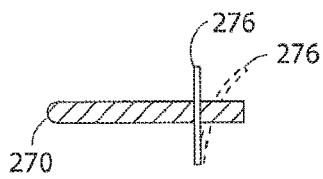
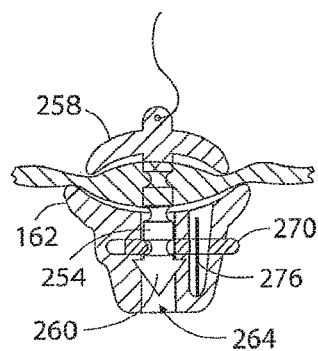
FIG. 45D
FIG. 45E

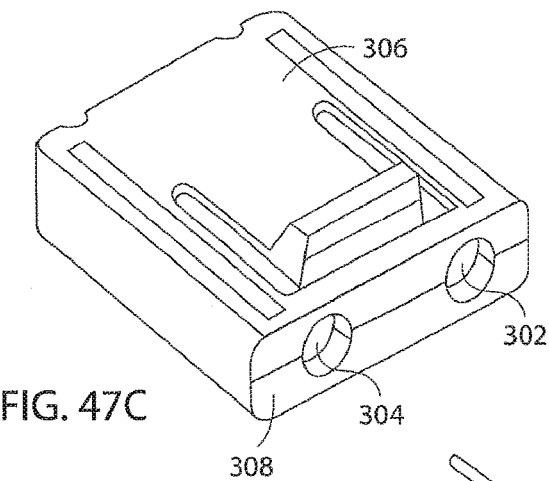
FIG. 47C
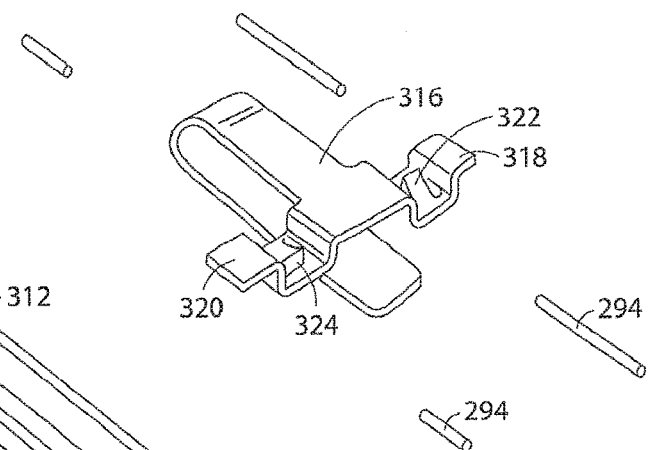
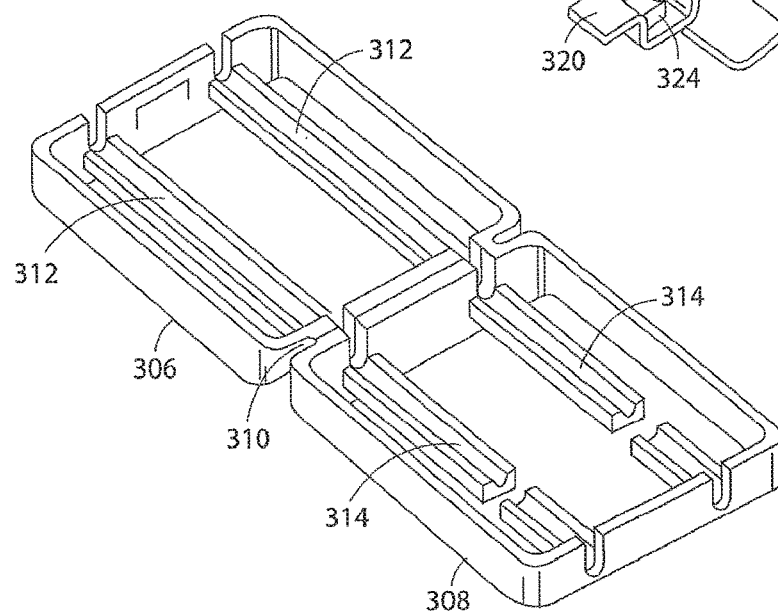
FIG. 47D

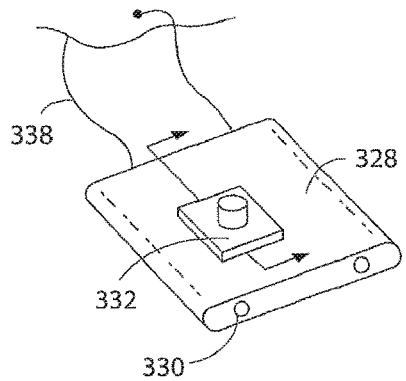
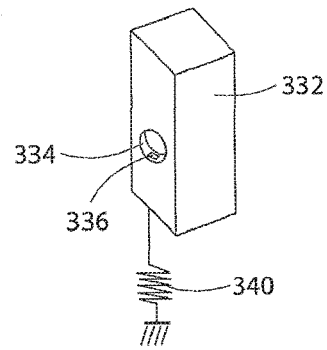
FIG. 48A  FIG. 48B
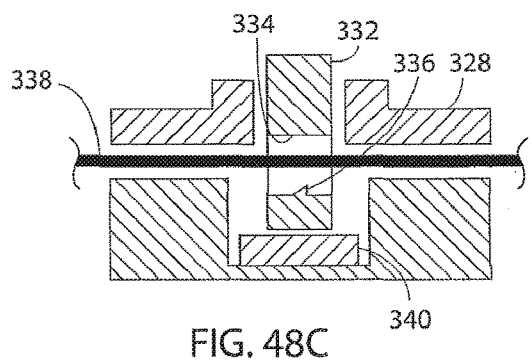
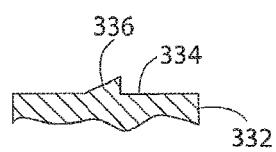
FIG. 48C  FIG. 48D
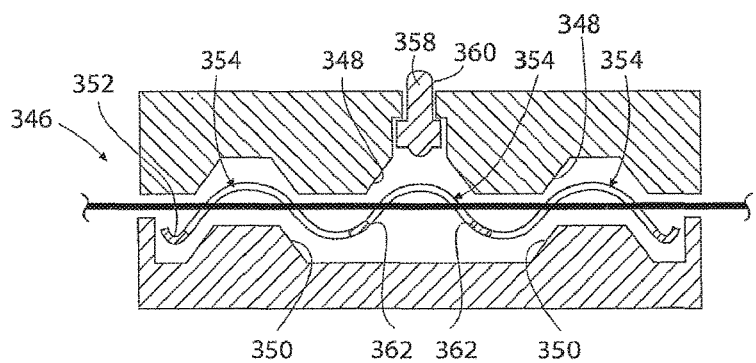
FIG. 49A
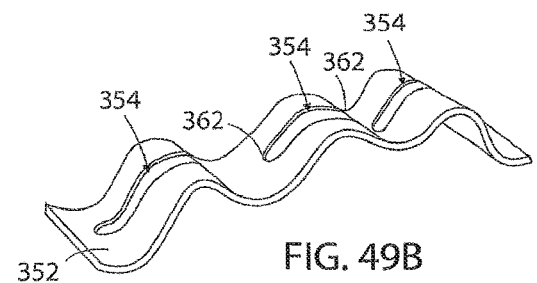
FIG. 49B

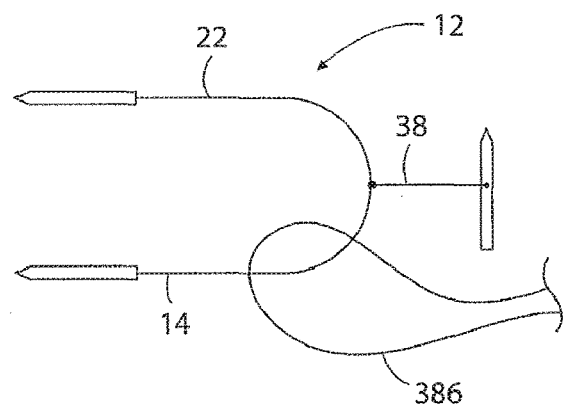
FIG. 51A
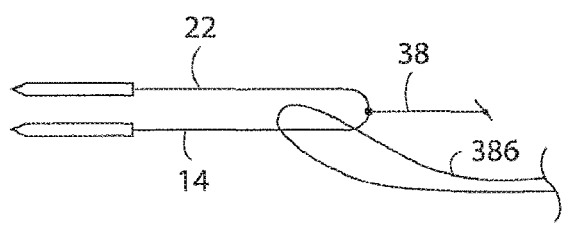
FIG. 51B
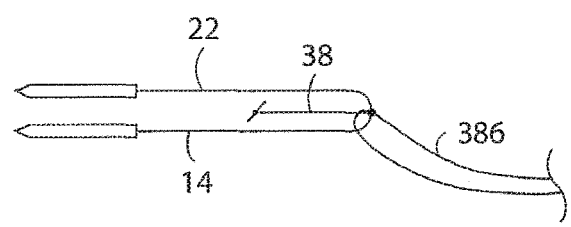
FIG. 51C
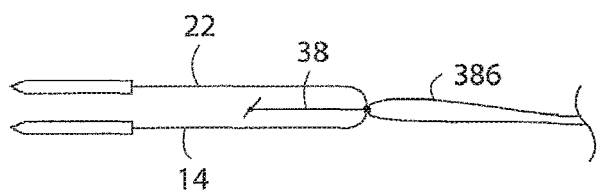 
FIG. 51D
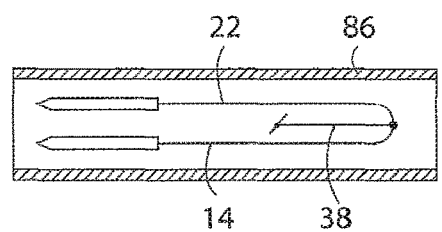
FIG. 51E

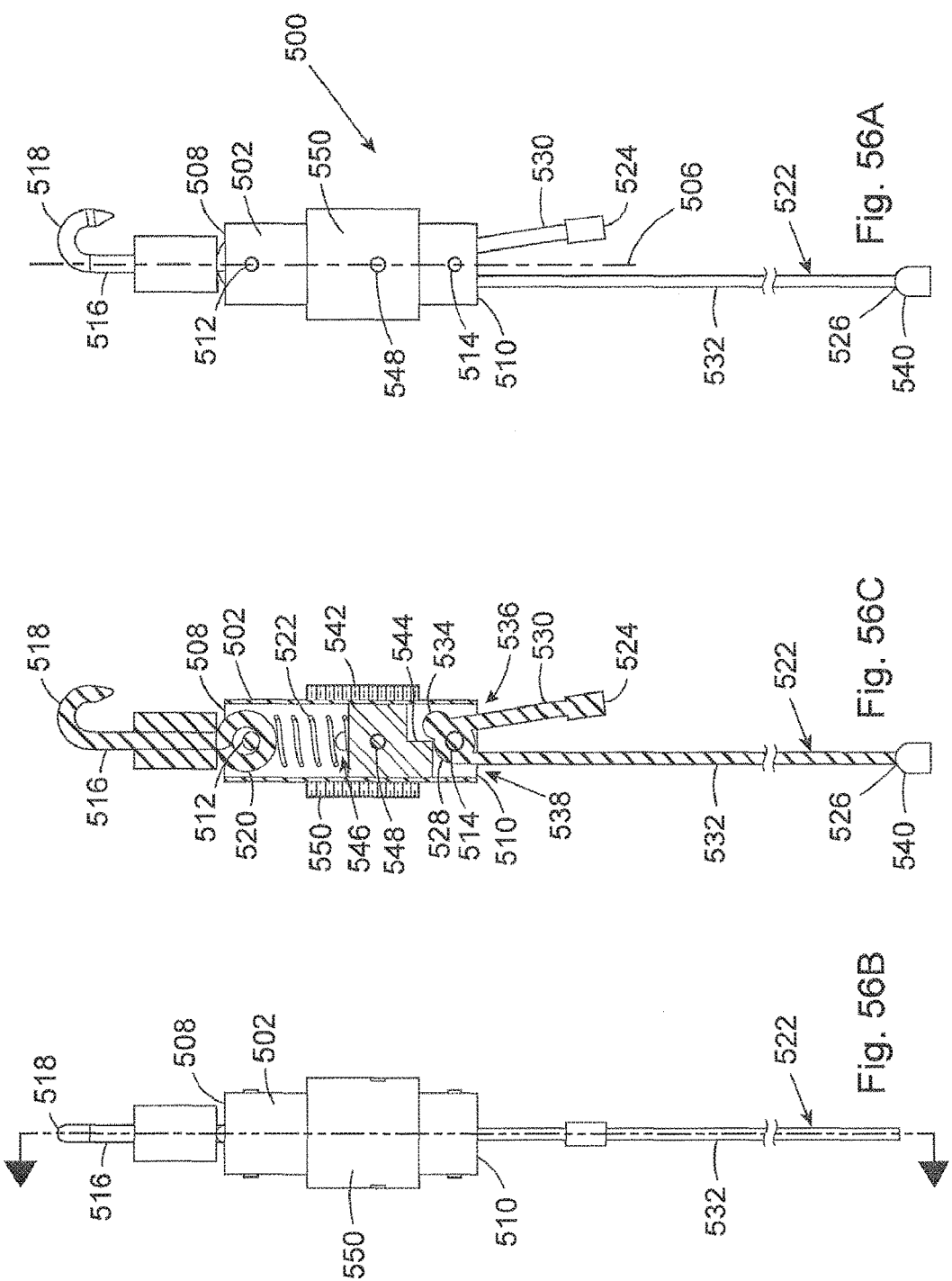

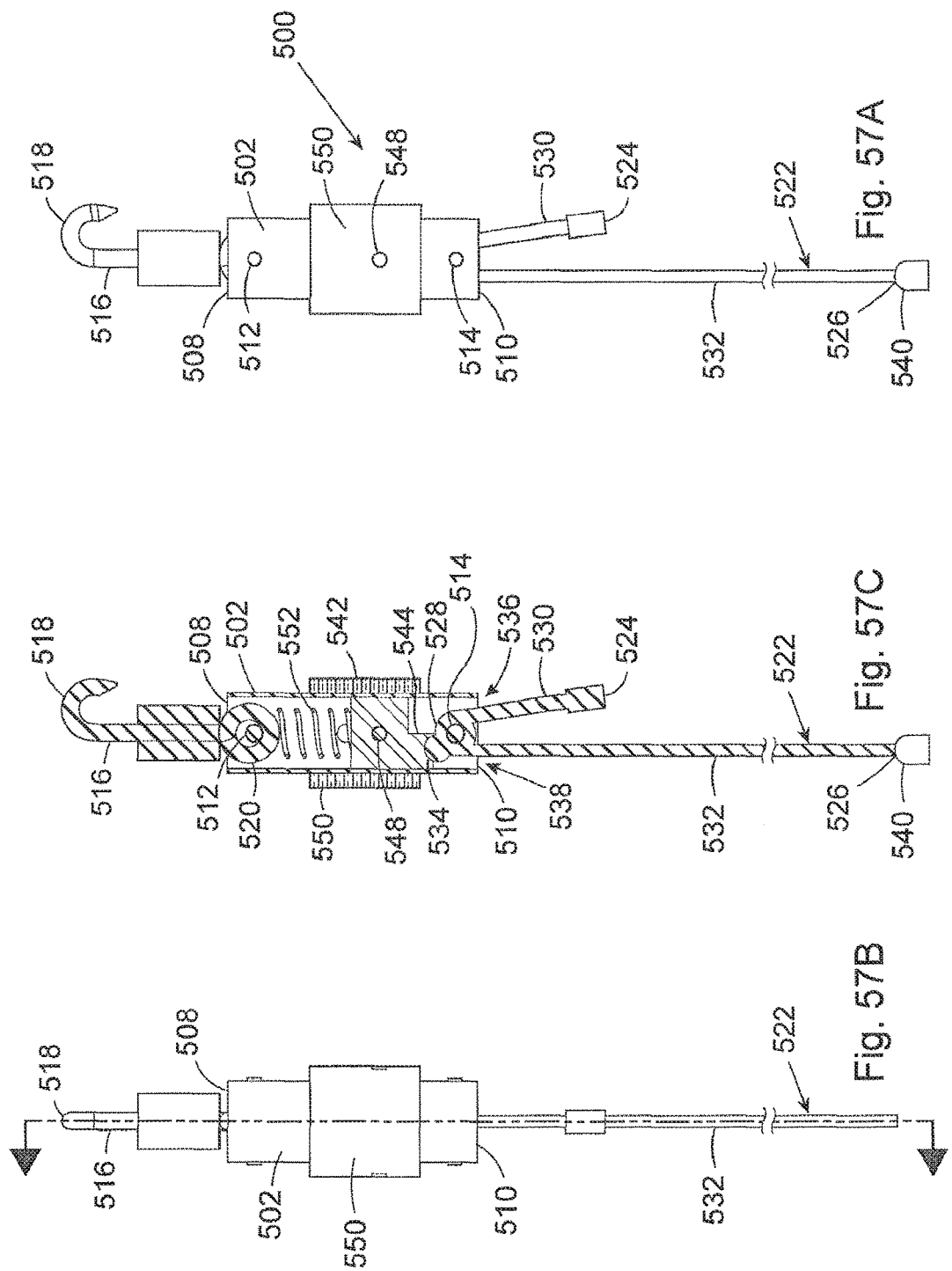

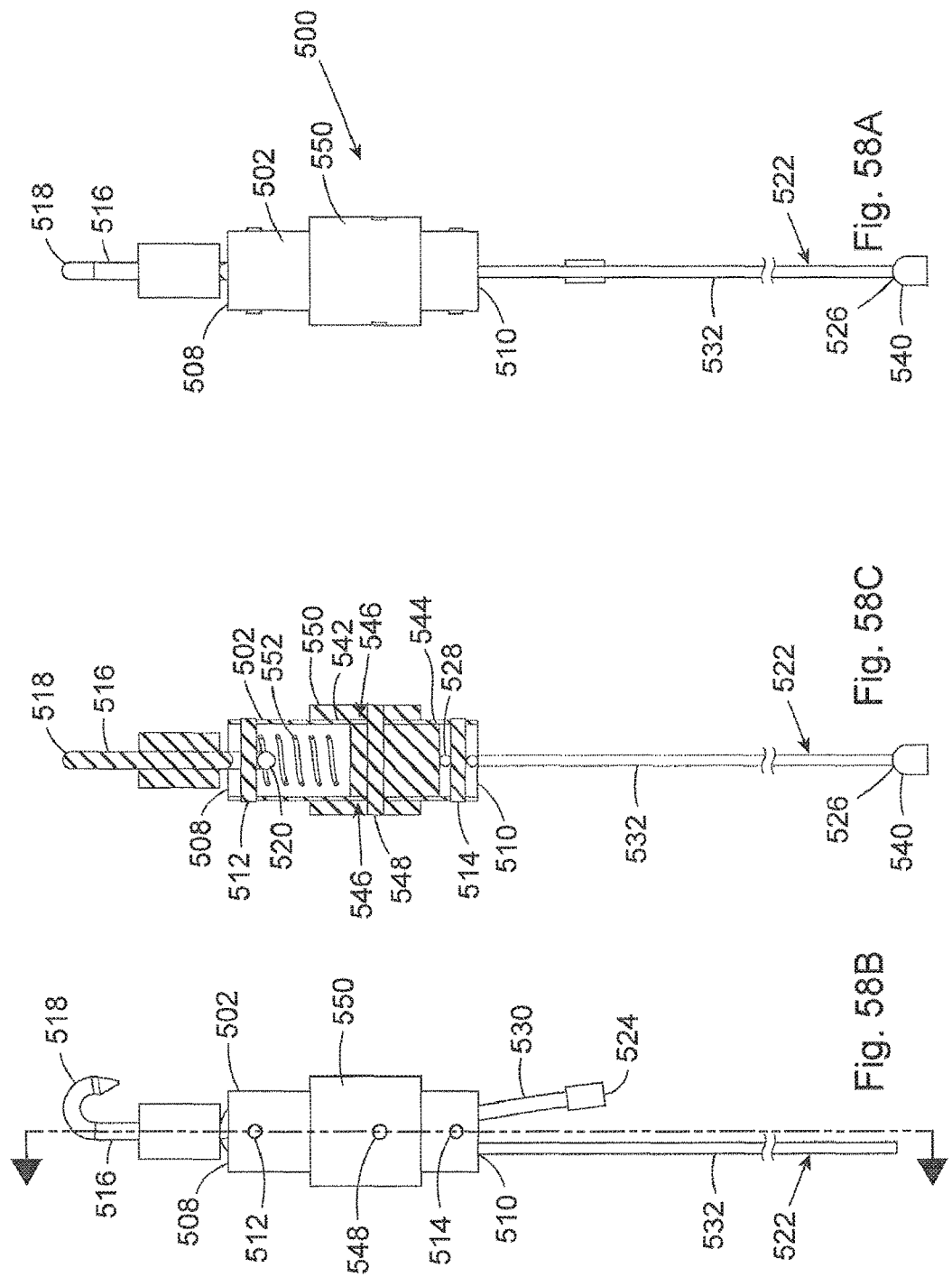

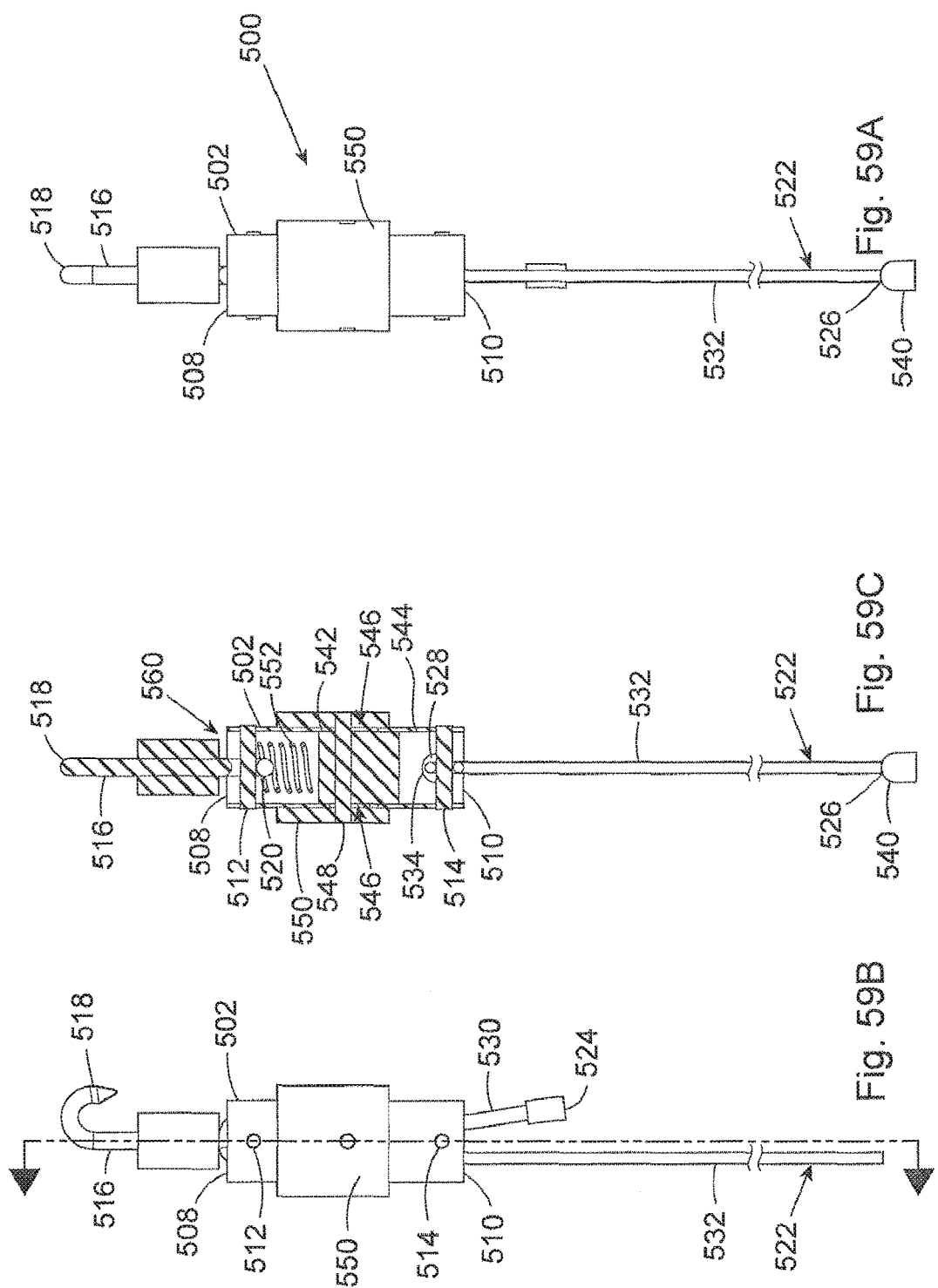

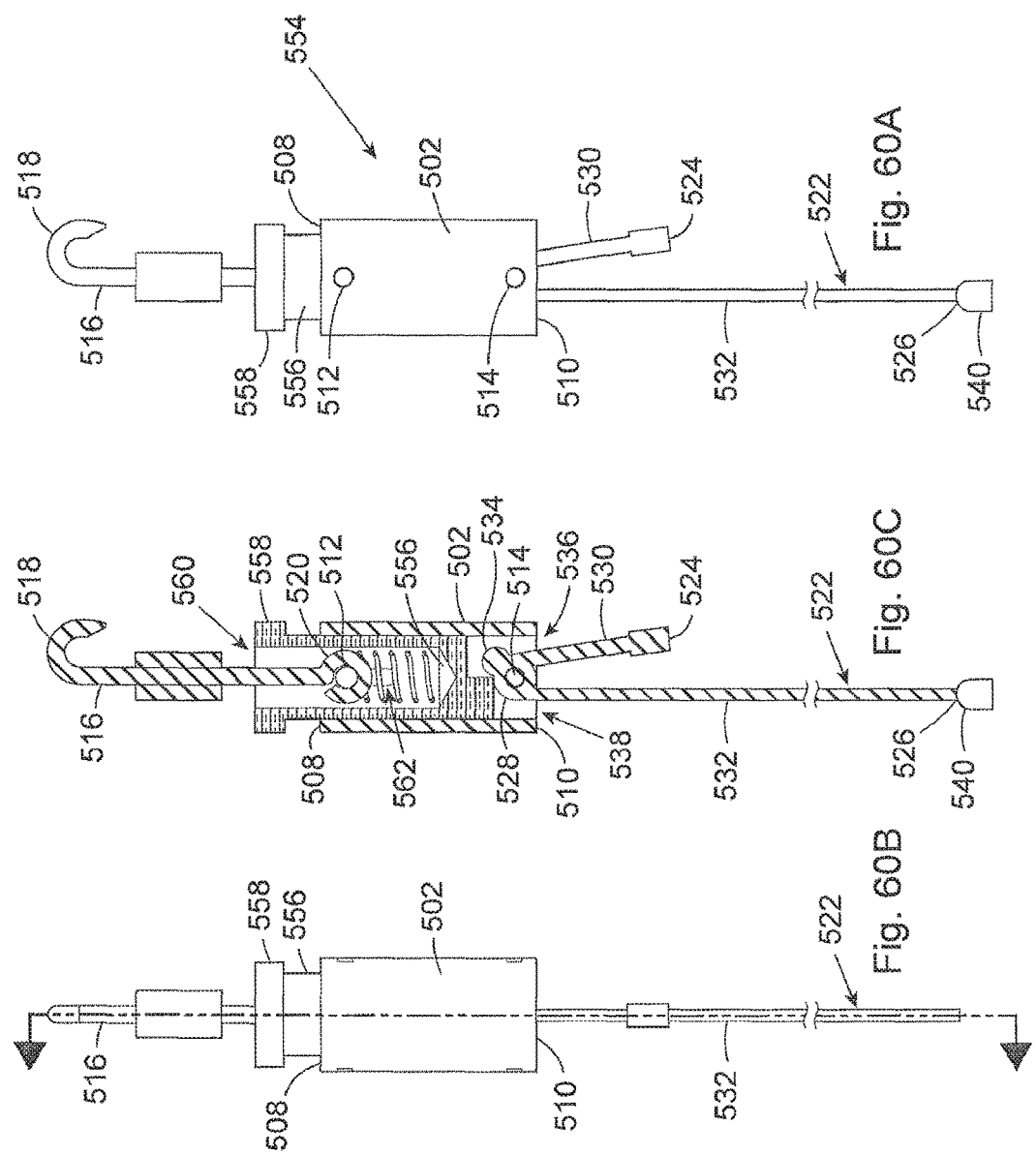

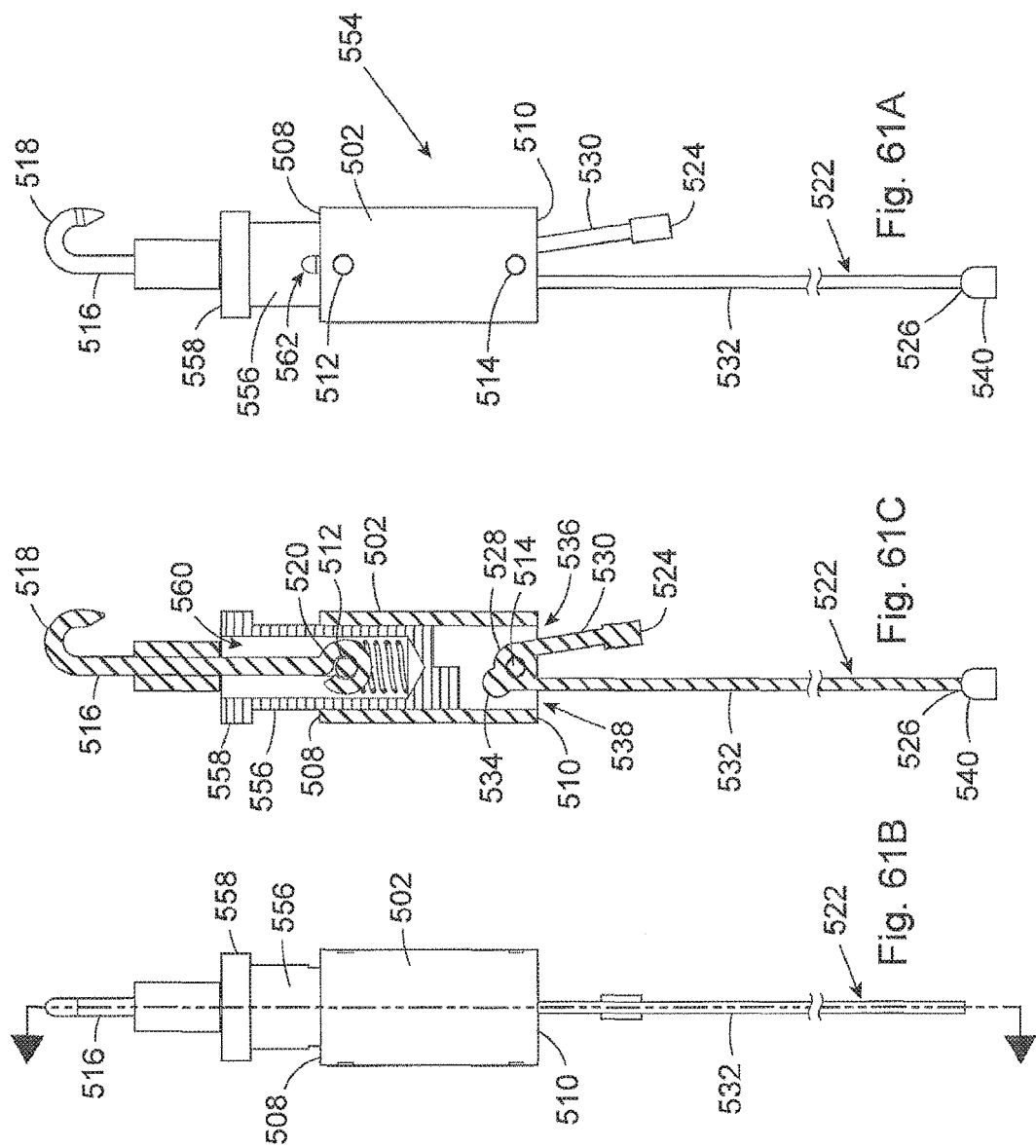

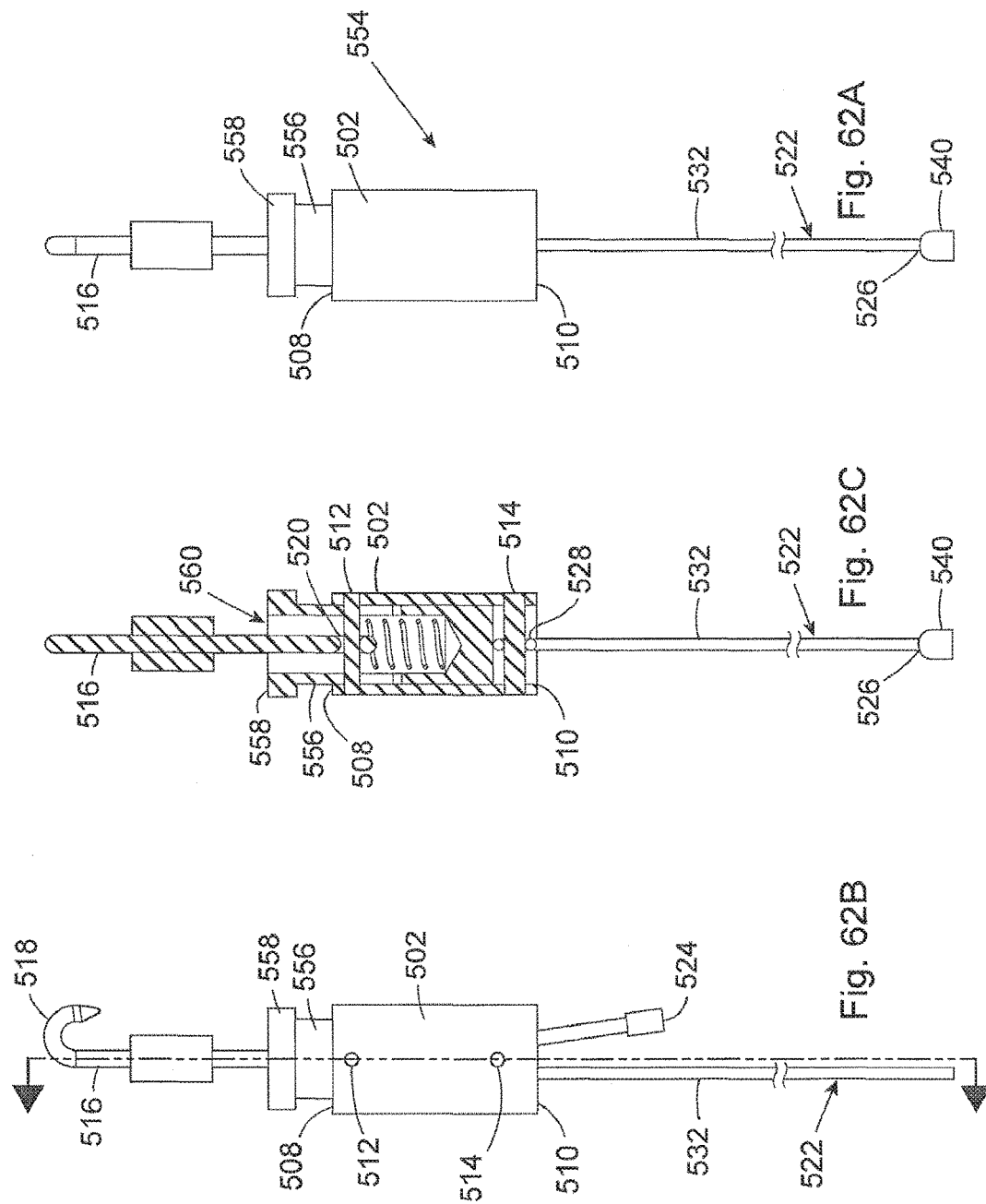

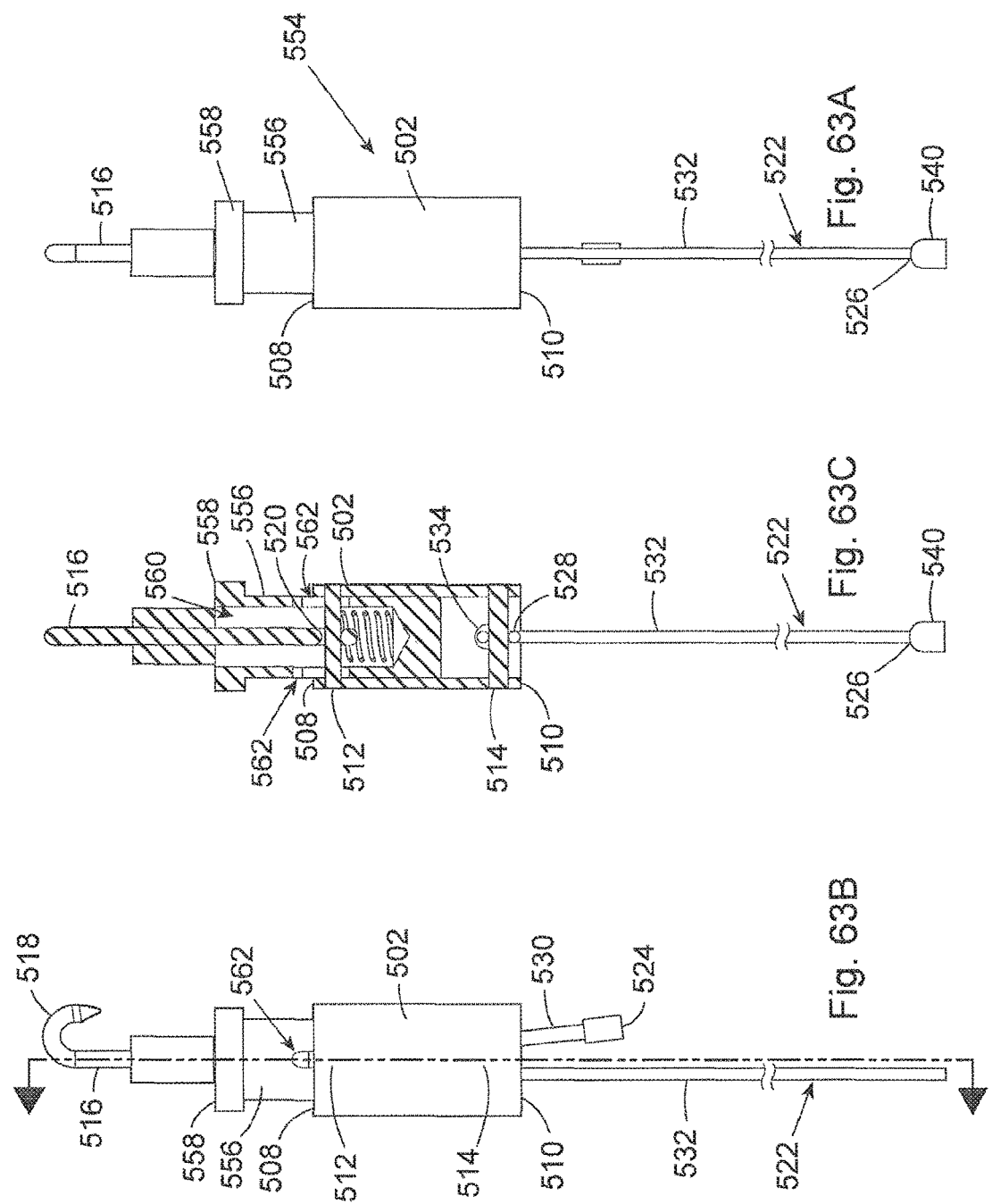

SYSTEM FOR INTRA-ABDOMINALLY MOVING AN ORGAN

This application is a continuation of U.S. application Ser. No. 15/298,144, filed Oct. 19, 2016, pending, which is a continuation of U.S. application Ser. No. 14/240,928, filed Feb. 25, 2014, now abandoned, which is a national stage of PCT Application PCT/US2011/001494 filed Aug. 25, 2011.

BACKGROUND OF THE INVENTION

1. Field of the Invention

The present invention is directed to an apparatus and its method of use in intra-abdominally moving a first internal organ to a position away from a second internal organ where the apparatus holds the first internal organ in the position without further manual input. More specifically, the present invention is directed to an apparatus that is inserted through the abdominal wall and into the abdominal cavity, and the method of using the apparatus in the abdominal cavity to move a human liver to a position away from a human stomach where the apparatus holds the liver in the position without further manual input, thereby providing surgical access to the stomach.

2. Description of the Related Art

In laparoscopic surgical procedures, it is often necessary to make incisions through the abdominal wall for the sole purpose of providing access to the abdominal cavity for surgical graspers or other similar types of retracting instruments that are used to move one internal organ to a position away from a second internal organ to gain surgical access to the second internal organ. The incisions made for the surgical graspers or similar retracting instruments are in addition to the incisions made in the abdominal wall for the surgical instruments used in performing the surgical procedure on the second organ.

Furthermore, it is often necessary that an additional surgeon or surgical assistant be present solely for the purpose of manipulating the surgical graspers or other similar retracting instruments in moving the first internal organ to a position away from the second internal organ, and then manually holding the first internal organ in the position during the surgical procedure performed on the second internal organ.

The need for the additional surgical personnel to manipulate and hold the surgical graspers or other similar retracting instruments during the surgical procedure increases the costs of surgery. In addition, the additional incisions in the abdominal wall required for the surgical graspers or other similar retracting instruments often results in additional discomfort to the patient following surgery and additional scarring.

What is needed to overcome these disadvantages associated with the above-described type of laparoscopic surgical procedure is an apparatus that can be operated to intra-abdominally move a first internal organ to a position away from a second internal organ and then hold the first internal organ in the position without requiring additional manual input other than that provided by the surgeon and without requiring additional abdominal incisions other than those required for the surgery.

SUMMARY OF THE INVENTION

The present invention overcomes the above-described shortcomings of laparoscopic surgical procedures by providing an apparatus that can be inserted into the abdominal cavity through the same incision to be used in a laparoscopic surgery procedure, and the method of using the apparatus to move or retract a first internal organ, for example the liver, away from a second internal organ, for example the stomach, and then hold the first internal organ in the retracted position providing surgical access to the second internal organ without requiring further manual input.

The apparatus is constructed of component parts that are often used in laparoscopic as well as other types of surgical procedures. The component parts will be described herein using their common understood names and their functions, without going into details of the particular constructions of the component parts.

The basic construction of the apparatus of the invention includes a length of cord. The cord could be comprised of a first cord segment having a flexible length with opposite first and second ends, and a second cord segment having a flexible length with opposite first and second ends. The cord segments could be provided by lengths of suture, lengths of tubing such as IV tubing, lengths of umbilical tape or elastic strips, or other equivalent cord constructions. The first and second cord segments could be separate cord segments that are attached together, or could be two cord segments of a single continuous length of cord.

In one embodiment of the apparatus, first, second, and third separate tissue connectors are attached to the first and second cord segments. The tissue connectors can be any type of known tissue connector that can be manually manipulated to connect to body tissue, and then manually manipulated to be removed from the body tissue without leaving any significant damage to the body tissue. In addition, the tissue connectors can be biocompatible tissue connectors that are designed to be left in the abdominal cavity after the surgery. Some examples of such tissue connectors include suture needles, 'T' bars, graspers, barbed needles, hooks, clasps, rivet assemblies, or any other equivalent type of connector. The first and third tissue connectors are attached to the opposite ends of the first cord segment and the second and third tissue connectors are attached to the opposite ends of the second cord segment. This positions the first and second tissue connectors at the opposite ends of the combined lengths of the first and second cord segments, and positions the third tissue connector at an intermediate position of the combined lengths of the first and second cord segments.

In the use of the apparatus according to the method of the invention, the apparatus is first manually passed through the abdominal wall, for example through an incision or a cannula in the abdominal wall, and is positioned in the abdominal cavity in the area of the first and second internal organs. The third tissue connector is then manually connected to tissue adjacent the first internal organ. This positions the ends of the first and second cord segments connected to the third tissue connector between the first and second internal organs and on an opposite side of the first internal organ from the abdominal wall. The first tissue connector attached to the opposite end of the first cord segment from the third tissue connector is manually moved causing the length of the first cord segment to move and engage across the first internal organ and to move the first internal organ toward the position away from the second internal organ. The first tissue connector is then manually connected to the abdominal wall.

The second tissue connector attached to the opposite end of the second cord segment from the third tissue connector is then manually moved causing the second cord segment to move and engage across the first internal organ and move the first internal organ toward the position away from the second internal organ. The second tissue connector is then manually connected to the abdominal wall.

In the above matter, the first and second cord segments engaging across the first internal organ hold the first internal organ at the position away from the second internal organ without further manual input. This provides surgical access to the second internal organ.

In a further embodiment of the apparatus of the invention, the apparatus is comprised of a cord having a continuous flexible length with opposite first and second ends. A needle is attached to one end of the length of cord and a knot is formed in the opposite end of the length of cord.

According to the method of use of this embodiment of the apparatus, the apparatus is first positioned inside the abdominal cavity in the same manner as the previously-described embodiment. The knotted end of the length of cord is then connected to tissue adjacent the first internal organ by first passing the needle through the tissue and then manually pulling the length of cord through the tissue. This attaches the knotted end of the cord to the tissue between the first and second internal organs.

The needle is then passed through the inter-abdominal wall and manually moved back into the abdominal cavity, causing a first segment of the length of cord to engage across the first internal organ and move the first internal organ toward the position away from the second internal organ.

The needle is then again inserted through the inter-abdominal wall at a location spaced from the first insertion of the needle through the inter-abdominal wall, and the needle and length of cord are pulled manually into the abdominal cavity.

The needle and the end of the length of cord attached to the needle are f< then passed through the knot formed at the opposite end of the length of cord and pulled tight, causing a second segment of the length of cord to engage across and move the first internal organ toward the position away from a second internal organ. A knot is then tied between the opposite ends of the length of cord and the portion of the cord extending from the knot to the needle is cut and removed with the needle from the abdominal cavity. The length of cord left in the abdominal cavity forms a triangular loop with first and second cord segments that engage across and hold the first internal organ in the position away from the second internal organ without manual input. In this manner, surgical access is provided to the second internal organ without manual input.

A still further embodiment of the apparatus of the invention is comprised of a cord having a continuous flexible length with opposite first and second ends, and a tissue connector assembly with a releasable one-way cord lock connected to an intermediate portion of the cord.

The tissue connector assembly has a base formed as a cylindrical housing. The base housing has a length with opposite first and second ends and a hollow interior bore extending through the housing. A rod is attached to the base and is positioned in the interior bore adjacent the housing second end.

A first tissue connector is provided on the base and extends from the base first end. As in previous embodiments, the tissue connector can be any known type of tissue connector.

The intermediate portion of the cord length is attached to the base by being wrapped around the rod in the base housing. A first portion or first percentage of the cord length extends from the cord intermediate portion and from the base second end to the cord first end. A second portion or second percentage of the cord length extends from the cord intermediate portion and from the base second end to the cord second end.

A releasable one-way lock is mounted in the interior bore of the base for movement of the lock between first and second positions of the lock relative to the base. The lock is biased by a spring toward the first position. In the first position of the lock relative to the base, the lock engages with the intermediate portion of the cord wrapped around the rod and allows the cord first portion to be pulled from the base second end to thereby increase a length or percentage of the cord first portion while decreasing a length or percentage of the cord second portion, but the lock prevents the cord second portion from being pulled from the base second end. In the second position of the lock relative to the base the lock is disengaged from the cord and allows the cord second portion to be pulled from the base second end to thereby increase the length or percentage of the cord second portion while decreasing the length or percentage of the cord first portion.

A second tissue connector is provided at the cord second end. Again, the second tissue connector can be any known type of tissue connector. A percentage of the cord length extends between the first and second tissue connectors. This percentage of the cord length is adjustable.

There is an actuator on the base that is operatively connected to the lock. The actuator is movable between first and second positions of the actuator relative to the base. When the actuator is moved from the first position to its second position it causes the lock to move from its first position to its second position and releases the one way lock. The spring bias of the lock also biases the actuator from its second position toward its first position.

In the use of this embodiment of the apparatus according to the method of the invention, the apparatus is first positioned inside the abdominal cavity in the same manner as the previously described embodiments.

With the apparatus positioned in the abdominal cavity, the second tissue connector at the cord's second end is connected to tissue adjacent to the first internal organ or to the organ itself. The tissue connector assembly with the releasable one-way cord lock is then grasped at the actuator and moved toward the abdominal wall, causing the cord second portion to be extended across the first internal organ. When the cord second portion is pulled tight continued movement of the tissue connector assembly causes the actuator to move to its second position. This releases the lock and allows the cord second portion to be pulled from the base second end increasing the length or percentage of the cord second portion and decreasing the length or percentage of the cord first portion. The first tissue connector is then connected to the abdominal wall and the actuator is released, causing the actuator and the lock to move to their first position due to the bias of the spring. The cord first portion is then grasped and pulled from the second end of the base. This in turn causes the length or percentage of the cord second portion to decrease. As the cord first portion is pulled from the base second end the length or percentage of the cord second portion continues to decrease and causes the cord second portion to engage across the first internal organ and move the first internal organ toward the position away from the second internal organ. With the releasable one-way lock biased to the first position relative to the base, the cord second portion cannot be pulled from the base.

In the above manner, the shortened length of the cord second portion extending between the first tissue connector connected to the abdominal wall and the second tissue connector connected to the body tissue adjacent the first internal organ engages across the first internal organ and holds the first internal organ at the position away from the second internal organ without further manual input. This provides surgical access to the second internal organ.

When it is desired to remove the apparatus of the invention, the actuator is grasped and moved from its first position to its second position relative to the apparatus base. This in turn causes the lock to move from its first position to its second position releasing the lock, and allows the cord second portion to be pulled from the base second end increasing the length or percentage of the cord second portion while decreasing the length or percentage of the cord first portion. This allows the cord second portion to disengage from the first internal organ and produces a sufficient length of the cord second portion to allow the first tissue connector to be removed from the abdominal wall and the second tissue connector at the cord second end to be removed from the body tissue adjacent the first internal organ or from the organ. The apparatus then can be removed from the abdominal cavity.

As described above, the embodiments of the apparatus of the invention and their methods of use enable intra-abdominally moving a first internal organ to a position away from a second internal organ where each of the embodiments of the apparatus holds the first internal organ in the position without manual input.

DESCRIPTION OF THE DRAWING FIGURES

Further features of the apparatus of the invention and its method of use are set forth in the following detailed description of the apparatus and method and are shown in the drawing figures.

FIGS. 20A and 20B represent a further embodiment of the apparatus and its method of use.

FIGS. 21A and 21B represent a further embodiment of the apparatus and its method of use.

FIGS. 22A and 22B represent a further embodiment of the apparatus and its method of use.

FIGS. 44A and 44B represent component parts of an embodiment of the apparatus.

FIGS. 45A-45E represent component parts of an embodiment of the apparatus.

FIGS. 47A-47D represent component parts of an embodiment of the apparatus and its method of use.

FIGS. 48A-48D represent component parts of an embodiment of the apparatus and its method of use.

FIGS. 49A and 49B represent component parts of an embodiment of the apparatus and its method of use.

FIGS. 51A-51E represent a method of positioning an embodiment of the apparatus in an abdominal insertion device.

FIGS. 56A-56C are views of a further embodiment of the apparatus of the invention that employs a tissue connector with a releasable one-way cord lock.

FIGS. 57A-57C are views of the tissue connector apparatus of FIGS. 56A-56C but rotated 90°.

FIGS. 58A-58C are views of the tissue connector apparatus similar to those of FIGS. 56A-56C, but with the releasable one-way cord lock moved to an unlocked position.

FIGS. 59A-59C are views of the surgical tissue connector apparatus shown in FIGS. 58A-58C, but rotated 90°.

FIGS. 60A-60C show a further embodiment of the surgical tissue connector apparatus with a releasable one-way cord lock.

FIGS. 61A-61C are views of the tissue connector apparatus of FIGS. 60A-60C, but rotated 90°.

FIGS. 62A-62C are views of the tissue connector apparatus similar to those of FIGS. 60A-60C, but with the releasable one-way cord lock moved to the unlocked position.

FIGS. 63A-63C are views similar to those of FIGS. 62A-62C, but rotated 90°.

DETAILED DESCRIPTION OF THE PREFERRED EMBODIMENT

Figure 1:
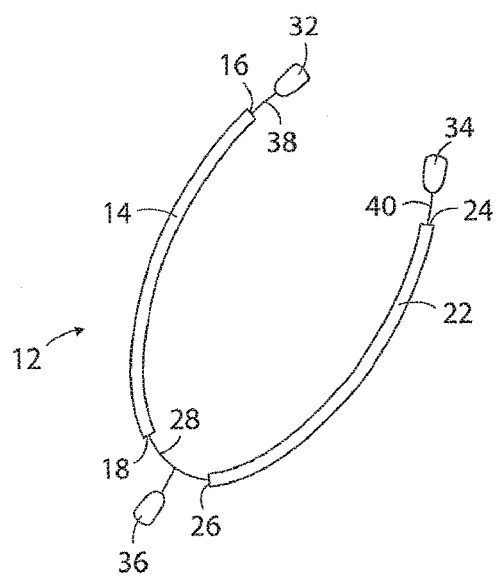
FIG. 1 is a plan view of one embodiment of the apparatus of the invention.

FIG. 1 shows one embodiment 12 of the apparatus for intra-abdominally moving a first internal organ to a position away from a second internal organ and then holding the first internal organ in the position without manual input. As stated earlier, the apparatus 12 is constructed of component parts that are often used in laparoscopic instruments and procedures as well as other types of surgical instruments and procedures. Because such component parts are known, the component parts that make up the apparatus 12 of the invention will be described herein using their common understood names and functions, without going into the details of the particular constructions of the component parts. As is conventional with laparoscopic apparatus, the component parts of the apparatus are dimensioned to be inserted through an incision in the abdominal wall or through a cannula extending through the abdominal wall to position the apparatus in the abdominal cavity.

The basic construction of the apparatus 12 of the invention includes a length of cord. In the example of FIG. 1 the cord length is 10 inches, but the size of the apparatus 12 could change depending on the size of the patient in which the apparatus is used. In the embodiment shown in FIG. 1, the cord is comprised of a first cord segment 14 having a flexible length with opposite first 16 and second 18 ends, and a second cord segment 22 having a flexible length with opposite first 24 and second 26 ends.

The cord segments 14, 22 could be provided by lengths of suture, lengths of tubing such as IV tubing, lengths of umbilical tape or elastic strips, or other equivalent cord constructions. The tubing or tape configurations of the cord segments have the advantage of being less likely to dig into or cut into the first internal organ in use of the apparatus to be described. The first 14 and second 22 cord segments could be separate cord segments that are attached directly together, or separate cord segments that are attached by way of a further cord segment 28 or some other component part of the apparatus, or two cord segments of a single continuous length of cord such as the two cord segments 14a, 22a shown in FIG. 2.

Figure 2:
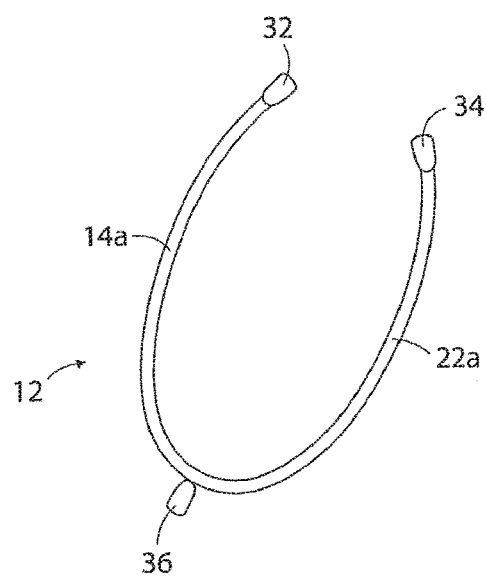
FIG. 2 is a plan view of a further embodiment of the apparatus of the invention.

First 32, second 34, and third 36 separate tissue connectors are attached to the first 14 and second 22 cord segments. The tissue connectors 32, 34, 36 can be any type of known tissue connector that can be manually manipulated to connect to body tissue, and then manually manipulated to be removed from the body tissue 12 without leaving any significant damage to the body tissue. In addition, the tissue connectors 32, 34, 36 could be biocompatible tissue connectors that are designed to be left in the abdominal cavity after the surgical procedure is completed. Some examples of tissue connectors include suture needles, T bars, surgical graspers, barbed needles, hooks, clasps, rivet assemblies, or any other equivalent type of connector. In the apparatus of the invention, it is not necessary that all three tissue connectors 32, 34, 36 be the same type of tissue connector. Because various different types of tissue connectors may be employed with the apparatus 12 of the invention, the three tissue connectors 32, 34, 36 of the apparatus 12 are represented schematically in the drawing figures. The first 32 and third 36 tissue connectors are attached to the opposite ends of the first cord segment 14. The third tissue connector 36 is also attached to one end of the second cord segment 22, with the second tissue connector 34 being connected to the opposite end of the second cord segment 22. This positions the first 32 and second 34 tissue connectors at the opposite ends of the combined lengths of the first 14 and second 22 cord segments, and positions the third tissue connector 36 at an intermediate position of the combined length of the first 14 and second 22 cord segments. In FIG. 1, the first 32 and second 34 tissue connectors are shown connected to the respective first end 16 of the first cord segment 14 and the first end 24 of the second cord segment 22 through the intermediary of additional cord segments 38, 40. The third tissue connector 36 is shown connected to the second end 18 of the first cord segment 14 and the second end 26 of the second cord segment 22 through the intermediary of a further cord segment 28. FIG. 2 shows the apparatus 12 with the first 32 and second 34 tissue connectors connected directly to the respective first end 16 of the first cord segment 14 and the first end 24 of the second cord segment 22. FIG. 2 also shows the third tissue connector 36 connected directly to the second ends 18, 26 of the first cord segment 14 and the second cord segment 22.

Figure 4:
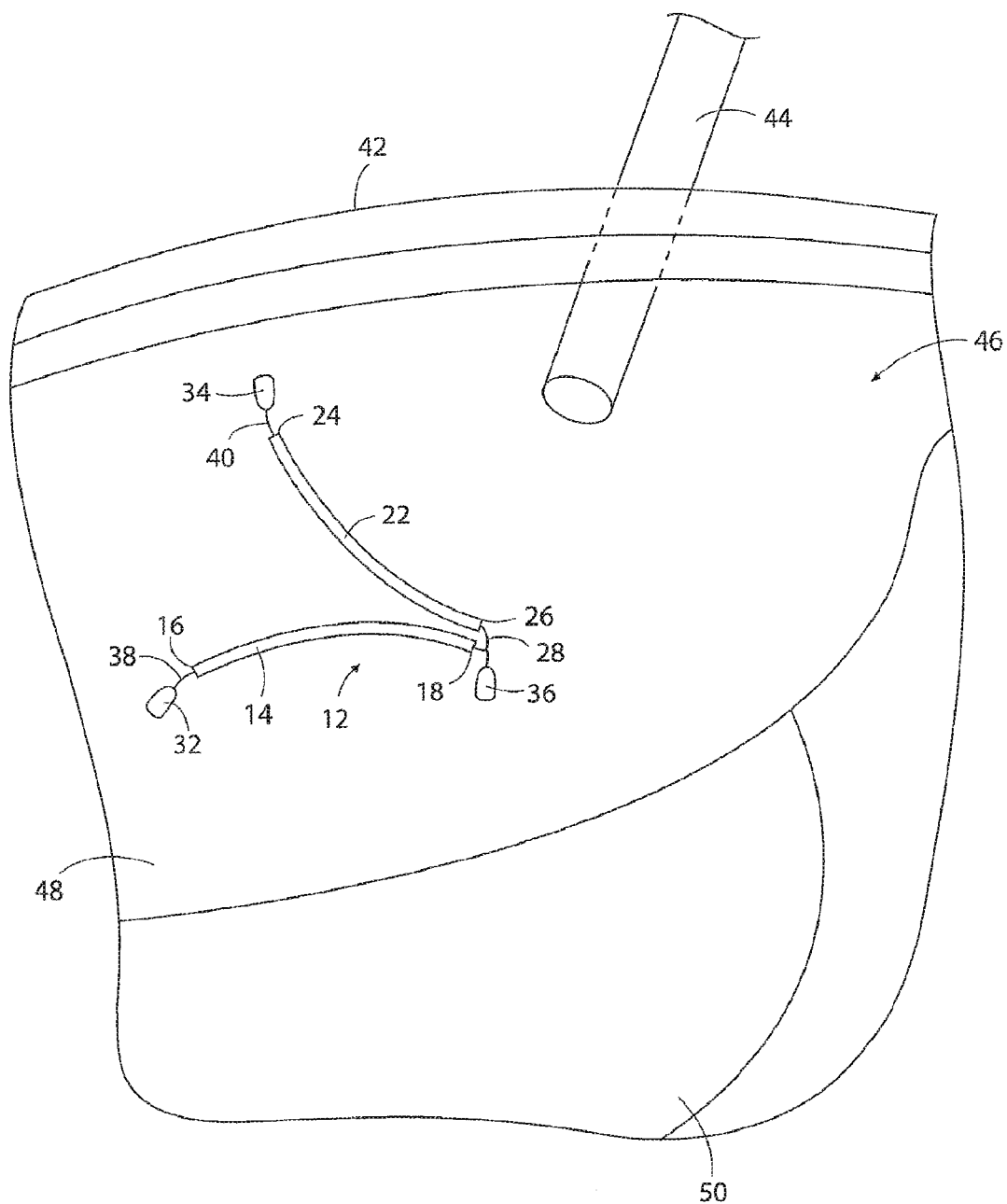
FIG. 4 is a representation of the apparatus of FIG. 1 being inserted into the abdominal cavity.
Figure 5:
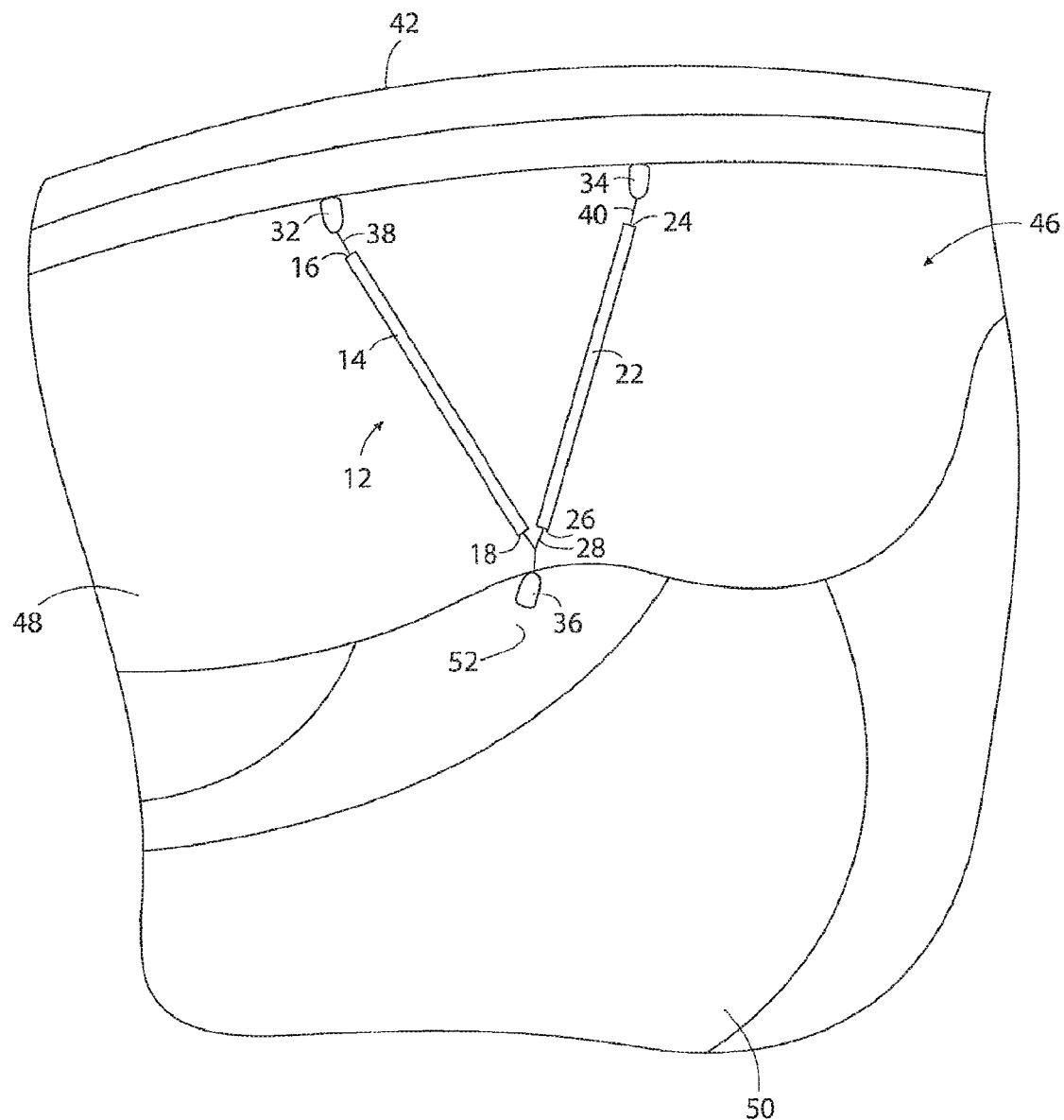
FIG. 5 is a representation of the apparatus of FIG. 1 being used according to the method of the invention.

FIGS. 4 and 5 illustrate an example of the use of the apparatus 12 of FIG. 1 according to the method of the invention. In use, the apparatus 12 is first manually passed through the abdominal wall 42, for example through an incision or a cannula 44 in the abdominal wall 42, and is positioned in the abdominal cavity 46 in the area of the first 48 and second 50 internal organs. In FIG. 4, the first internal organ 48 represented is the human liver, and the second internal organ 50 represented is the human stomach.

The third tissue connector 36 of the apparatus is then manually connected to tissue 52 adjacent the first internal organ 48 and between the first 48 and second 50 internal organs. In the example shown in FIG. 4, the tissue 52 is the crus of the diaphragm. Connection of the third tissue connector 36 to the tissue 52 positions the second ends 18, 26 of the first 14 and second 22 cord segments connected to the third tissue connector 32 between the first 48 and second 50 internal organs and on an opposite side of the first internal organ 48 from the abdominal wall 42.

The first tissue connector 32 attached to the opposite end 16 of the first cord segment 14 from the third tissue connector 36 is then manually moved causing the length of the first cord segment 14 to move and engage across the first internal organ 48. Continued movement of the first tissue connector 32 causes the first cord segment 14 engaging across the first internal organ 48 to move the first internal organ toward a position away from the second internal organ 50. The first tissue connector 32 is then manually connected to the inner abdominal wall 42.

The second tissue connector 34 attached to the opposite end 24 of the second cord segment 22 from the third tissue connector 36 is then manually moved causing the second cord segment 22 to move and engage across the first internal organ 48. Continued movement of the second tissue connector 34 causes the second cord segment 22 engaging across the first internal organ 48 to move the first internal organ 48 toward the position away from the second internal organ 50. The second tissue connector 34 is then manually connected to the inner abdominal wall 42.

With the apparatus 12 connected between the tissue 52 and the inner abdominal wall 42 in the manner discussed above, the first cord segment 14 and the second cord segment 22 engage across the first internal organ 48 and hold the first internal organ 48 at the position away from the second internal organ 50 without further manual input. This provides surgical access to the second internal organ 50. Without requiring manual holding or restraining of the first internal organ 48 in the position away from the second internal organ 50.

Figure 6:
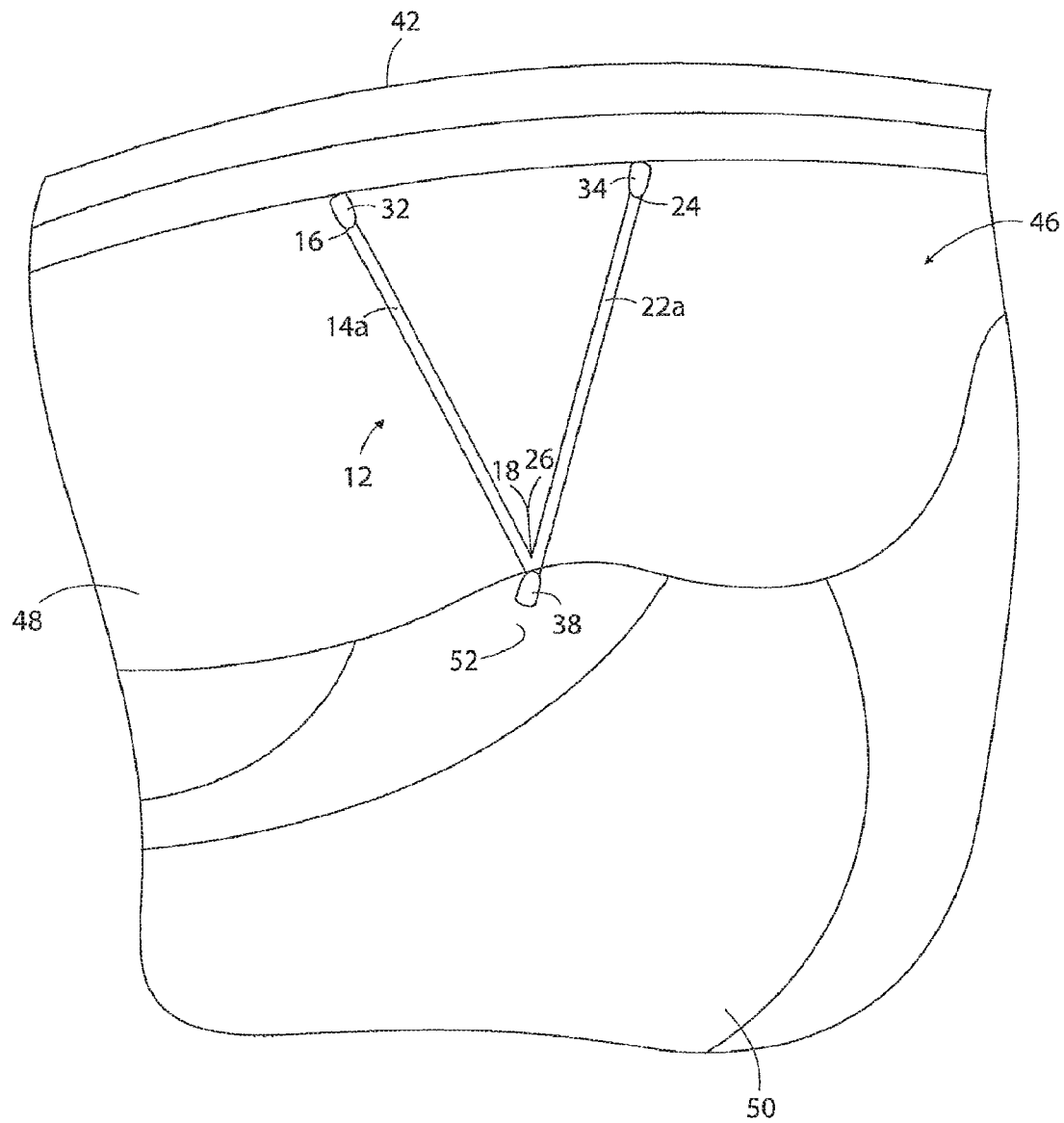
FIG. 6 is a representation of the apparatus of FIG. 2 in use according to the method of the invention.

FIG. 6 is a representation of the apparatus of FIG. 2 that has been connected between the tissue 52 and the inner abdominal wall 42 according to the same method as the apparatus of FIG. 1 described above.

Figure 3:
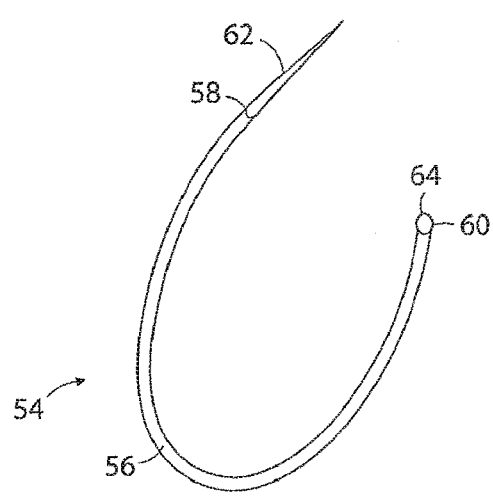
FIG. 3 is a plan view of a still further embodiment of the apparatus of the invention.

In a further embodiment of the apparatus of the invention shown in FIG. 3, the apparatus 54 is comprised of a single cord 56 having a continuous flexible length with opposite first 58 and second 60 ends. A tissue connector in the form of a needle 62 is attached to the first end 58 of the length of cord 56. At the opposite second end 60 of the length of cord 56, the cord is formed in a knot 64.

Figure 7:
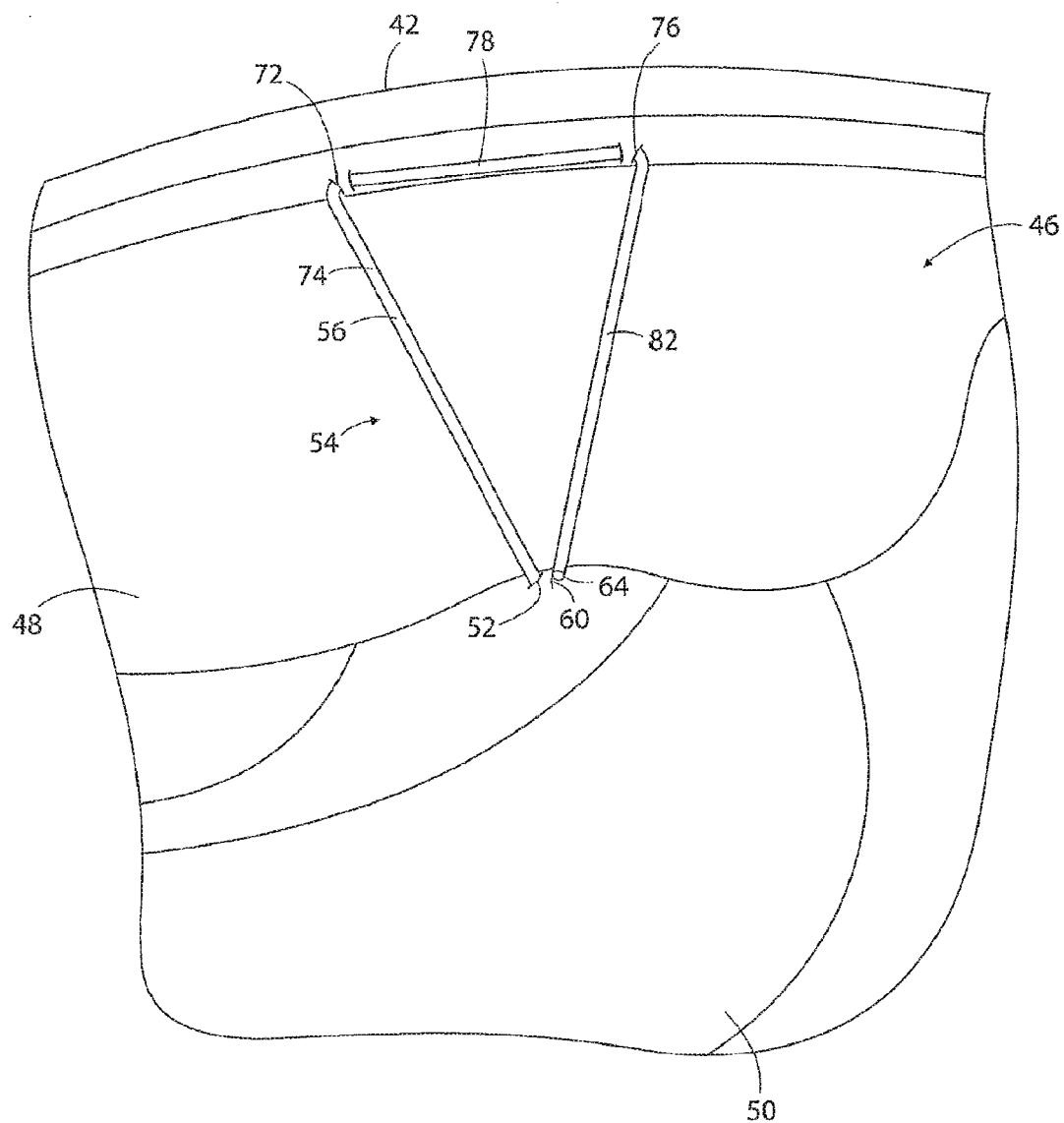
FIG. 7 is a representation of the apparatus of FIG. 3 in use according to the method of the invention.

The method of using the embodiment of the apparatus 54 shown in FIG. 3 is illustrated in FIG. 7. The apparatus 54 is first positioned inside the abdominal cavity in the same manner as the previously described embodiments. The knotted end 64 of the length of cord is then connected to the tissue 52 adjacent the first internal organ 48 by first passing the needle 62 through the tissue 52 and then manually pulling the needle 62 and the attached length of cord 56 through the tissue 52. This attaches the knotted second end 64 of the length of cord 56 to the tissue 52 between the first 48 and second 50 internal organs.

The needle 62 is then passed through the inter-abdominal wall 42 and the needle 62 and the attached length of cord 56 are pulled from the insertion site 72 back into the abdominal cavity 46. This causes a first segment 74 of the cord length 56 to move into engagement with and across the first internal organ 48. The engagement of the first cord segment 74 with the first internal organ 48 moves the first internal organ 48 toward the position away from the second internal organ 50.

The needle 62 is then again inserted through the inter-abdominal wall 42 at a second insertion location 76 spaced from the first insertion location 72. The needle 62 and the attached length of cord 56 are pulled manually through the second insertion 76 into the abdominal cavity 46 until an intermediate section of cord 78 extends between the two insertion sites 72, 76.

The needle 62 and the attached length of cord 56 are then passed through the knot 64 formed at the opposite end of the length of cord 56 and are pulled tight. This causes a second cord segment 82 of the length of cord 56 to engage across and move the first internal organ 48 toward the position away from the second internal organ 50. The length of cord 56 is pulled tight and a knot is tied between the opposite ends of the cord at the knot 64 on the cord second end 60. The portion of the length of cord 54 extending from the knot 64 to the needle 62 is then cut and removed from the abdominal cavity. The length of cord 54 left in the abdominal cavity forms a triangular loop with the first 56 and second 82 cord segments extending across the first internal organ 48 and holding the first internal organ in the position away from the second internal organ 50 without manual input. In this manner, surgical access is provided to the second internal organ 50 without manually holding the first internal organ 48 in its retracted position.

Figure 8A:
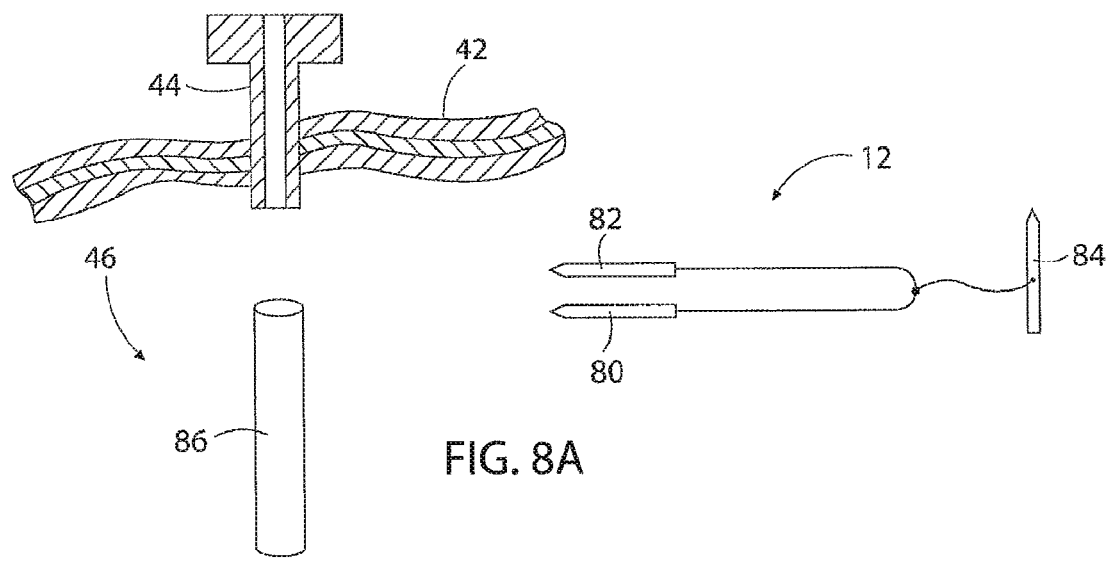
FIGS. 8A-8E represent the insertion of one embodiment of the apparatus into the abdominal cavity and one method of use of the apparatus.
Figure 8B:
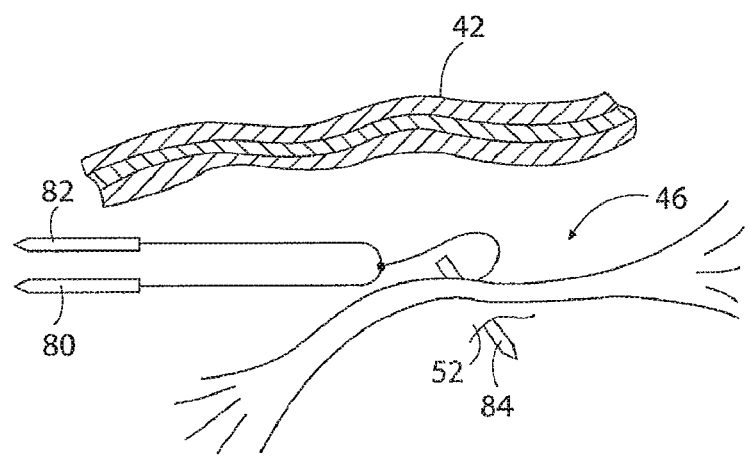
Figure 8C:
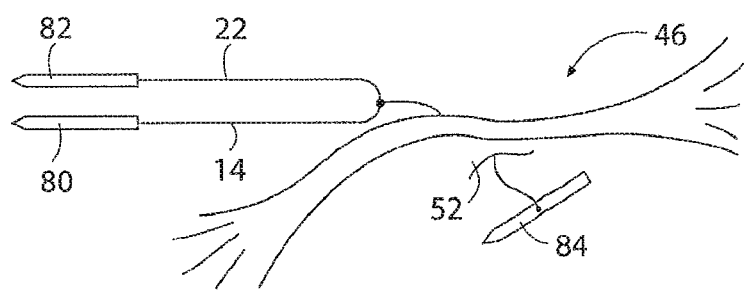
Figure 8D:
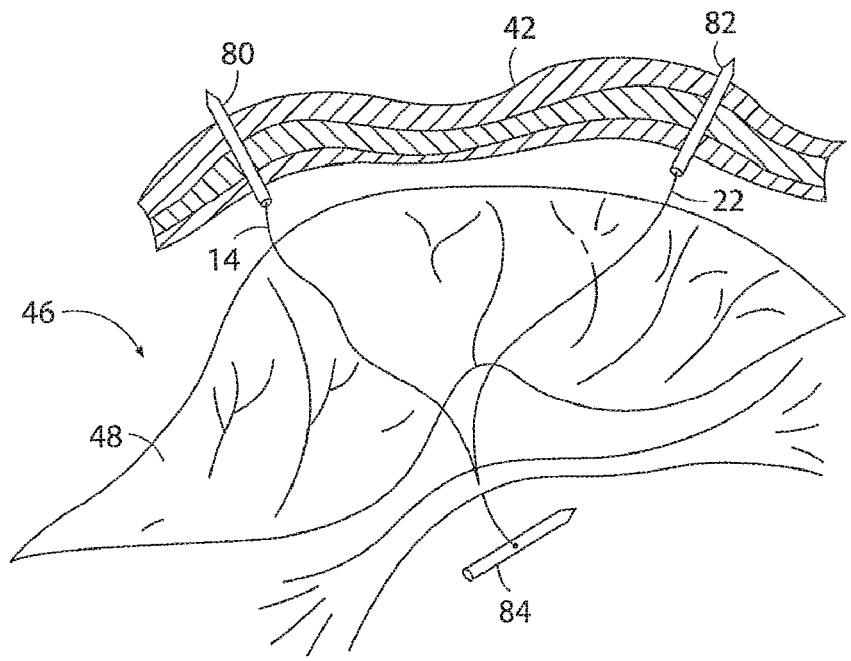
Figure 8E:
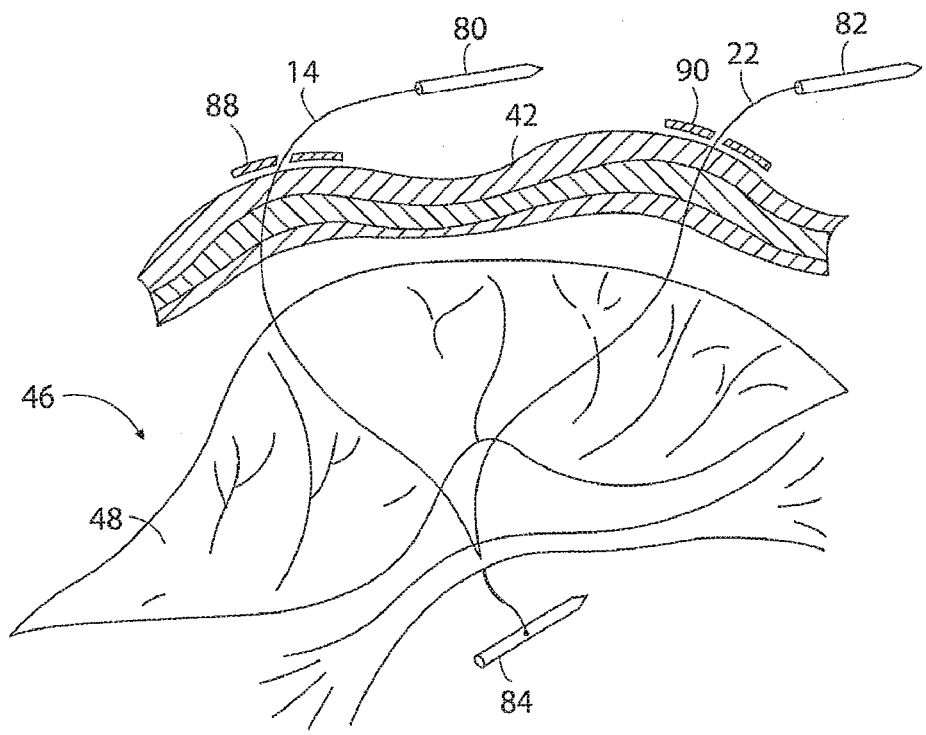

FIGS. 8A-8E represent one method of inserting the apparatus of the invention into the abdominal cavity and the method of using the apparatus. The embodiment of the apparatus 12 shown in these drawing figures has a pair of keith needles 80, 82 as the first and second tissue connectors, and a T bar 84 as the third tissue connector. The apparatus 12 is first positioned inside an insertion device 86 in the form of a hollow narrow tube. The insertion device 86 is then inserted through a trocar or cannula 44 that has been positioned in the abdominal wall 42 in a conventional manner. Once inside the abdominal cavity 46, the apparatus 12 is removed from the interior of the insertion device 86 and the insertion device is removed from the abdominal cavity through the cannula 44. The T bar 84 or the third tissue connector is then passed through the body tissue 52, i.e., the right diaphragm crus as described earlier. Once the T bar 84 is passed through the tissue 52, it is rotated to its substantially 90 degree position relative to its pathway through the tissue 52 as shown in FIG. 8C. The apparatus 12 is then pulled from the keith needles 80, 82. As represented in FIG. 80, the keith needles 80, 82 are then passed through the abdominal wall 42 and the apparatus is pulled tight against the first internal organ 48, i.e., the liver. The needles 80, 82 are then pulled at the exterior of the abdominal wall 42, causing the apparatus to move the first internal organ 48 away from the second internal organ, i.e., the stomach. A pair of tension clasps 88, 90 are attached to the respective first 14 and second 22 cord segments of the apparatus on the exterior of the abdominal wall 42 to hold the apparatus in its position across the first internal organ 48 in the abdominal cavity 46.

Figure 9A:
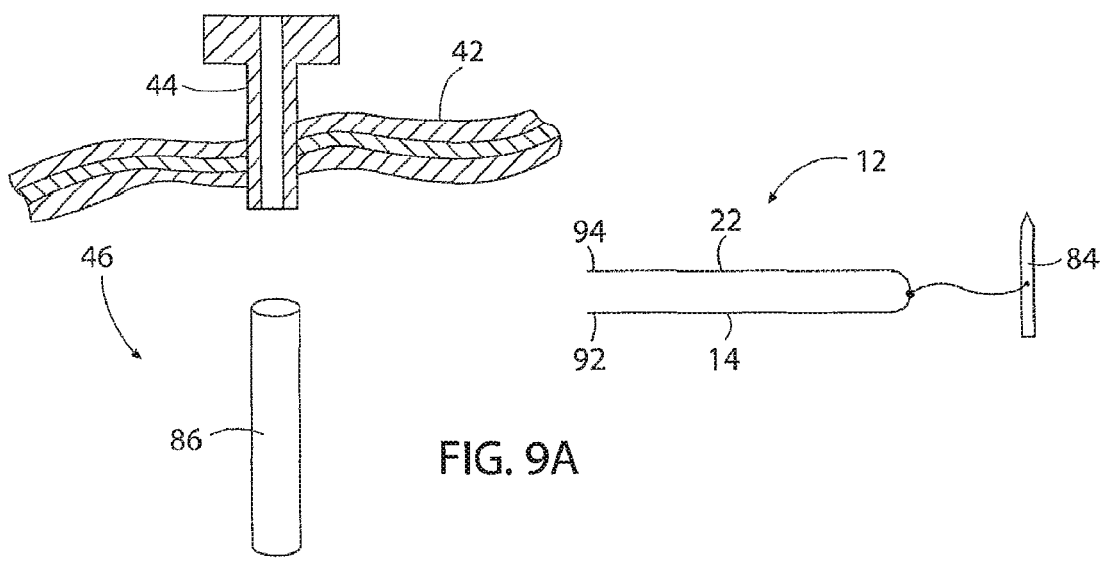
FIGS. 9A-9E represent the insertion of a further embodiment of the apparatus into the abdominal cavity and the method of using the apparatus.
Figure 9B:
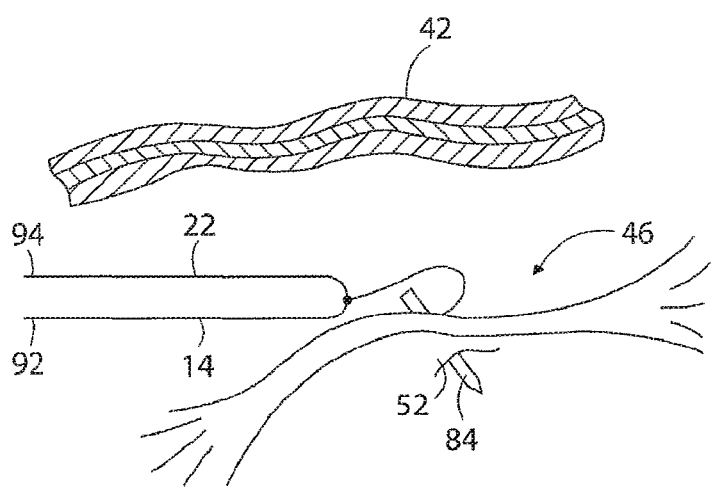
Figure 9C:
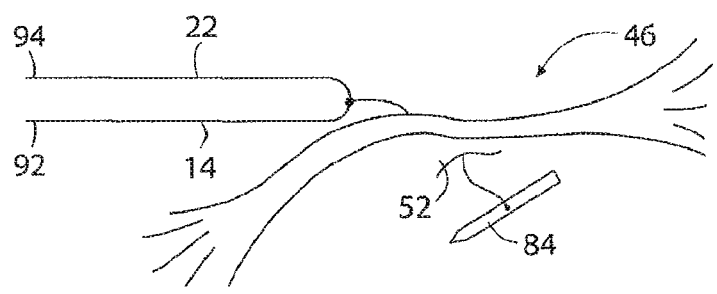
Figure 9D:
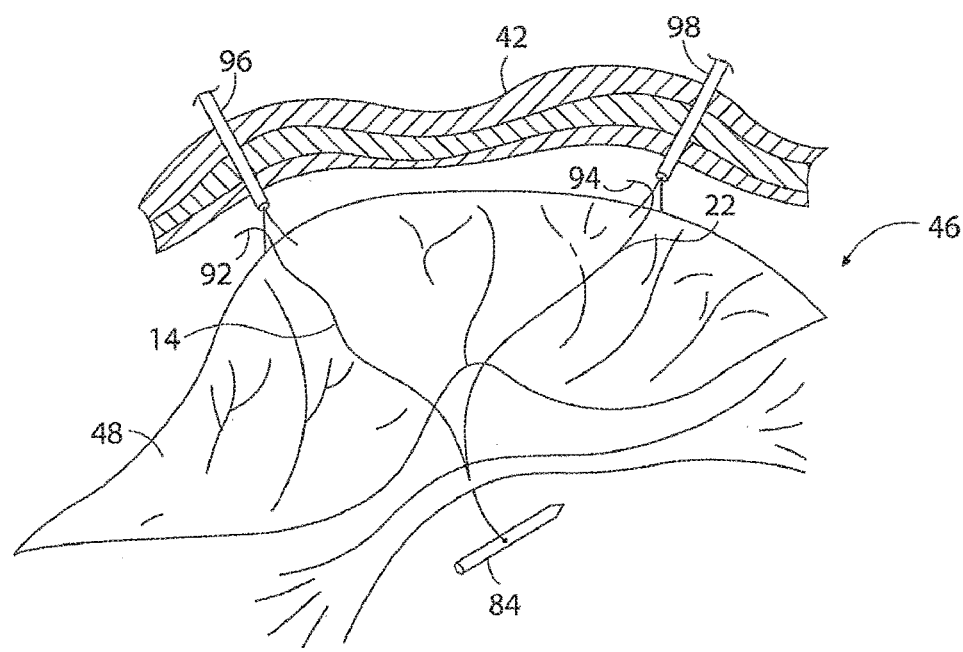
Figure 9E:
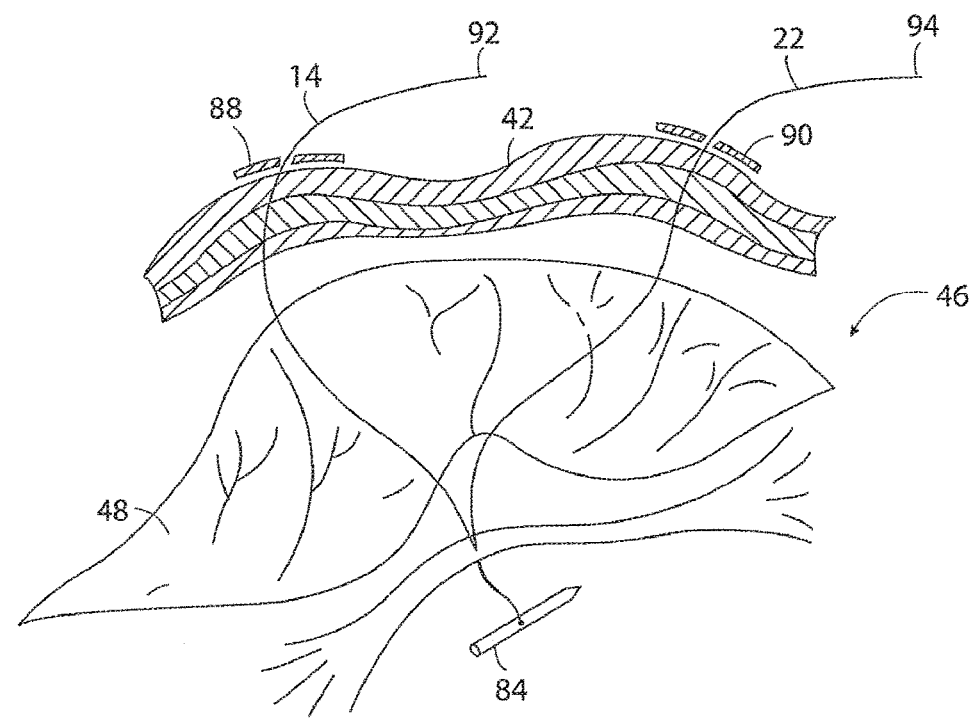

FIGS. 9A-9E represent a method of using an embodiment of the apparatus 12 that is similar to that shown in FIGS. 8A-8E and described above. In this example, the apparatus 12 also employs the T bar 84 as its third tissue connector. However, there is no needle provided on the first cord segment 14 and there is no needle provided on the second cord segment 22. In this embodiment of the apparatus 12, the first cord segment 14 is a length of suture having a free end 92 opposite the T bar 84 and the second cord segment 22 is a length of suture also having a free end 94 opposite the T bar 84. The apparatus 12 is shown in FIG. 9A as being positioned in the abdominal cavity 46 using the insertion device 86 in the same manner described earlier with reference to the method of FIGS. 8A-8E. The apparatus 12 of FIG. 9A is also initially used according to the same method of FIGS. 8A-8E in that the "T" bar 84 is passed through the body tissue 52 and is positioned substantially 90° relative to the pathway through the tissue. A pair 18 of GraNee needles 96, 98 are then passed through the abdominal wall 42. One of the GraNee needles 96 grabs the suture free end 92 of the first cord segment 14 and the other GraNee needle 98 grabs the suture free end 94 of the second cord segment 22. The GraNee needles 96, 98 are then withdrawn through the abdominal wall 42 pulling the suture free ends 92, 94 through the abdominal wall. The suture free ends 92, 94 are then secured to the abdominal wall using a pair of clamps 88, 90 as was done in the previously-described embodiment of FIGS. 8A-8E.

Figure 10A:
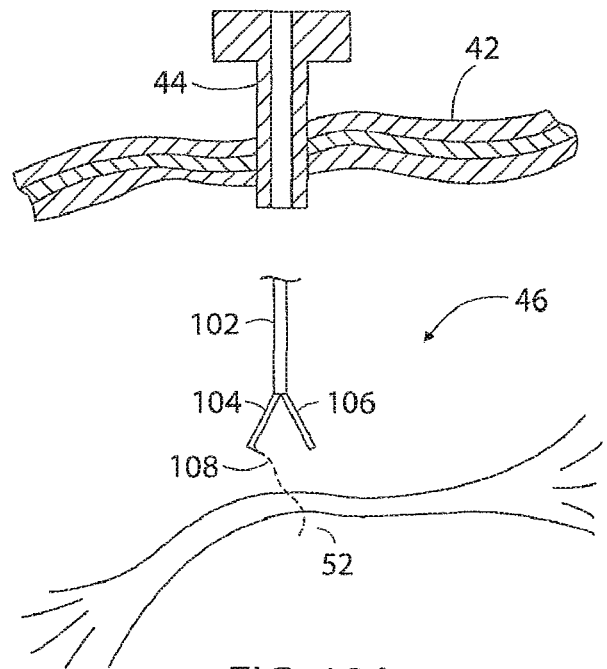
FIGS. 10A and 10B represent the insertion of a further embodiment of the apparatus into the abdominal cavity and the method of using the apparatus.
Figure 10B:
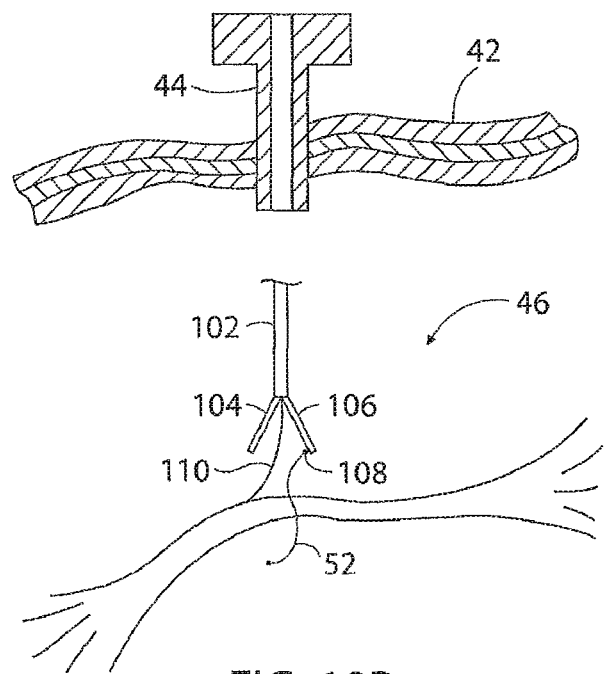

FIGS. 10A and 10B are a representation of the method of the invention practiced using an ENDO STITCH® device marketed by United States Surgical Corporation. FIG. 10A represents the distal end of the ENDO STITCH® 102 being inserted through the cannula 44 in the abdominal wall 42 to a position adjacent the diaphragm crus 52. As is conventional, the pair of jaws 104, 106 at the ENDO STITCH® distal end 102 hold a needle 108 and a length of suture 110. The ENDO STITCH® 102 is manually actuated to pass the needle 108 through the tissue 52 of the crus from one jaw 104 of the ENDO STITCH® to the opposite jaw 106 of the ENDO STITCH®. The length of suture 110 is then removed from the abdominal cavity 46 through the cannula 44 and is pulled tight, causing the length of suture 110 to move and hold the first internal organ away from the second internal organ in substantially the same manner as described earlier.

Figure 11A:
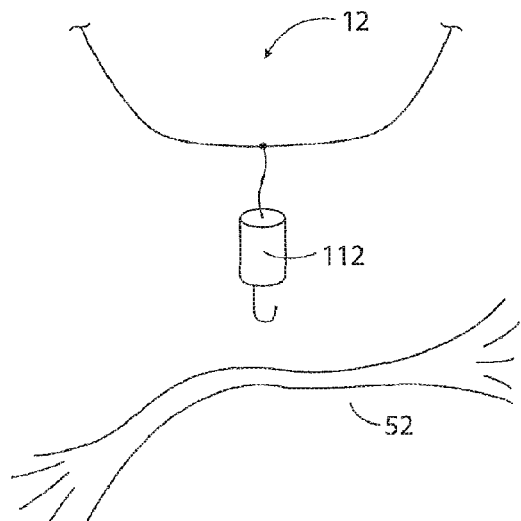
FIGS. 11A and 11B represent a further embodiment of the apparatus and its method of use.
Figure 11B:
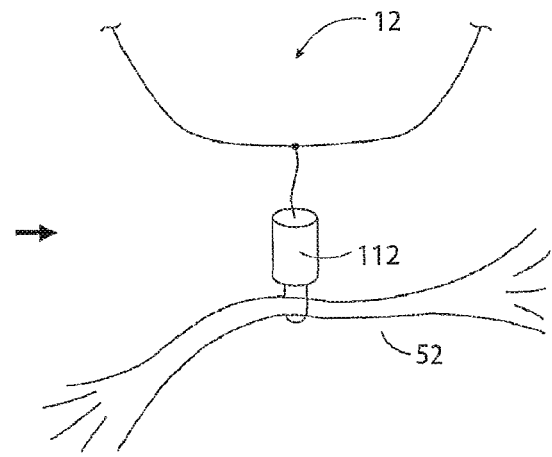

FIGS. 11A and 11B represent a further embodiment of the apparatus 12 and its method of use. The embodiment of the apparatus 12 shown in FIGS. 11A and 11B and its method of use are substantially the same as that of earlier-described embodiments, except that the T bar of the previously-described embodiments is replaced by a "J" hook locking clasp 112. FIG. 11A shows the locking clasp 112 in its open position prior to the hook portion of the clasp being passed through the tissue 52 of the diaphragm crus. FIG. 11B shows the locking clasp 112 after the hook of the clasp has been passed through the tissue 52 and the clasp has been locked. The method of further using the apparatus to move and hold an internal organ is substantially the same as that of earlier-described embodiments.

Figure 12A:
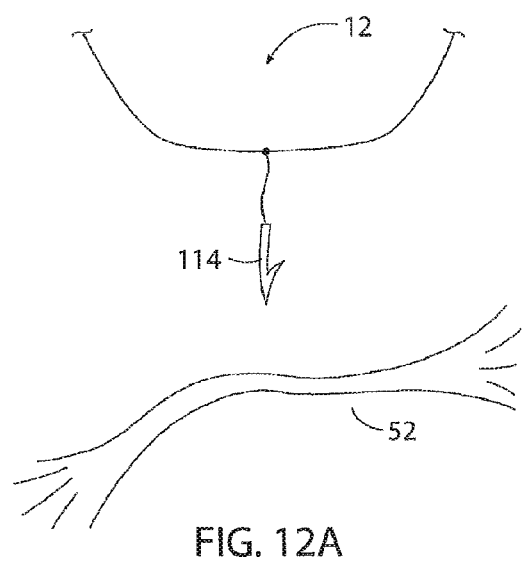
FIGS. 12A and 12B represent a further embodiment of the apparatus and its method of use.
Figure 12B:
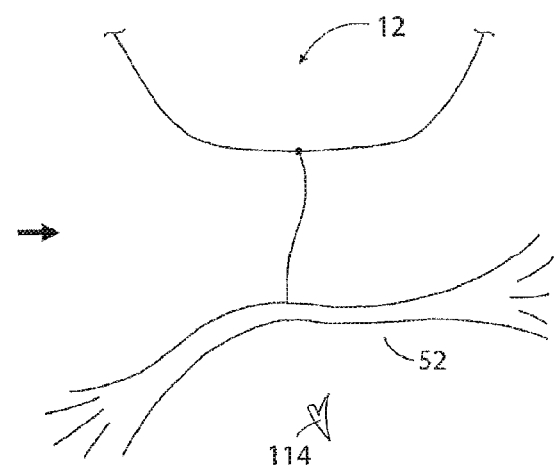

FIGS. 12A and 12B show a further embodiment of the apparatus 12 and its method of use. The construction of the embodiment of the apparatus 12 shown in FIGS. 12A and 12B is substantially the same as earlier described embodiments, except that the bar or locking clasp is replaced by a barbed needle 114. The method of using the embodiment of the apparatus shown in FIGS. 12A and 12B is substantially the same as that of earlier described embodiments, except that the barbed needle 114 is passed through the tissue 52 of the diaphragm crus until the barb of the needle emerges from the tissue as shown in FIG. 12B. This secures the apparatus to the tissue 52. Further use of the apparatus to move and hold an internal organ is substantially the same as that of earlier-described embodiments.

Figure 13A:
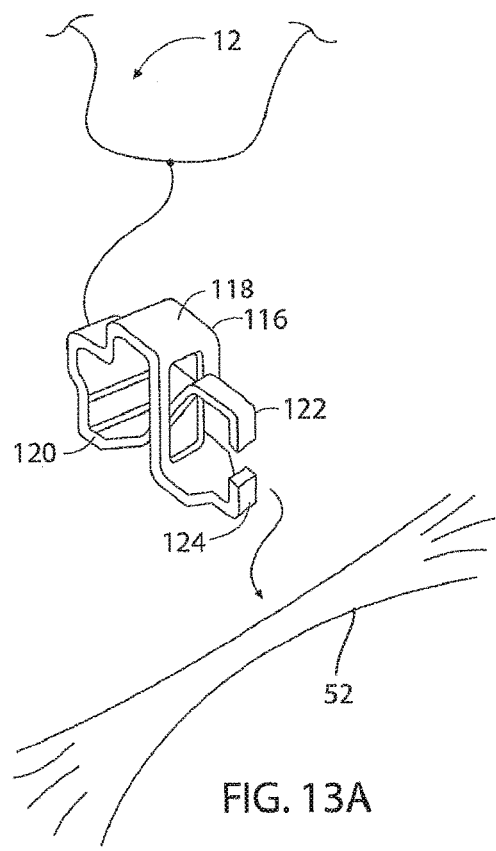
FIGS. 13A and 13B represent a further embodiment of the apparatus and its method of use.
Figure 13B:
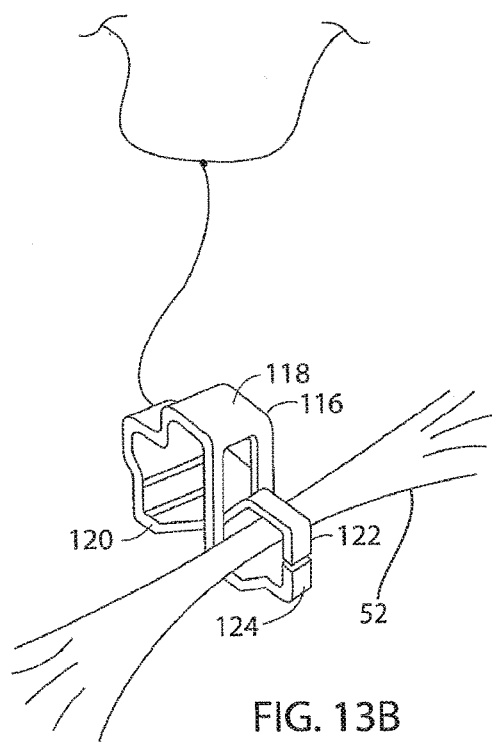

FIGS. 13A and 13B show a further embodiment of the apparatus 12 of the invention that is substantially the same as that as earlier-described embodiments except that the third tissue connector or T bar is replaced by a resilient biased clasp 116. In the method of using the apparatus of FIGS. 13A and 13B, the opposite arms 118, 120 of the clasp 16 are compressed to open the jaws 122, 124 of the clasp as shown in FIG. 13A. The jaws 122, 124 are then positioned around the tissue 52 of the diaphragm crus and are allowed to close, thereby securing the clasp 116 to the tissue 52. The subsequent method of using the apparatus shown in FIGS. 13A and 13B is substantially the same as that of previously-described embodiments of the apparatus.

Figure 14A:
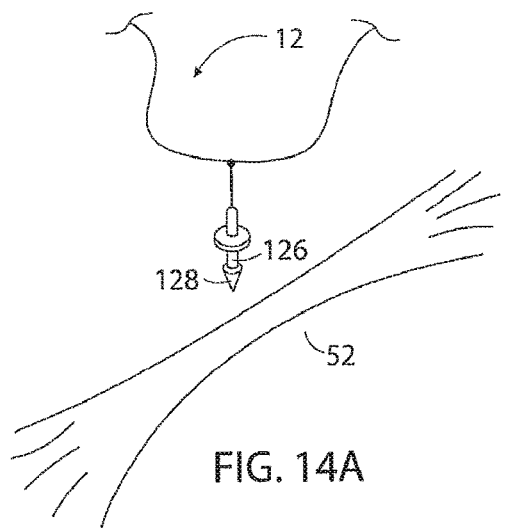
FIGS. 14A-14C represent a further embodiment of the apparatus and its method of use.
Figure 14B:
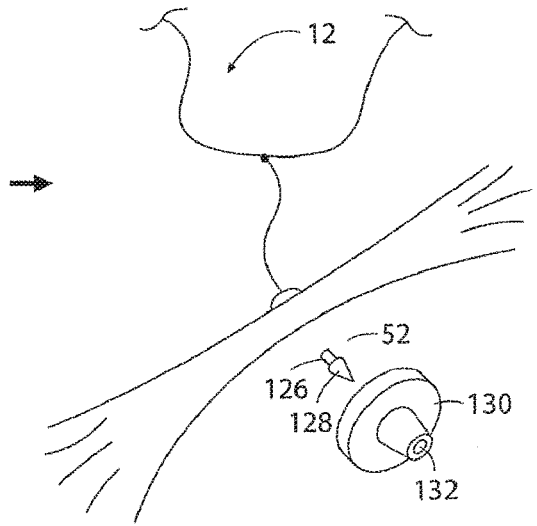
Figure 14C:
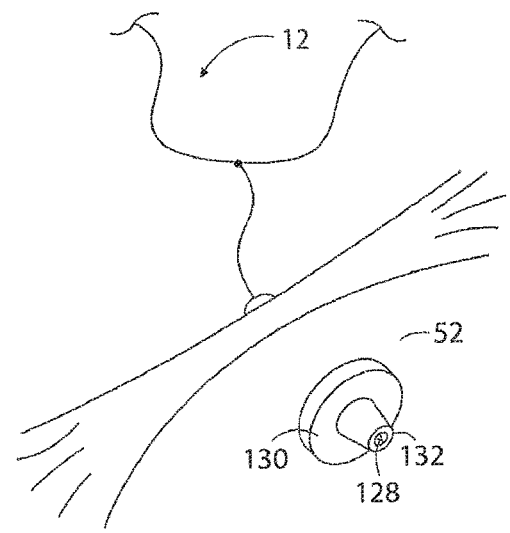

FIGS. 14A-14C show a further embodiment of the apparatus 12 that is substantially the same as that of previously-described embodiments except that the third tissue connector is a two-piece rivet assembly. The assembly is comprised of a pin 126 having an enlarged point 128 and a cap 130 having a circular center opening 132. In the method of using the apparatus of FIGS. 14A-14C, the pin 126 is first inserted through the tissue 52 of the diaphragm crus until the point 128 projects from the opposite side of the tissue. The point 128 is then inserted through the center opening 132 of the cap 130, thereby securing the pin 126 and the cap 130 to the tissue 152. The subsequent steps of using the apparatus of FIGS. 14A-14C is substantially the same as that of earlier-described embodiments of the apparatus.

Figure 15B:
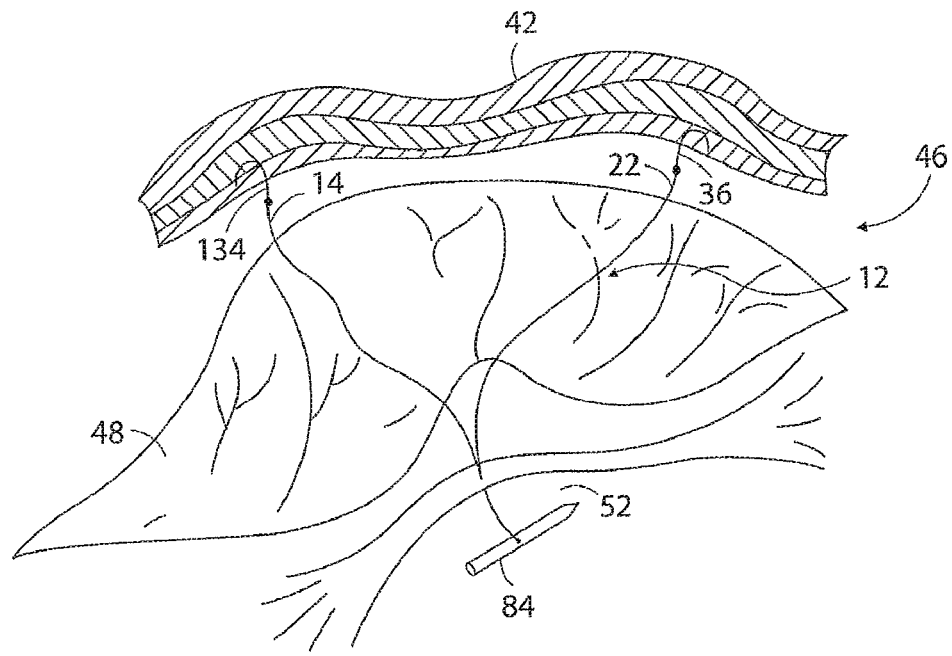
FIGS. 15A and 15B represent a further embodiment of the apparatus and its method of use.
Figure 15A:
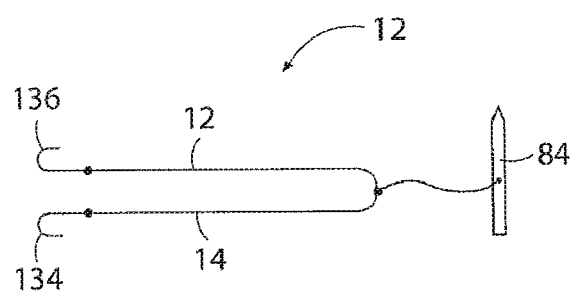

FIGS. 15A and 15B show a further embodiment of the apparatus 12 that has substantially the same construction of earlier-described embodiments of the apparatus except for the first and second tissue connectors being a pair of "J" shaped hooks 134, 136. In the method of using the embodiment of the apparatus shown in FIGS. 15A and 15B, the first cord segment 14 and the second cord segment 22 are secured to the inner abdominal wall 42 by passing the hooks 134, 136 through the tissue of the inner abdominal wall. Apart from this, the method of using the apparatus shown in FIGS. 15A and 15B is substantially the same as that of earlier-described embodiments of the apparatus.

Figure 16A:
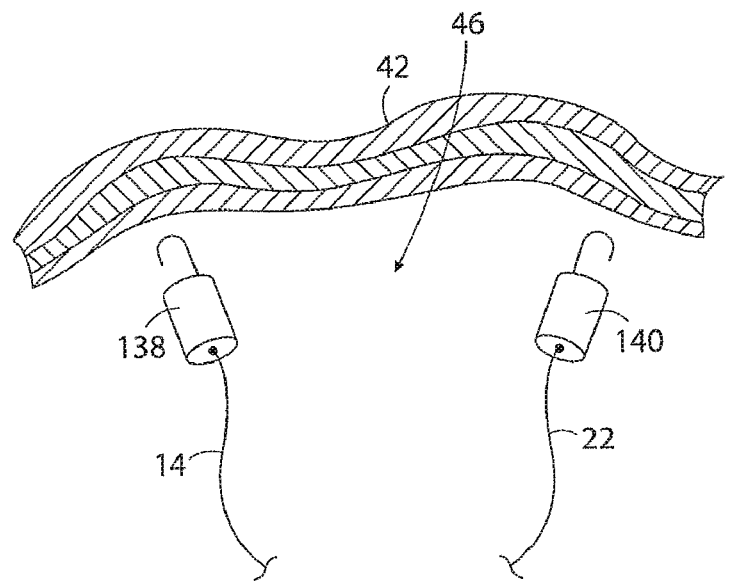
FIGS. 16A and 16B represent a further embodiment of the apparatus and its method of use.
Figure 16B:
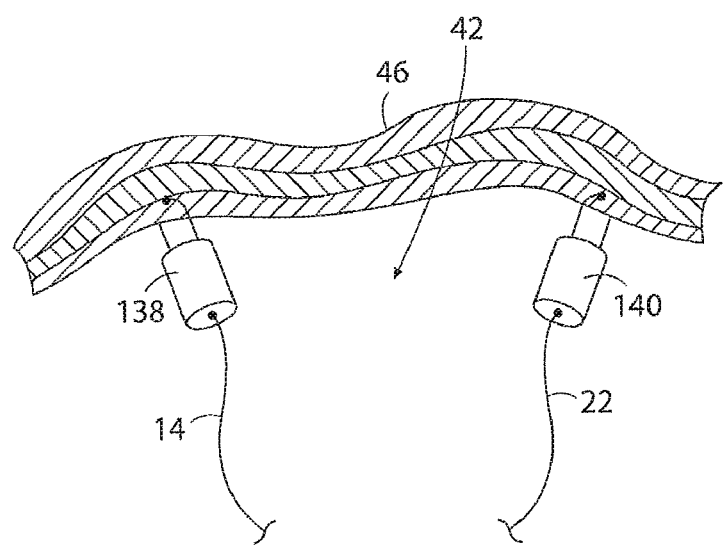

FIGS. 16A and 16B represent a further embodiment of the apparatus and its method of use that are substantially the same as that of previously-described embodiments, except for the first and second tissue connectors being a pair of "J" hook locking clasps 138, 140. In the method of using the apparatus of FIGS. 16A and 16B, the hook portions of the locking clasps 138, 140 are passed through the tissue of the inner abdominal wall 42 and then are locked closed. This secures the first cord segment 14 and the second cord segment 22 to the inner abdominal wall. Apart from this, the method of using the apparatus of the invention shown in FIGS. 16A and 16B is substantially the same as that of earlier-described embodiments of the apparatus.

Figure 17:
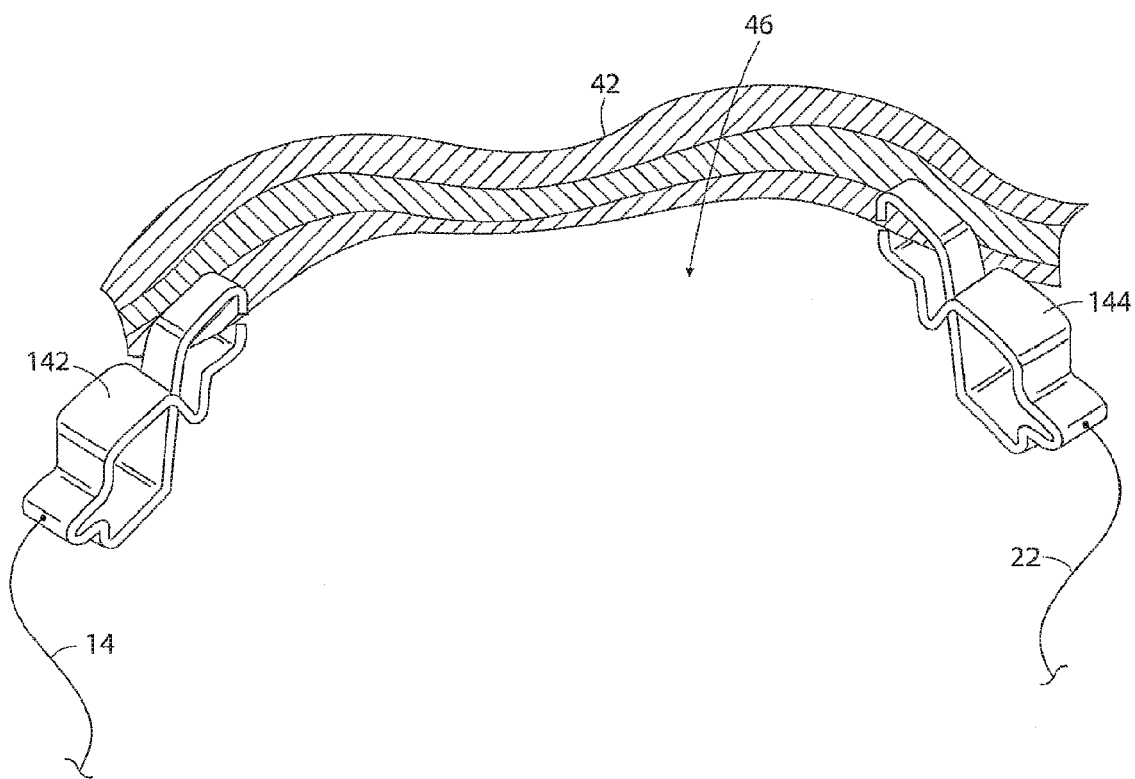
FIG. 17 represents a further embodiment of the apparatus and its method of use.

FIG. 17 shows a representation of an embodiment of the apparatus where the first and second tissue connectors are provided as a pair of resilient, biased clasps 142, 144 that have substantially the same construction of the earlier described clasp 116. The clasps 142, 144 are secured to the inner abdominal wall 42 by first opening the clasps and positioning tissue of the inner abdominal wall between the open jaws of the clasps, and then allowing the jaws of the clasps to close over the tissue. This secures the first cord segment 14 and the second cord segment 22 to the inner abdominal wall. Apart from this, the method of using the apparatus represented in FIG. 17 is substantially the same as that as earlier described embodiments of the apparatus.

Figure 18A:
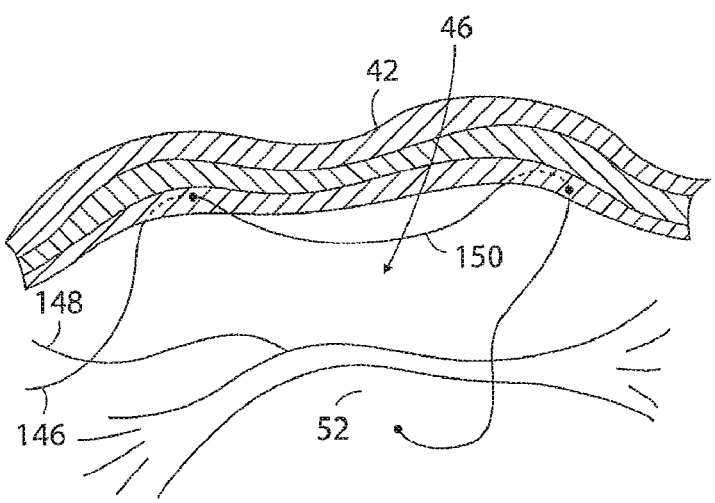
FIGS. 18A and 18B represent a further embodiment of the apparatus and its method of use.
Figure 18B:
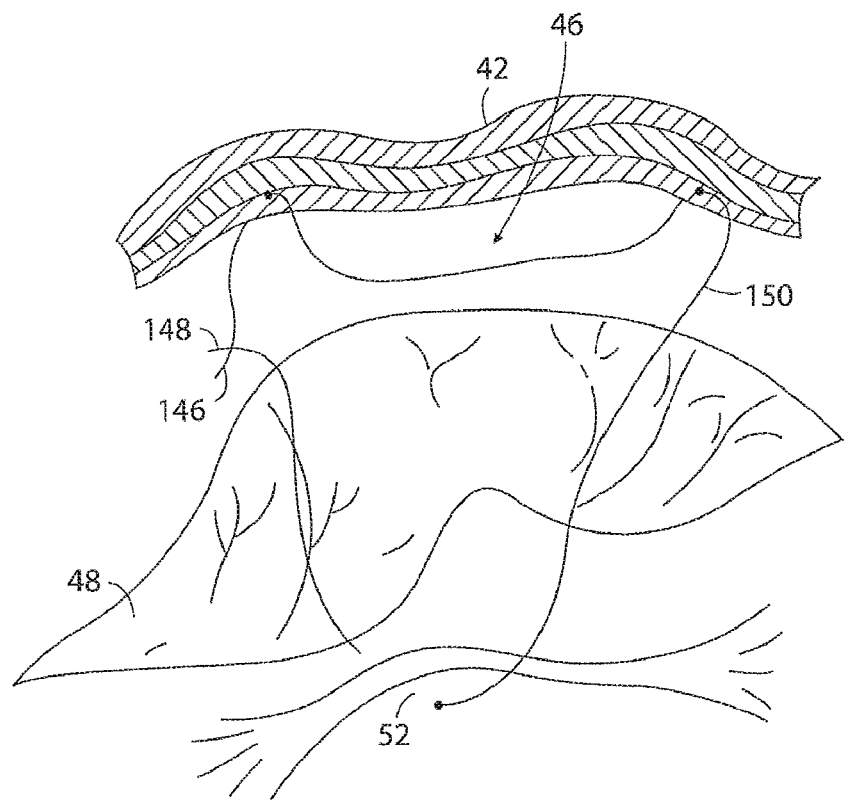

FIGS. 18A and 18B show an embodiment of the apparatus and its method of use that is substantially the same as that of FIG. 7. The embodiment of FIGS. 18A and 18B differs from that of the FIG. 7 embodiment in that the free ends 146, 148 of the length of suture 150 are tied in a knot completing the triangular loop configuration of the length of suture 150 at a location that is displaced from the portion of the suture 150 passed through the tissue 52 of the diaphragm crus. Apart from this, the method of using the apparatus of the invention shown in FIGS. 18A and 18B is substantially the same as that of the embodiment of the apparatus shown in FIG. 7.

Figures 19A, 19B:
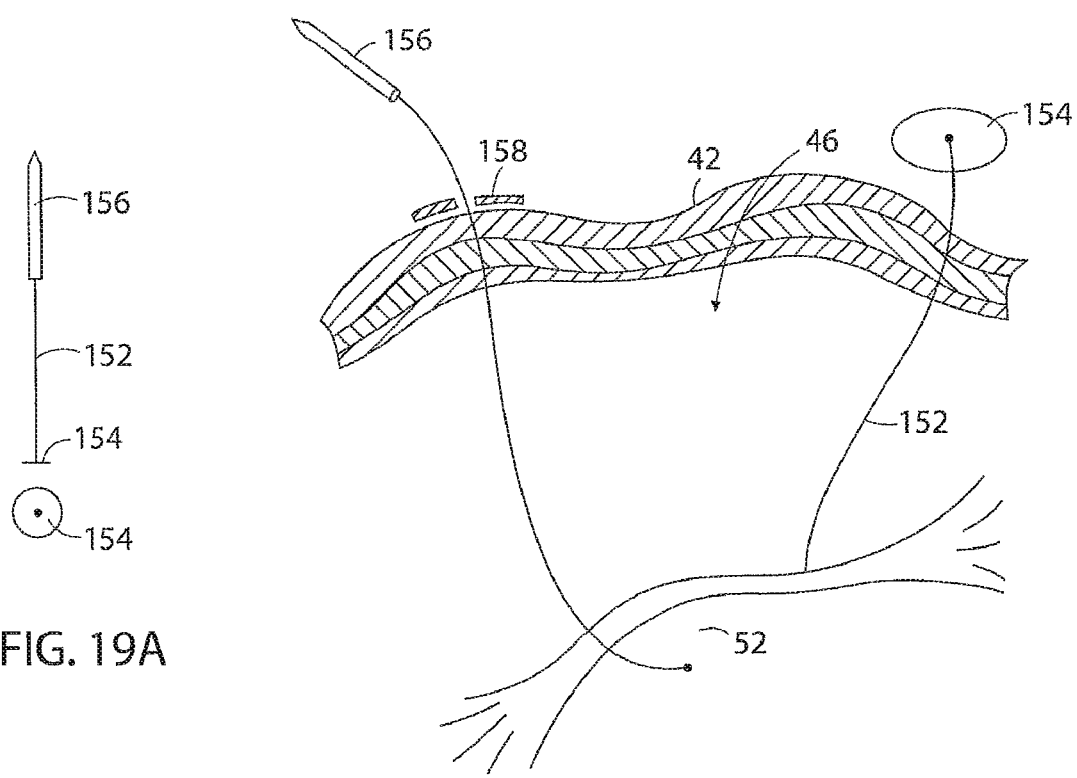
FIGS. 19A and 19B represent a further embodiment of the apparatus and its method of use.

FIGS. 19A and 19B show a further embodiment of the apparatus and its method of use. The apparatus shown in these drawing figures is comprised of a length of cord 152 with a circular pledget 154 secured at one end of the cord and a needle, for example a keith needle 156, secured to the opposite end of the cord. The cord 152 could be a length of suture or other similar material. In the method of using the apparatus shown in FIGS. 19A and 19B, the needle 156 is first passed through the abdominal wall 42 and into the abdominal cavity 46. The needle 156 is then passed through the tissue 52 of the diaphragm crus. The needle 156 is then again passed through the abdominal wall 42 to the exterior of the abdomen and is pulled tight. This results in the length of cord 152 engaging against and moving the first internal organ away from the second internal organ in substantially the same manner as previously-described embodiments. The tight length of cord 152 is then secured in place by a clasp 158 attached to the length of cord 152 against the exterior of the abdominal wall 42.

FIGS. 20A and 20B show a representation of a further embodiment of the apparatus and its method of use. In FIG. 20A, the apparatus is shown comprised of a length of cord 160 having a circular pledget 162 at one end and a needle, for example a keith needle 164, at the opposite end. The apparatus also includes a second shorter length of cord 166 with a T bar 168 at one end and a loop 170 formed in the opposite end. In the embodiment, the cords 160, 166 may be suture or other similar materials. The method of using the apparatus is represented in FIG. 20B. The T bar 168 is first secured to the tissue 52 of the diaphragm crus. The needle 164 is then passed through the tissue of the inner abdominal wall 42, through the loop 170 and then through the abdominal wall 42 to the exterior of the abdomen. Pulling the needle 164 on the exterior of the abdomen pulls the cord 160 tight across the internal organ to move and hold the internal organ in substantially the same manner as that of previously-described embodiments of the apparatus.

FIGS. 21A and 21B show a further embodiment of the apparatus that is substantially the same as that of the embodiment of FIGS. 20A and 20B, except that the needle 164 is removed from the end of the length of cord 160, leaving a free end 172 of the cord. The method of using this embodiment of the apparatus is substantially the same as that of the previously-described embodiment except for the step of passing the cord free end 172 through the abdominal wall 32. A GraNee needle (not shown) may be used to perform this step of the method.

FIGS. 22A and 22B show a further embodiment of the apparatus that is substantially the same as that of the previously-described embodiment, except that it is comprised of only the length of cord 160 having the circular pledget 162 at one end and a free end 172 of the cord at the opposite end. In the method of using this embodiment of the apparatus, the suture free end 172 is first passed through the inner abdominal wall 42, then through the tissue 52 of the diaphragm crus, and then through and out of the abdominal wall 42. As in the previously-described embodiment, the suture free end 172 can be passed through the tissue of the abdominal wall 42 and the crus 52 using a GraNee needle or other similar instrument. The length of cord 160 is pulled tight to move and hold the first internal organ relative to the second internal organ in substantially the same manner as previously-described method embodiments of the apparatus.

Figure 23:
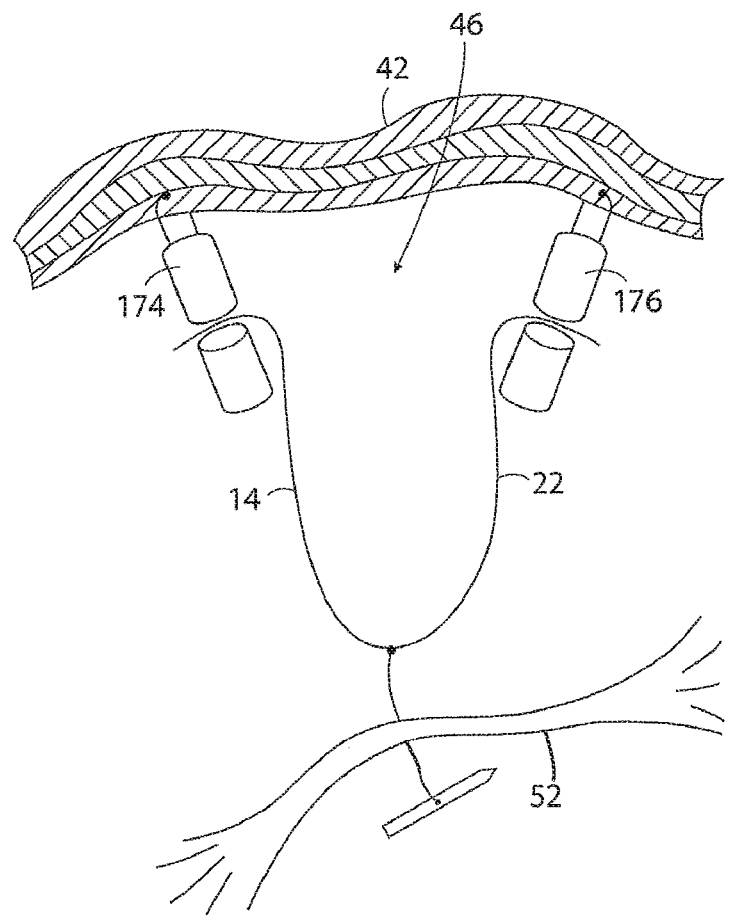
FIG. 23 represents a further embodiment of the apparatus and its method of use.

FIG. 23 shows a further embodiment of the apparatus that is substantially the same as that of earlier-described embodiments except for the first and second tissue connectors being "J" hook locking clasps 174, 176 that incorporate one-way clutch mechanisms. The ends of the cord segments 14, 22 can be pulled through the clutch mechanisms of the clasps 174, 176 in one direction, but are prevented by the clutch mechanisms from being pulled through the clasps 174, 176 in the opposite directions.

Figure 24A:
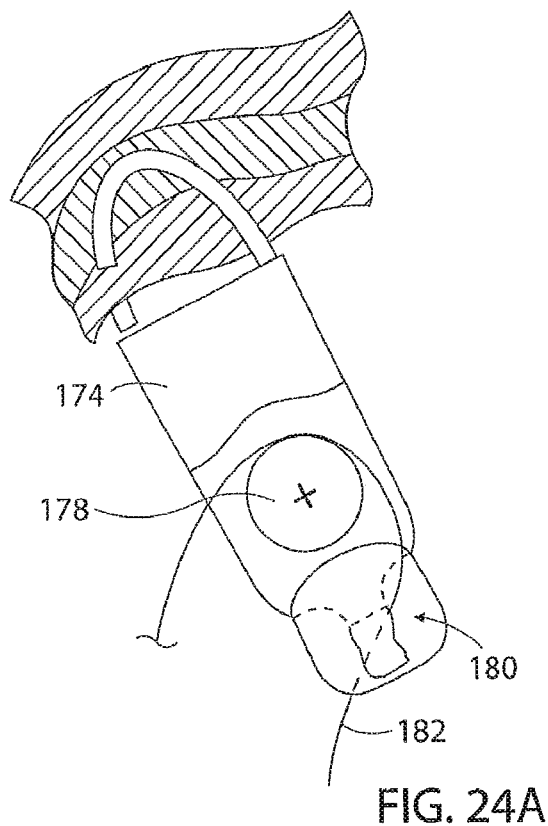
FIGS. 24A-24C represent component parts of a further embodiment of the apparatus.
Figure 24B:
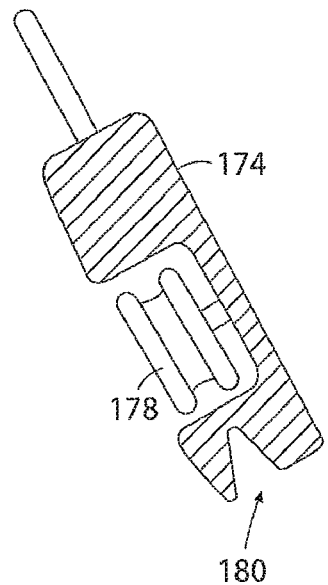
Figure 24C:
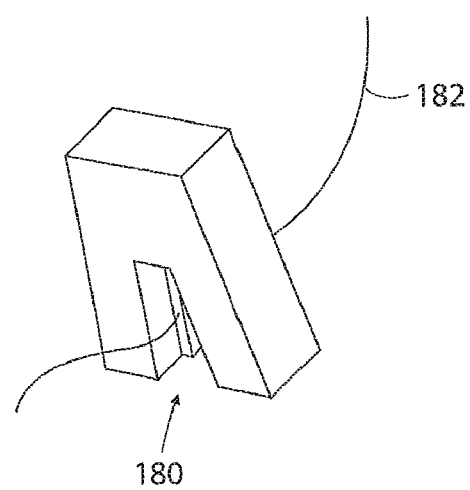

FIGS. 24A-24C show representations of a "J" hook locking clasp such as that shown in FIG. 23, with a one-way clutch mechanism. The one-way clutch mechanism is comprised of a rotatable pulley 178 and a "V" shaped groove 180 positioned adjacent the pulley 178. An end portion of the cord 182 is threaded through the "V" shaped groove 180 and then around the pulley 178. When the end of the cord 182 extending from the pulley 178 is pulled tight, the relative positions of the pulley 178 and the groove 180 cause the portion of the cord 182 to wedge and become locked in the bottom of the groove 180.

Figure 25:
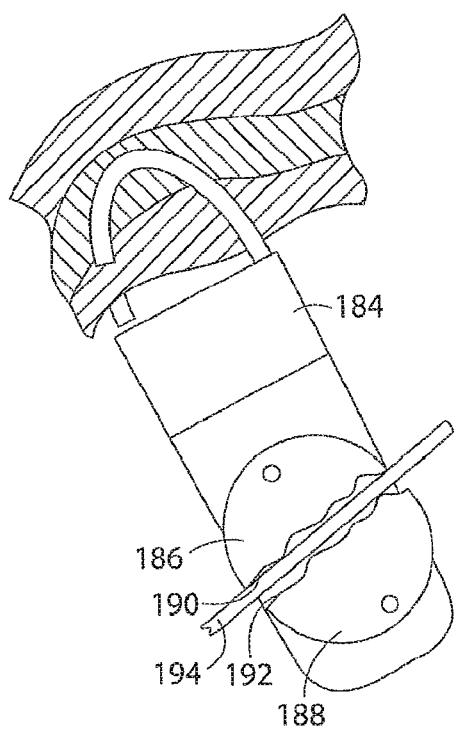
FIG. 25 represents a component part of a further embodiment of the apparatus.

FIG. 25 shows a further representation of the embodiment of the apparatus employing a "J" hook locking clasp 184 with a one-way clutch mechanism. The one-way clutch mechanism is comprised of a pair of pivoting cams 186, 188 having opposing ratchet tooth surfaces 190, 192. A portion of the apparatus cord 194 is threaded between the opposed tooth surfaces. The portion of cord 194 can be pulled through the spacing between the cam ratchet tooth surfaces 190, 192 in one direction, for example to the left in FIG. 25, but the cams 186, 188 pivot toward each other and their ratchet tooth surfaces 190, 192 clamp the cord portion 194 between the surfaces when the cord portion is pulled in the opposite direction, for example to the right as shown in FIG. 25.

Figure 26:
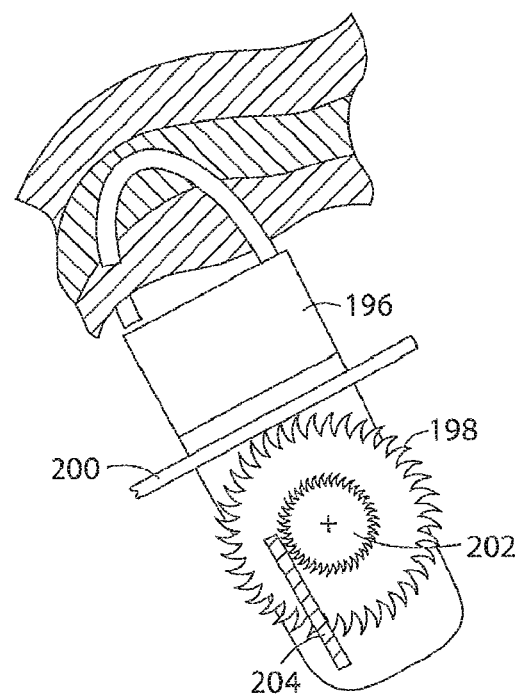
FIG. 26 represents a component part of a further embodiment of the apparatus.

FIG. 26 shows a representation of a further embodiment of the "J" hook clasp 196 having a one-way clutch mechanism. In this embodiment, the one-way clutch mechanism is comprised of a toothed wheel 198 that engages with the cord portion 20 pulled through the claps 196. The tooth wheel 198 also has a smaller ratchet wheel 202 at its center. The ratchet wheel 202 engages against a resilient pawl 204. The ratchet wheel 202 and resilient pawl 204 function in the conventional manner allowing the toothed wheel 198 to rotate in one direction n when the cord portion 200 is pulled through the clutch mechanism, for example to the right as shown in FIG. 26, but prevent the rotation of the toothed wheel 198 and the movement of the cord portion 200 when the cord portion is pulled in the ' opposite direction, for example to the left as shown in FIG. 26.

Figure 27:
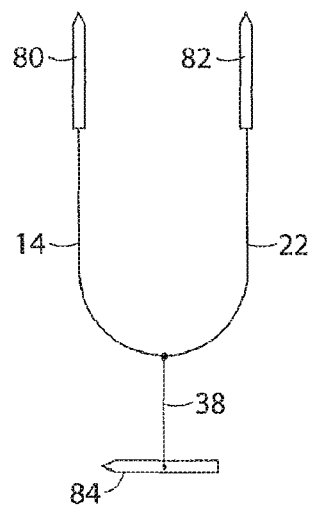
FIG. 27 represents represent a further embodiment of the apparatus.

FIGS. 27-32 show several different representations of the possible constructions of the cord segments 14, 22, 38 of the apparatus of the invention. In FIGS. 27-32 the first and second tissue connectors are represented by needles, for example keith needles 80, 82. The third tissue connector is represented by a T bar 84. It should be understood that these are only examples of only three tissue connectors that could possibly be used with the apparatus of the invention, and that other forms of tissue connectors, for example the types described herein could be used as the three tissue connectors on the apparatus. FIG. 27 shows the first 14, second 22 and third 38 cord segments as being constructed of suture material.

Figure 28:
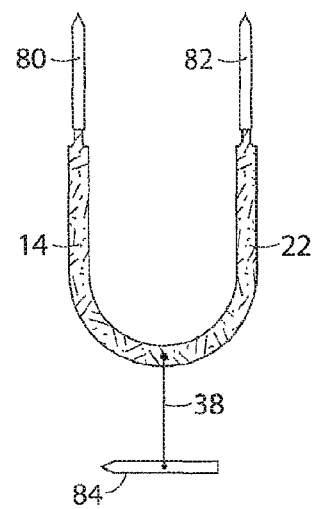
FIG. 28 represents represent a further embodiment of the apparatus.

FIG. 28 shows the first 14 and second 22 cord segments being part of a single length of surgical tape or strap, and the third cord segment 38 being constructed of suture.

Figure 29:
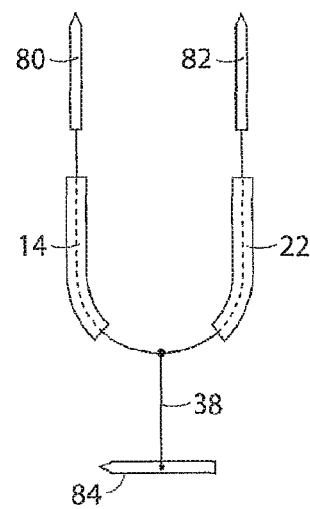
FIG. 29 represents a further embodiment of the apparatus.

FIG. 29 shows the first 14 and second 22 cord segments being constructed of lengths of suture inserted through lengths of surgical tubing. The third cord segment 38 is constructed of suture.

Figure 30:
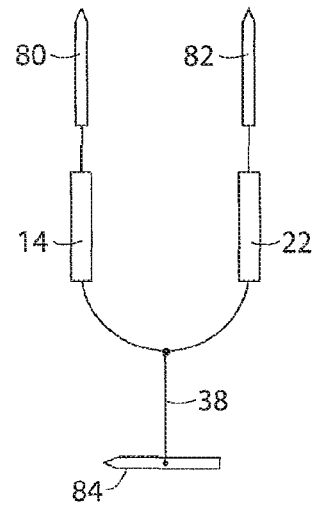
FIG. 30 represents a further embodiment of the apparatus.

FIG. 30 shows the apparatus as having first 14 and second 22 cord segments constructed of combinations of surgical tape and suture connected end to end. The third cord segment 38 is constructed of suture material.

Figure 31:
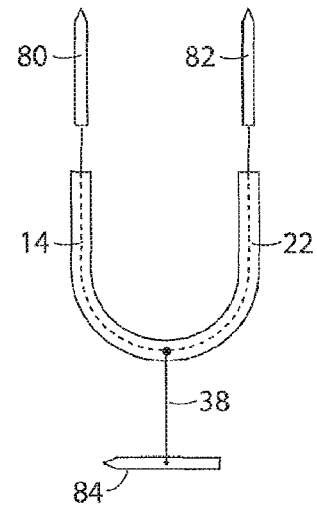
FIG. 31 represents a further embodiment of the apparatus.

FIG. 31 shows the apparatus being constructed of first 14 and second 22 cord segments formed from a single length of suture material inserted through a single length of surgical tubing. The third cord segment 38 is constructed of suture material.

Figure 32:
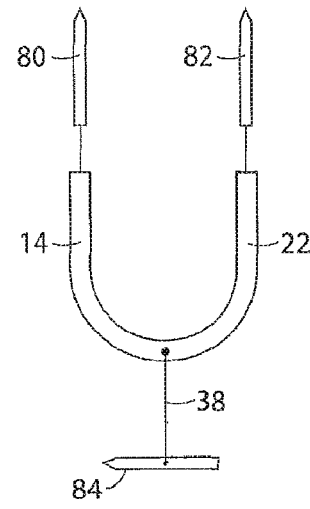
FIG. 32 represents a further embodiment of the apparatus.

FIG. 32 shows the apparatus as having the first 14 and second 22 cord segments constructed of a single continuous length of surgical tape having lengths of suture at opposite ends. The third cord segment 38 is constructed of suture material.

FIGS. 33-45 show examples of some of the various different types of tissue connectors that could be used as anyone of the tissues connectors 32, 34, 36 of the apparatus. These are only some of the possible types of tissue connectors, and the connectors shown in FIGS. 33-45 should not be interpreted as limiting the apparatus to the particular tissue connectors shown.

Figure 33:
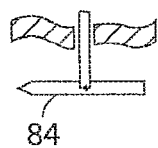
FIG. 33 represents a component part of an embodiment of the apparatus.

FIG. 33 shows a T bar 84 as one example of anyone of the three tissue connectors 32, 34, 36.

Figure 34:
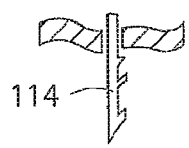
FIG. 34 represents a component part of an embodiment of the apparatus.

FIG. 34 shows a barbed needle 114 as anyone of the three tissue connectors 32, 34, 36.

Figure 35:
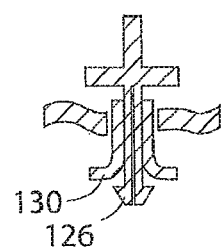
FIG. 35 represents a component part of an embodiment of the apparatus.

FIG. 35 shows the two-piece rivet pin 126 and cap 130 connector that can be used as anyone of the three tissue connectors 32, 34, 36.

Figure 36:
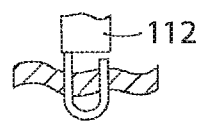
FIG. 36 represents a component part of an embodiment of the apparatus.

FIG. 36 shows the "j" hook locking clasp 112 that can be used as anyone of the three tissue connectors 32, 34, 36.

Figure 37:
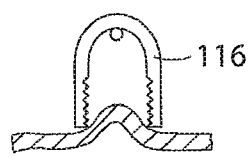
FIG. 37 represents a component part of an embodiment of the apparatus.

FIG. 37 shows the resilient, biased clasp 116 that could be used as any one of the three tissue connectors 32, 34, 36.

Figure 38:
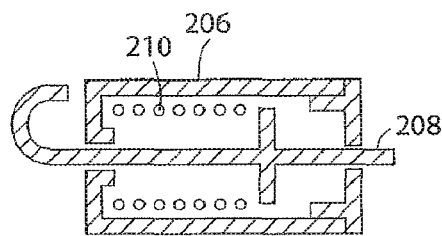
FIG. 38 represents a component part of an embodiment of the apparatus.

FIG. 38 shows a cross-section of an embodiment of a "j" hook locking clasp. The embodiment shown is comprised of a cylindrical housing 206 that contains the "j" hook 208 and a coil spring 210 that biases the "j" hook 208 to its closed position.

Figure 39A:
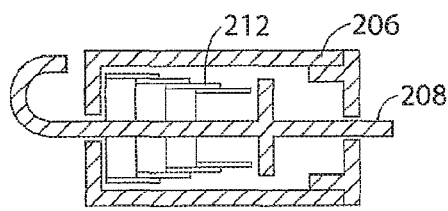
FIGS. 39A-39C represent component parts of an embodiment of the apparatus.
Figure 39B:
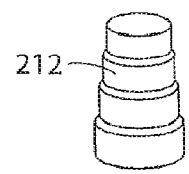
Figure 39C:
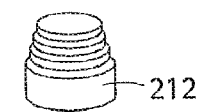

FIGS. 39A-39C show a variation of the "j" hook locking clasp of FIG. 38 where the coil spring 210 is replaced by a spiral band spring 212. FIG. 39B shows the spiral and spring 212 in its extended configuration, and FIG. 39C shows the spring in its compressed configuration.

Figure 40B:
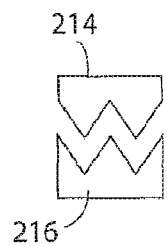
FIGS. 40A and 40B represent component parts of an embodiment of the apparatus.
Figure 40A:
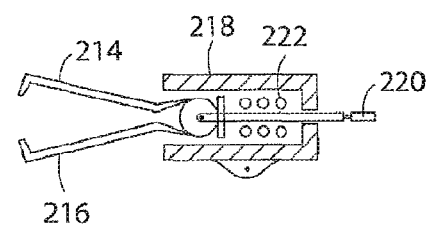

FIGS. 40A and 40B show a tissue connector clasp that is comprised of a pair of resilient jaws 214, 216 that project from one end of a hollow housing 218, and a pin 220 connected to the jaws that projects from the opposite end of the housing. A spring 22 contained in the housing 218 biases the pin 220 and the jaws 214, 216 to the left as shown in FIG. 40A. This causes the resilient jaws to move to their open position shown in FIG. 40A. Pulling the pin 220 to the right against the bias of the spring 222 causes the housing to slide against the opposite sides of the jaws 214, 216 and move the jaws to their closed position.

Figure 41:
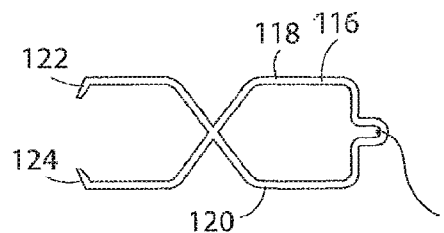
FIG. 41 represents a component part of an embodiment of the apparatus.

FIG. 41 shows a side view of the resilient biased clasp 116 described earlier. Compressing the opposite arms 118, 120 of the clasp 116 causes the jaws 122, 124 to separate. Releasing the compression force causes the jaws 122, 124 to move together under the bias of the resilience of the clasp 116.

Figure 42:
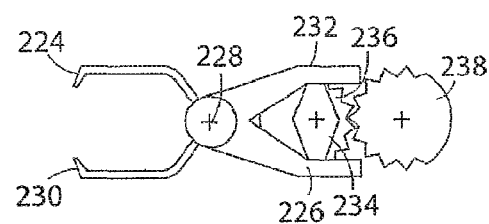
FIG. 42 represents a component part of an embodiment of the apparatus.

FIG. 42 shows an embodiment of a clasp comprised of a first jaw 224 and first arm 226 connected by a pivot connection 228 to a second jaw 230 and second arm 232. An oblong cam 234 on a toothed cam wheel 236 is positioned between the pair of arms 226, 232. A toothed actuator wheel 238 meshes with the toothed cam wheel 236. Rotation of the actuator wheel 238 will cause rotation of the cam wheel 236 and the cam 238. Rotation of the cam 234 to its position shown in FIG. 42 pushes the pair of arms 226, 232 away from each other which in turn causes the pair of jaws 224,230 to move toward each other. Rotation of the cam 234 90° or one-quarter turn from its position shown in FIG. 2 will cause the jaws 242, 230 to move away from each other.

Figure 43:
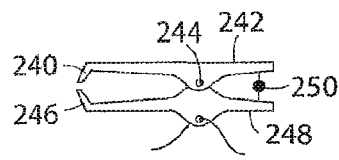
FIG. 43 represents a component part of an embodiment of the apparatus.

FIG. 43 shows an embodiment of a clasp comprised of a first jaw 240 and first arm 242 connected by a pivot connection 244 to a second jaw 246 and second arm 248. A spring 250 is positioned between the pair of arms 240, 248 and biases the arms away from each other. This in turn biases the first jaw 242 and second jaw 246 toward each other. The jaws 242, 246 are opened by applying a compression force to the opposite sides of the first arm 240 and second arm 248 that compresses the spring 250.

FIGS. 44A-44B show a side-sectioned view of a construction of the rivet assembly described earlier. As seen in the drawing figures, the pin head 128 is slightly larger in diameter than the cap hole 132. When the pin 126 is attached to the cap 130, there is a fixed gap or maximum distance between a circular head 252 of the pin 126 and the cap 130.

FIGS. 45A-45E show a further embodiment of a rivet assembly. In this assembly, the rivet pin 254 has several notches 256 along its length between the pin head 258 and the pin point 260. The rivet cap 262 is similar in construction to that of the previously-described embodiment with a center opening or hole 264 extending through the cap. However, the cap 262 is also formed with a transverse slot 266 that intersects the center hole 264 and a parallel slot 268 that extends into the cap 262 parallel to the center hole 264 and intersects the transverse slot 266. A locking tab 270 with a pin hole 272 and a spring hole 274 is inserted in the transverse slot 266 for sliding movement therein. A resilient wire spring 276 is inserted downwardly into the parallel slot 268 and through the tab pin hole 272. Inserting the rivet pin 254 into the cap center hole 264 and through the tab pin hole 272 causes the pin to slide the 30 tab to the left as shown in FIG. 45A against the bias of the wire spring 276. As a pin notch 256 passes through the tab hole 272, the bias of the spring 276 causes the tab 270 to move to the right and into the notch 256. This locks the pin 254 in place relative to the cap 262. With the pin 254 having a number of notches, and in the example of FIG. 45A having three notches, the position of the pin head 258 relative to the cap 262 can be adjusted between three positions. This provides an adjustable gap or an adjustable distance between the pin head 258 and the cap 262.

Figure 46A:
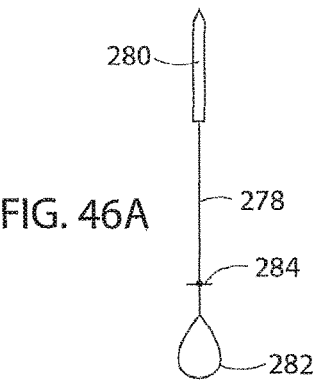
FIGS. 46A-46E represent component parts of an embodiment of the apparatus and its method of use.
Figure 46B:
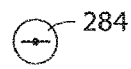
Figure 46C:
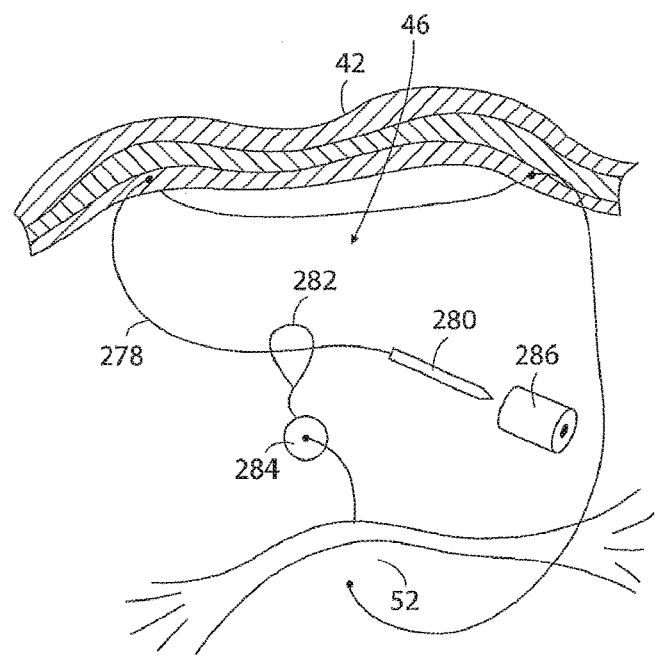
Figure 46D:
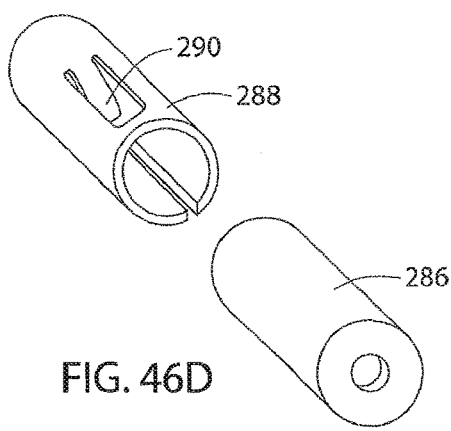
Figure 46E:
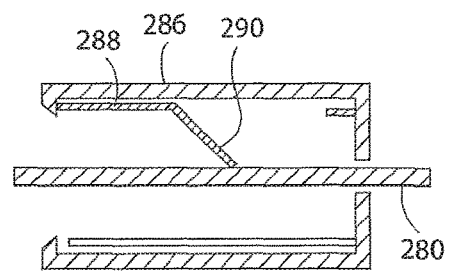

FIGS. 46A-46E represent a further embodiment of the apparatus of the invention. This embodiment is comprised of a length of cord 278 having a needle 280 at one end and a loop 282 formed at the opposite end. A circular pledget 284 is provided on the length of cord 278 toward the loop end of the cord. The apparatus also includes a locking collar having a hollow cylindrical housing 286 that contains a tubular one-way suture lock 288. The suture lock 288 is basically cylindrical but is formed with a resilient tab 290 that projects toward the center of the cylindrical configuration of the suture lock. FIG. 46E shows a cross-section representation of the collar cylindrical housing 286 containing the one-way suture lock 288 and a portion of the length of cord 278 extending through the collar. The method of using this embodiment of the apparatus is shown in FIG. 46C. In use in the abdominal cavity 46, the needle 280 is first passed through the tissue 52 in the area of the diaphragm crus, and then is passed a first time through the inner abdominal wall 42. The needle 280 is then moved across the inner abdominal wall 42 and is again passed a second time through the inner abdominal wall. The needle is then inserted through the loop 282 and is pulled tight. This causes the length of cord 278 to form a triangular loop in the abdominal cavity that moves the first internal organ away from the second internal organ and holds the first internal organ in the displaced position in the same manner as previously-described methods of using the apparatus of the invention. The needle 280 is then passed through the collar cylindrical housing 286 and the housing 286 is moved tight against the cord loop 282. The cord loop 282 is smaller than the housing 286 so that the housing cannot pass through the loop 282. As the length of cord 278 is pulled through the collar housing 286, the locking tab 290 engages against the side of the cord 278 as shown in FIG. 46E. This allows the cord 278 to move through the collar housing 286 in the direction to the right shown in FIG. 46E, but prevents movement of the cord to the left as shown in the figure. In this manner, the apparatus of FIGS. 46A-46E holds the length of cord tight in its triangular loop configuration.

Figure 47A:
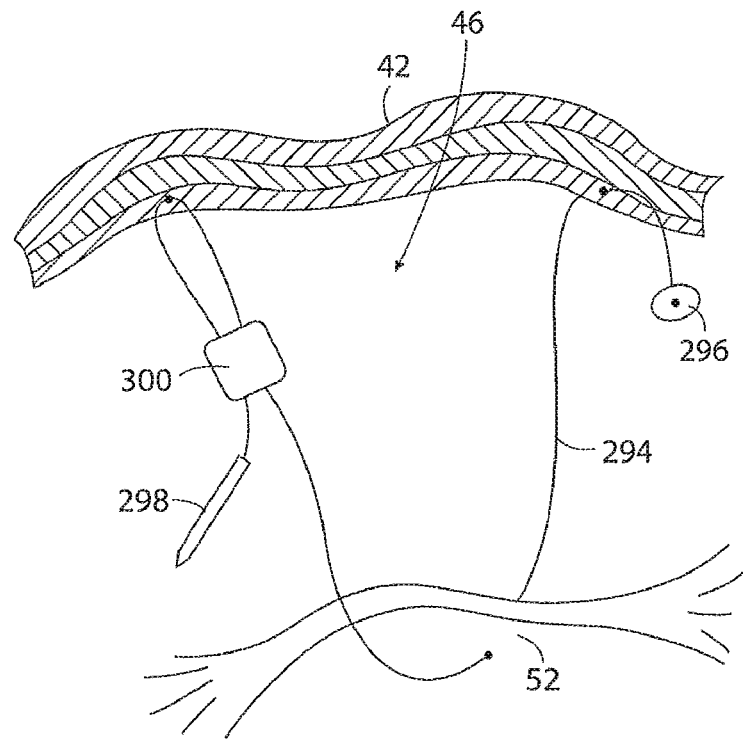
Figure 47B:
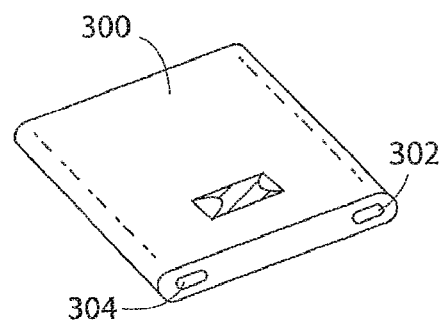

FIGS. 47A and 47B show a further embodiment of the apparatus of the invention and its method of use. The apparatus is comprised of a length of cord 294 having a pledget 296 secured at one end and a needle 298 secured at the opposite end. The apparatus also includes a one-way locking mechanism 300 having a pair of channels 302, 304 through the mechanism dimensioned to receive the length of cord 294. One of the channels 302 allows the length of cord 294 to move through the channel in one direction, but prevents the opposite direction of movement. The other channel 304 allows the length of cord 294 to move through the channel in one direction, but also prevents the opposite direction of movement of the cord 294. As represented in FIG. 47A, the method of using the apparatus first involves the needle 298 passing through the inner abdominal wall until the pledget 296 is positioned up against the wall. The needle 298 then passes through the tissue 52 in the area of the diaphragm crus. The needle 298 is then inserted through the first channel 302 of the one-way locking mechanism 300. The needle 298 is then again passed through the inner abdominal wall at a location spaced from the first insertion site and is then passed through the second channel 304 of the one-way locking mechanism 300. The needle 298 with the length of cord 294 are then pulled tight and the locking mechanism 300 is moved up against the inner abdominal wall at the second needle insertion site. This causes the length of cord 294 to move the first internal organ and hold the first internal organ in its moved position away from the second internal organ in a similar manner to that of earlier-described embodiments.

FIGS. 47C and 47D show the interior of one embodiment of the one-way locking mechanism 300. The mechanism 300 includes a housing first half 306 and a second half 308 that are connected together by a living hinge 310. The open position of the locking mechanism is shown in FIG. 47D. The interior of the two halves 306,308 of the locking mechanism are formed with grooves 312,314 that form the two channels 302,304 through the locking mechanism when the two halves 306, 308 of the locking mechanism are pivoted about the living hinge 310 and snapped together. A "U" shaped spring member 316 is positioned in the first locking mechanism half 306. The spring member 316 has a pair of arms 318,320 that project from opposite sides of the spring member. Each arm 318, 320 in turn has a resilient locking tab 322, 324 that projects outwardly at an angle from its respective arm 318, 320. The resilient tabs 322, 324 are positioned to engage in sliding engagement along portions of the cord 294 that pass through the channels 302, 304. As shown in FIG. 47D, the one tab 322 will allow the cord 294 to slide across the tab in a direction from right to left as shown in the drawing figure, but will prevent the reverse sliding movement of the cord. The other tab 324 will allow sliding movement of the cord 294 across the tab 324 in a left to right direction as shown in FIG. 47D, but will prevent the reverse movement of the length of cord 294.

FIGS. 48A-48D show a variant embodiment of the one-way locking mechanism 300. As shown in FIG. 48A, the length of cord is passed through the locking mechanism 328 in much the same manner as the earlier-described locking mechanism 300. However, the second channel 330 of the locking mechanism 328 of FIG. 48A has a block 332 with a hole 334 positioned along the channel. An inclined tooth 336 is positioned in the block hole 334. The portion of the cord length 338 that extends through the locking mechanism channel 330 also extends through the block hole 334. A spring 340 in the locking mechanism 328 biases the block 332 and the tooth 336 toward the portion of cord 338 extending through the locking mechanism channel 330. Due to the inclination of the tooth 336, with the spring 340 biasing the tooth 336 into engagement with the cord portion 338, the cord portion 338 can slide over the tooth 336 as it is moved in a left to right direction as shown in FIG. 48C, but is prevented from moving in the opposite direction. Pressing the block 332 into the locking mechanism 328 against the bias of the spring 340 disengages the tooth 336 from the cord portion 338 and permits the cord portion to move in either direction through the locking mechanism 328.

FIGS. 49A and 49B show a further embodiment of a cord locking mechanism 344 that is similar to that of FIG. 48A. A cross-section of a channel 346 extending through the locking mechanism 344 is shown in FIG. 49A. The channel 346 is formed with pairs of ridges 348, 350 on opposite sides of the channel. A wave form spring 352 is positioned in the channel 346. The spring 352 has grooves 354 formed through peaks formed in the wave form spring. The portion of the cord 356 passing through the locking mechanism channel 346 also passes through the grooves 354 in the wave form spring 352. A button hole 358 is provided in the top of the cord locking mechanism 344 and a release button 360 is positioned in the hole. When the release button 360 is pressed in the hole 358, it engages with the wave form spring 352 and compresses the spring to the position shown in FIG. 49A. In this position of the spring 352 the cord 356 is free to move in opposite directions through the locking mechanism 344. When the button 360 is released, the spring 352 moves upwardly from its position shown in FIG. 49A and portions of the spring 362 engage with the cord portion 356 extending through the lock mechanism channel 346 and hold the cord portion against the ridges 348 at the top of the channel 346. This locks the cord portion 356 in the locking mechanism 344.

Figure 50A:
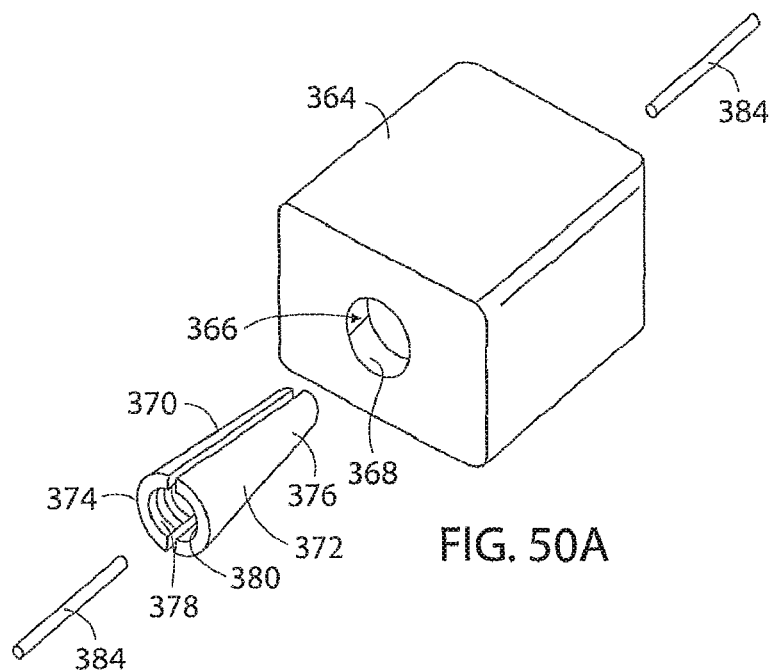
FIGS. 50A and 50B represent component parts of an embodiment of the apparatus and its method of use.
Figure 50B:
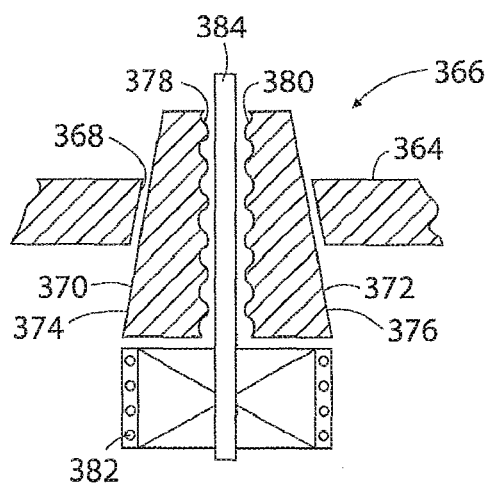

FIGS. 50A and 50B show a further embodiment of a one-way cord locking mechanism. The mechanism includes a housing 364 having a hole 366 extending through the housing that is defined by a cone-shaped interior surface 368. A pair of lock members 370,372 are positioned in the housing hole 366. Each of the lock members 370, 372 have exterior surfaces 374,376 that when the locking members are positioned together, define a truncated cone shape that fits within the cone-shaped interior surface 368 of the housing 364. The opposing interior surfaces 378, 380 of the lock members 370, 372 are formed with mating peaks and valleys. As shown in FIG. 50B, a spring 382 biases the two lock members 370, 372 into the cone-shaped interior surface 368 of the housing 364, thereby causing the lock member interior surfaces 378, 380 to move toward each other. A portion of a cord length 384 extending through the opposing interior surfaces 378, 380 of the lock members 370, 372 is prevented from moving in the upward direction as shown in FIG. 50B due to the bias of the spring 382. However, when the cord portion 384 is moved in the opposite downward direction as shown in FIG. 50B, the movement of the cord portion 384 causes the lock members 370, 372 to compress the spring 382. This allows the lock member interior surfaces 378, 380 to move away from each other and release the portion of the cord 384 for movement through the lock mechanism.

FIGS. 51A-51E show one method of inserting the apparatus of the invention into the tubular insertion device 86 described earlier. As shown in these drawing figures, a length of suture 386 is looped around the apparatus and is then pulled through the interior of the insertion device 86. The first 14 and second 22 cord segments are folded flat against each other and the additional cord segment 38 is folded over parallel with the first cord segment 14 and second cord segment 22. The apparatus is then pulled by the suture loop 386 into the interior of the insertion device 86 to the position shown in FIG. 51E.

Figure 52A:
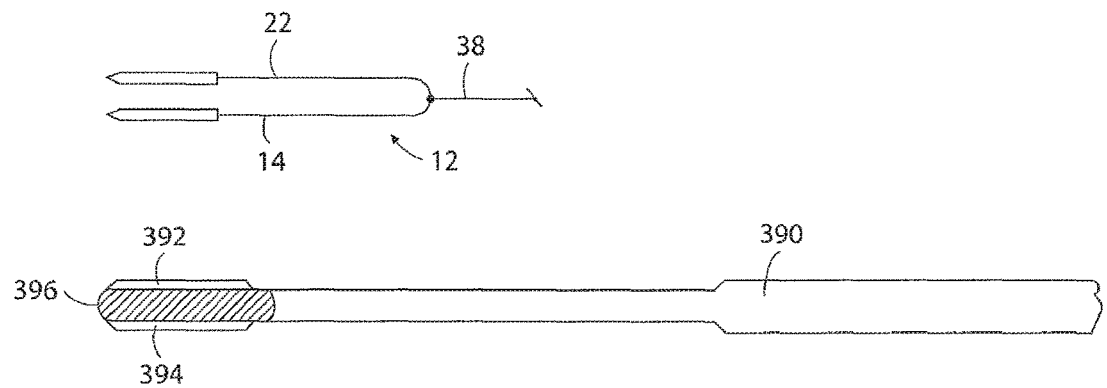
FIGS. 52A and 52B represent embodiments of the apparatus and an insertion device and the method of mounting the apparatus on the insertion device.
Figure 52B:
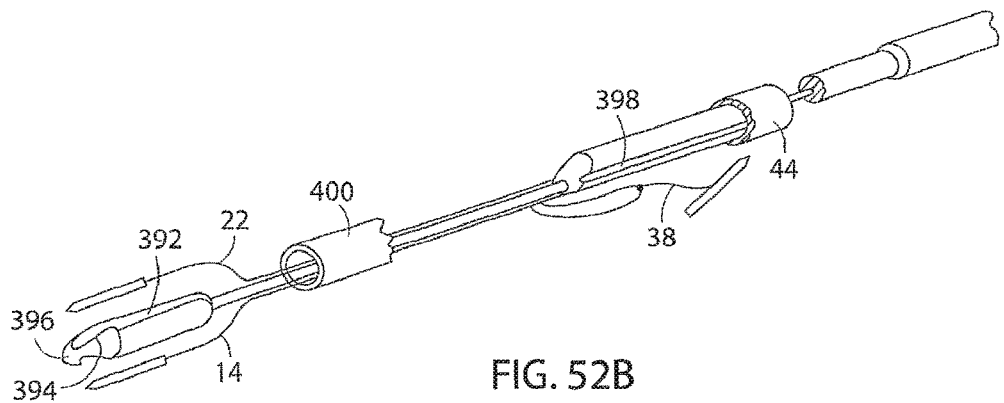

FIGS. 52A and 52B show a further embodiment of an insertion device 390. The insertion device 390 has the configuration of an elongate narrow rod with a pair of opposed grooves 392, 394 extending up one side of the rod from a distal end 396 of the rod. A third groove 398 is formed in a side of the rod toward a proximal end of the rod. The third groove 398 is positioned between the opposed pair of grooves 392, 394. According to the method of using the insertion device 390, the first cord segment 14 and second cord segment 22 of the apparatus 12 are positioned in the opposed pair of grooves 392, 394 that extend from the insertion device distal end 396. The additional cord segment 38 of the apparatus 12 is positioned in the third groove 398 in the side of the rod. With the cords of the apparatus held in these grooves, the insertion device 390 is then inserted through a cannula 44 to insert the apparatus 12 into the abdominal cavity.

Figure 53:
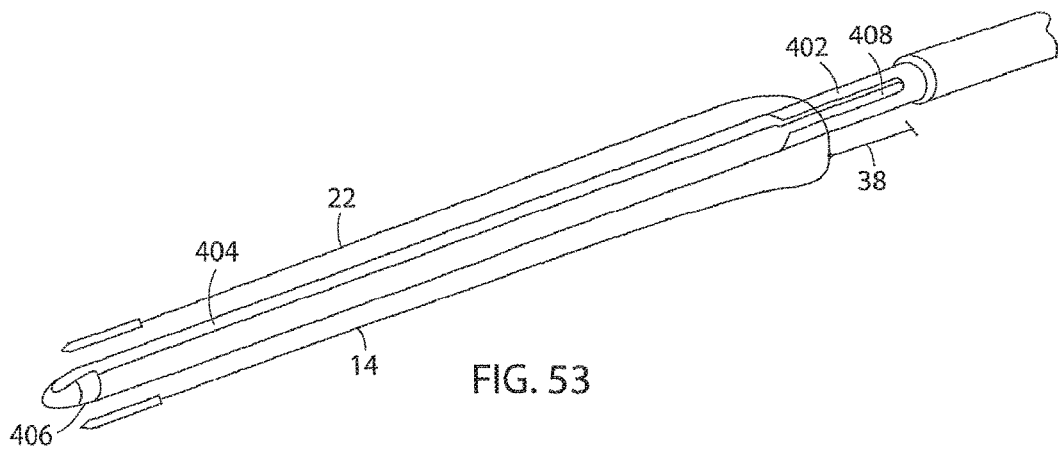
FIG. 53 represents embodiments of the apparatus and an insertion device and a method of mounting the apparatus on the insertion device.

FIG. 53 shows a representation of a further embodiment of the insertion device 402 that is similar in construction to the previously-described embodiment of the insertion device 390. The insertion device 402 of FIG. 53 is also comprised of a pair of opposed grooves 404, 406 that receive the first 14 and second 22 cord segments of the apparatus 12, and a third groove 408 that receives the additional cord segment 38 of the apparatus.

Figure 54:
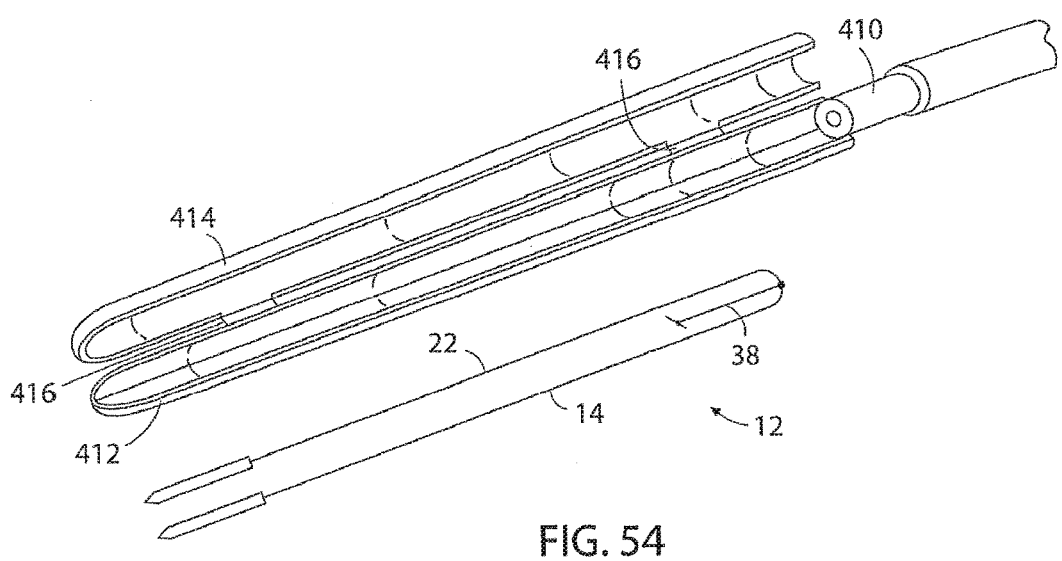
FIG. 54 represents embodiments of the apparatus and an insertion device and a method of mounting the apparatus in the insertion device.

FIG. 54 shows a still further embodiment of an insertion device 410. The insertion device 410 has a rod-shaped length with a hollow distal end. The rod distal end is comprised of a first half 412 and a second half 414 that are connected together by a living hinge assembly 416. According to the method of using the insertion device 410 of FIG. 54, the apparatus 12 is positioned in the interior of the first half 412 with the first cord segment 14 and second cord segment 22 extending parallel to each other, and the third cord segment 38 folded over the first cord segment 14 and second cord segment 22. The second half 414 of the insertion device is then folded over the hinge assembly 416 and snapped closed to prepare the insertion device 410 for insertion of the apparatus 12.

Figure 55A:
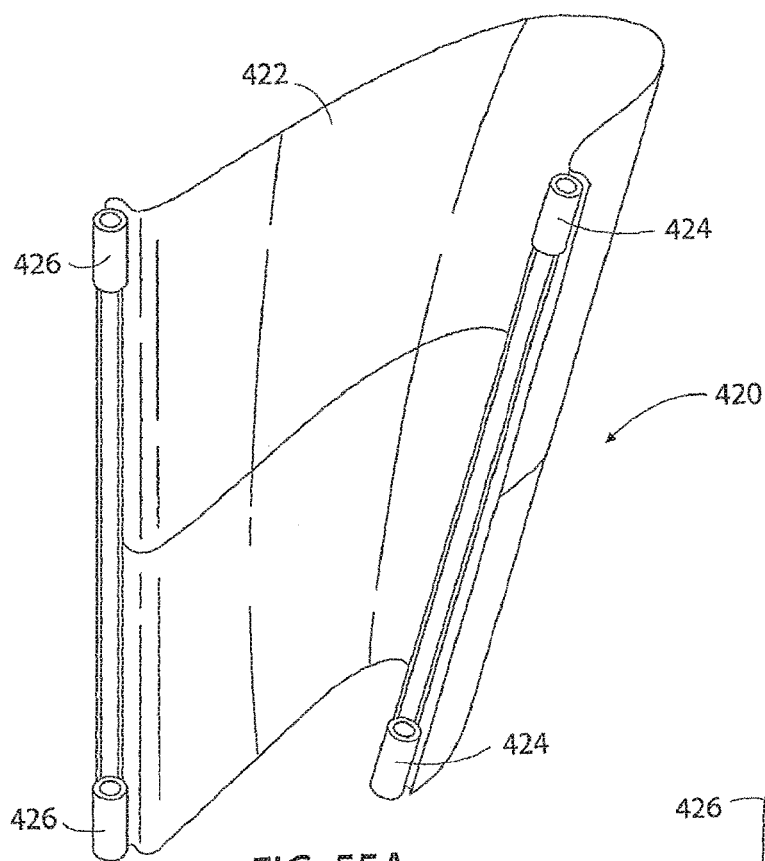
FIGS. 55A-55C represent an embodiment of the apparatus and a method of using the apparatus.
Figure 55B:
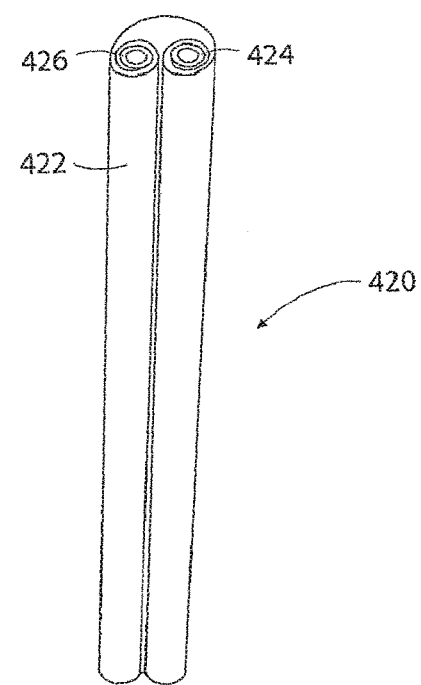
Figure 55C:
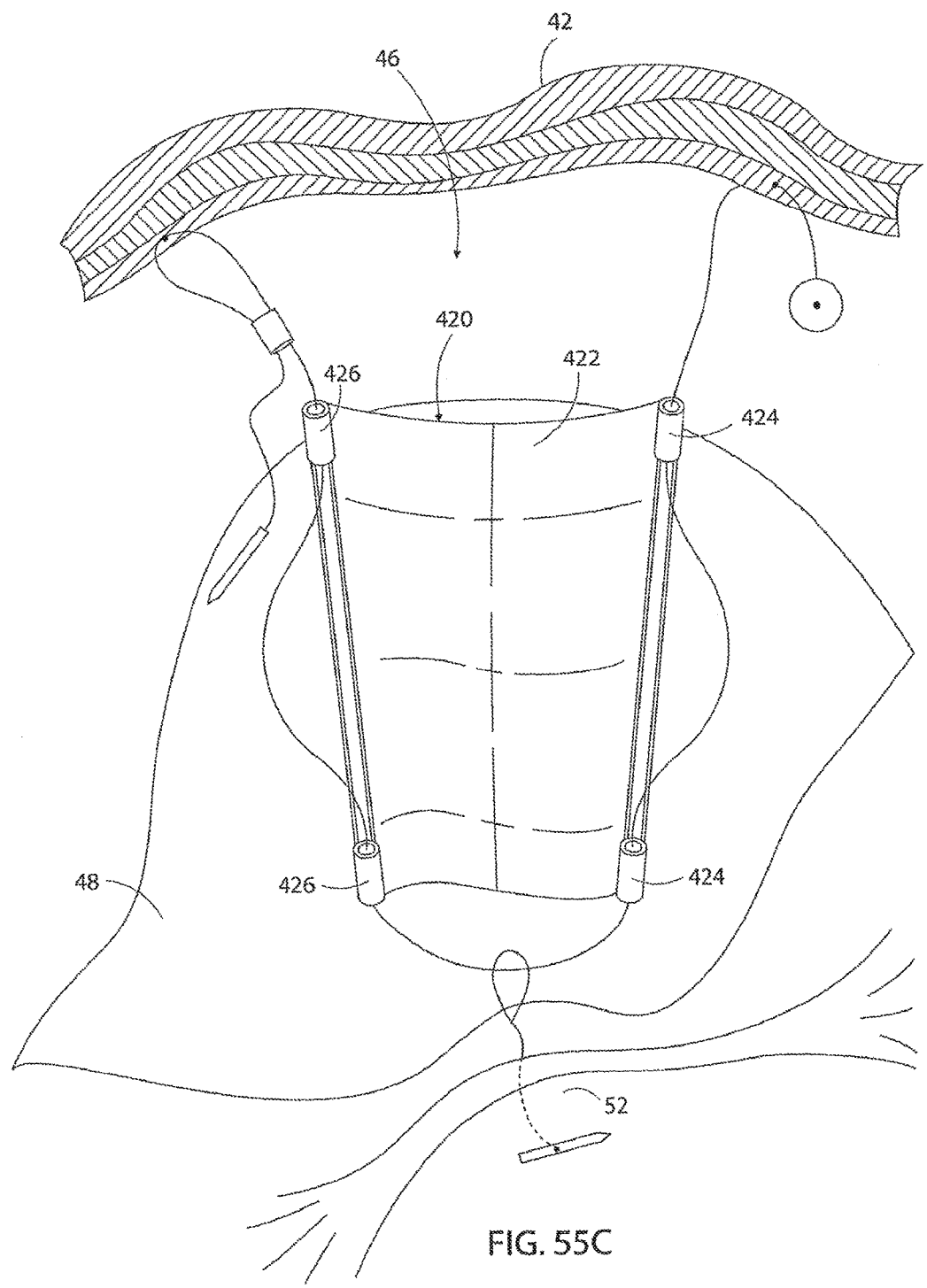

FIGS. 55A-55C show a mesh apparatus 420 that is designed to be used as a part of the apparatus of the invention. The mesh apparatus 420 is basically comprised of a generally rectangular or trapezoidal-shaped panel of surgical mesh 422 with a pair of axially aligned tubes 424 at one side and a pair of axially aligned tubes 426 at the opposite side. As shown in FIG. 55B, the mesh apparatus 420 can be rolled up around the pairs of tubes 424, 426 to reduce the size of the apparatus for insertion through a cannula and into the abdominal cavity. FIG. 55C shows the mesh apparatus 420 positioned in the abdominal cavity 46 and held in place against the first internal organ 48 by one of the previously-described embodiments of the apparatus. It should be understood that any of the previously described embodiments of the apparatus may be employed according to the method of the invention to hold the surgical mesh 420 in its position as shown in FIG. 55C.

FIGS. 56A-56C, 57A-57C, 58A-58C and 59A-59C show an embodiment of the apparatus of the invention 500 that employs a surgical tissue connector with a releasable one-way cord lock. The apparatus 500 is basically designed to be attached between body tissue (or the first internal organ) and the abdomen wall with a cord of the apparatus extending across the first internal organ as in previously described embodiments, but also includes a feature for shortening the portion of the cord extending across the first internal organ to thereby cause the portion of the cord to move the first internal organ away from the second internal organ and to hold the first internal organ in the displaced position. Thus, the apparatus 500 enables the use of only one cord to move the first internal organ to a position away from the second internal organ and then hold the first internal organ at the position.

The apparatus 500 is comprised of a base 502 having a tubular configuration. More specifically the base 502 is formed as a cylindrical housing wall having a hollow interior bore extending entirely through the length of the base housing. A center axis 506 of the interior bore defines mutually perpendicular axially and radial directions relative to the base. The base cylindrical housing 502 has axially opposite first 508 and second 510 ends.

A first rod 512 and a second rod 514 are secured to the base. As shown in the drawing figures, the first rod 512 extends radially across the base interior bore adjacent the base second end 508. Opposite ends of the first rod 512 are secured to the base cylindrical housing 502. The second rod 514 extends radially across the base interior bore adjacent the base second end 510. Opposite ends of the second rod are secured to the base cylindrical housing 502.

A first tissue connector 516 extends from the base 502 at the base first end 508. In the example shown in the drawings, the tissue connector 516 has a hook 518 formed at one end and a ring 520 formed at the opposite end. The first rod 512 extends through the ring 520 and thereby connects the tissue connector 516 to the base 502. The hook 518 is employed in connecting the apparatus 500 to body tissue. The tissue connector shown in the drawing figures is only one example of a known type of tissue connector that could be employed with the apparatus 500. Any other type of known tissue connector could replace the tissue connector 516 shown in the drawing figures. Additionally, the first tissue connector could be an integral extension of the base.

A flexible cord 522 having a length with opposite first 524 and second 526 ends is attached to the base 502 at the base second end 510. An intermediate portion 528 of the cord is wrapped around the second rod 514 thereby attaching the cord 522 to the base 502. A first portion or first percentage 530 of the cord length extends from the intermediate portion 528 and from the base second end 510 to the cord first end 524. A second portion or second percentage 532 of the cord length extends from the intermediate portion 528 and from the base second end 510 to the cord second end 526.

The cord intermediate portion 528 is wrapped around the second rod 514 by being tied in a Munter hitch or Italian hitch knot 534 around the second rod 514. In FIG. 56C the Munter hitch knot 534 is shown on a first radial side of the second rod 514. When the knot 534 is maintained in this position, the first cord portion 530 can be pulled from the knot 534 increasing the length of the cord first portion 530 (or increasing the first percentage of the overall cord length) while decreasing the length of the cord second portion 532 (or decreasing the second percentage of the overall cord length). The cord second portion 532 is braked by the knot 534 with the knot in the first position shown in FIG. 56C and the cord second portion cannot be pulled from the knot to increase its length. In FIG. 57C the Munter hitch knot 534 is shown positioned on a second radial side of the second rod 514, which is on an opposite side of the second rod 514 from the first radial side. When the knot 534 is maintained in this position, the second cord position 532 can be pulled from the knot increasing the length of the cord second portion 532 (or increasing the second percentage of the cord overall length) while decreasing the length of the cord first portion 530 (or decreasing the first percentage of the cord overall length). The cord first portion 530 is braked by the knot 534 with the knot in the second position shown in FIG. 57C and the cord first portion cannot be pulled from the knot to increase its length. The Munter hitch knot 534 is a continuously sliding knot. When the knot 534 is free to move between its first position on the first radial side of the second rod 514 shown in FIG. 56C and its second position on the second radial side of the second rod 514 shown in FIG. 57C, pulling on the cord first portion 530 will cause the knot 534 to move to the first radial side of the rod 512 shown in FIG. 56C. Further pulling on the cord first portion 530 will cause the length of the cord first portion to increase, while the length of the cord second portion 532 decreases. The cord intermediate portion 528 wrapped around the second rod 514 in the Munter hitch knot 534 is continuously wrapped around the rod as the cord first portion is pulled. Pulling on the cord second portion 532 will cause the Munter hitch knot 534 to move across the second rod 514 to the second radial side of the rod as shown in FIG. 57C. Continuing to pull on the cord second portion 532 will cause the length of the cord second portion 532 to increase while the length of the cord first portion decreases. The cord intermediate portion 528 wrapped around the second rod 514 in the Munter hitch knot 534 is continuously wrapped around the second rod 514 as the cord second portion 532 is pulled.

A second tissue connector 540 is provided on the cord second end 526. The second tissue connector 540 can be any known type of tissue connector used to attach to body tissue and is therefore shown only schematically in the drawing figures. A percentage of the cord length (the second percentage) extends between the first tissue connector and the second tissue connector. The percentage of the cord length extending between the first and second tissue connectors is intra-abdominally adjustable to increase the percentage of the cord length and to decrease the percentage of the cord length.

The apparatus 500 also includes a releasable one-way cord lock 542. The lock 542 has a cylindrical exterior surface and engages in sliding engagement with the interior surface of the base cylindrical housing 502. The lock 542 moves in axially reciprocating movements through the base interior bore between a first position of the lock shown in FIG. 56C and a second position of the lock shown in FIG. 57C. A half cylinder protrusion 544 is formed on the end of the lock adjacent the Munter hitch knot 534. As seen in the drawing Figures, the protrusion 544 is positioned on the second radial side of the second rod 514. Axial slots 546 are formed in the opposite sides of the base cylindrical housing 502 and a pin 548 extends radially through the lock 542 with opposite ends of the pin engaging in sliding engagement in the axial slots 546 of the base 502. The ends of the pin 548 extending into the axial slots 546 allow the lock 542 to axially reciprocate through the interior bore of the base but prevent the lock 532 from rotating around the interior bore of the base. This maintains the lock protrusion 544 on the second radial side of the second rod 514.

An actuator 550 is mounted on the base 502 and is operatively connected to the reversible one-way cord lock 542. The actuator 550 is formed as a cylindrical sleeve that surrounds the base cylindrical housing 502. The opposite ends of the lock pin 548 project beyond the axial slots 546 in the base cylindrical housing 502 and are secured in opposite sides of the actuator 550. This operatively connects the actuator with the lock 542. The actuator 550 is mounted on the cylindrical housing of the base 502 for axially reciprocating movements between first and second positions of the actuator relative to the base. Moving the actuator 550 to its first position relative to the base 502 moves the one-way cord lock 542 to its first position relative to the base shown in FIG. 56C. Moving the actuator 550 to its second position relative to the base 502 moves the cord lock 542 to its second position relative to the base shown in FIG. 58C.

A biasing device urges the one-way cord lock 542 to its first position shown in FIG. 56C. In the embodiment of the apparatus shown in the drawing figures the biasing device 552 is a coil spring. As shown in FIG. 56C, with the knot 534 positioned on the first radial side of the second rod 514, the spring 552 biases the lock 542 toward the knot 534 until the lock protrusion 544 engages against the cord intermediate portion 528 adjacent the knot 534. In this position of the protrusion 544 the protrusion prevents the knot 534 from moving around the second rod 514 to the second radial side of the rod. With the knot 534 maintained on the first radial side of the second rod 514 by the lock protrusion 534, exerting a pulling force on the cord first portion 530 will increase the length of the cord first portion while decreasing the length of the cord second portion 532. With the knot 534 maintained on the first radial side of the second rod 514 by the lock protrusion 544, exerting a pulling force on the cord second portion 532 will not result in increasing the length of the cord second portion 532 and decreasing the length of the cord first portion 530. The friction of the knot 534 held in the position shown in FIG. 56C will resist the cord second portion 532 from being pulled from the base second end 510.

With the actuator 550 being moved to its second position and in turn the one-way cord lock 542 being moved to its second position shown in FIG. 57C, the knot 534 is free to move between the first radial side of the second rod 514 as shown in FIG. 56C and the second radial side of the second rod 514 as shown in FIG. 57C. With the lock protrusion 544 moved away from the knot, exerting a pulling force on the cord second portion 532 will cause the knot 534 to move from its position on the first radial side of the second rod 514 shown in FIG. 56C to its position on the second radial side of the second rod 514 shown in FIG. 57C. In this position of the knot, the pulling force exerted on the cord second portion 532 will result in the length of the cord second portion 532 increasing while the length of the cord first portion 530 decreases. When the actuator 550 is released and the spring 552 biases the one-way cord lock 542 back toward its first position, exerting a pulling force on the cord first portion 530 will cause the knot 532 to move from its position on the second radial side of the second rod 514 shown in FIG. 57C to its position on the first radial side of the second rod 514 shown in FIG. 56C. The biasing force of the spring 552 is not sufficient to hold the knot 534 on the second radial side of the second rod 514. With the knot 534 positioned on the first radial side of the second rod 514 as shown in FIG. 56C, again exerting a pulling force on the cord first portion 530 will result in increasing the length of the cord first portion while decreasing the length of the cord second portion 532. Again, the friction of the knot 534 held at the position on the first radial side of the second rod 514 shown in FIG. 56C will resist the cord second portion 532 from being pulled from the base housing second end 510.

FIGS. 60A-60C, 61A-61C, 62A-62C and 63A-63C show a variant embodiment of the tissue connector apparatus with a releasable one-way cord lock just described. In this further embodiment of the apparatus 554, many of the component parts of the apparatus 554 are the same as those of the previously described apparatus 500. Therefore, these component parts will not be described again. The reference numbers used to identify the component parts in this further embodiment are the same as those used in identifying the component parts of the previous embodiment of the apparatus 500. These component parts include the base cylindrical wall housing 502, the first rod 512, the second rod 514, the first tissue connector 516, the second tissue connector 540, the cord 552, the Munter hitch knot 534 and the biasing device or coil spring 552.

The construction of the further embodiment of the apparatus 554 differs from that of the previous embodiment basically in the construction of the releasable one-way cord lock 556. The lock 556 has a lock protrusion 544 that functions in the same manner as the previous embodiment. However, the cylindrical configuration of the lock 556 extends beyond the base cylindrical housing first end 508 to an annual flange or rim 558 on an opposite end of the lock from the protrusion 554. This rim 558 functions as the actuator of the lock 556. The rim 558 surrounds a hollow center bore 560. The bore extends from the rim down into the lock 556 and ends short of the lock protrusion 544. A pair of axially extending slots 562 are formed in the opposite sides of the lock 556 and communicate the interior bore 560 with the exterior of the lock 556. The first rod 508 extends through the pair of slots 562. The engagement of the first rod 512 through the slots 562 enables the lock 556 to reciprocate between its first and second positions relative to the base 502, but prevents the lock 556 from rotating relative to the base. This maintains the protrusion 544 on the second radial side of the second rod 514.

The first tissue connector 516 is connected to the first rod 512 just as in the previous embodiment. The first tissue connector 515 extends from the first rod 512 to the hook 518 of the connector.

The biasing device in the form of the coil spring 522 is positioned in the interior bore 560 of the lock 556. The spring 552 is positioned between the first tissue connector ring 520 and the lock 556 and exerts a biasing force on the lock pushing the lock toward its first position relative to the base 502.

The releasable one-way cord lock 556 of the apparatus 554 functions in the same manner as the previously described apparatus in maintaining the Munter hitch knot 534 on the first radial side of the second rod 514 when the lock is in its first position relative to the base, and allowing the knot 534 to move to the second side of the second rod 514 when the lock is moved to its second position on the base.

Figure 64:
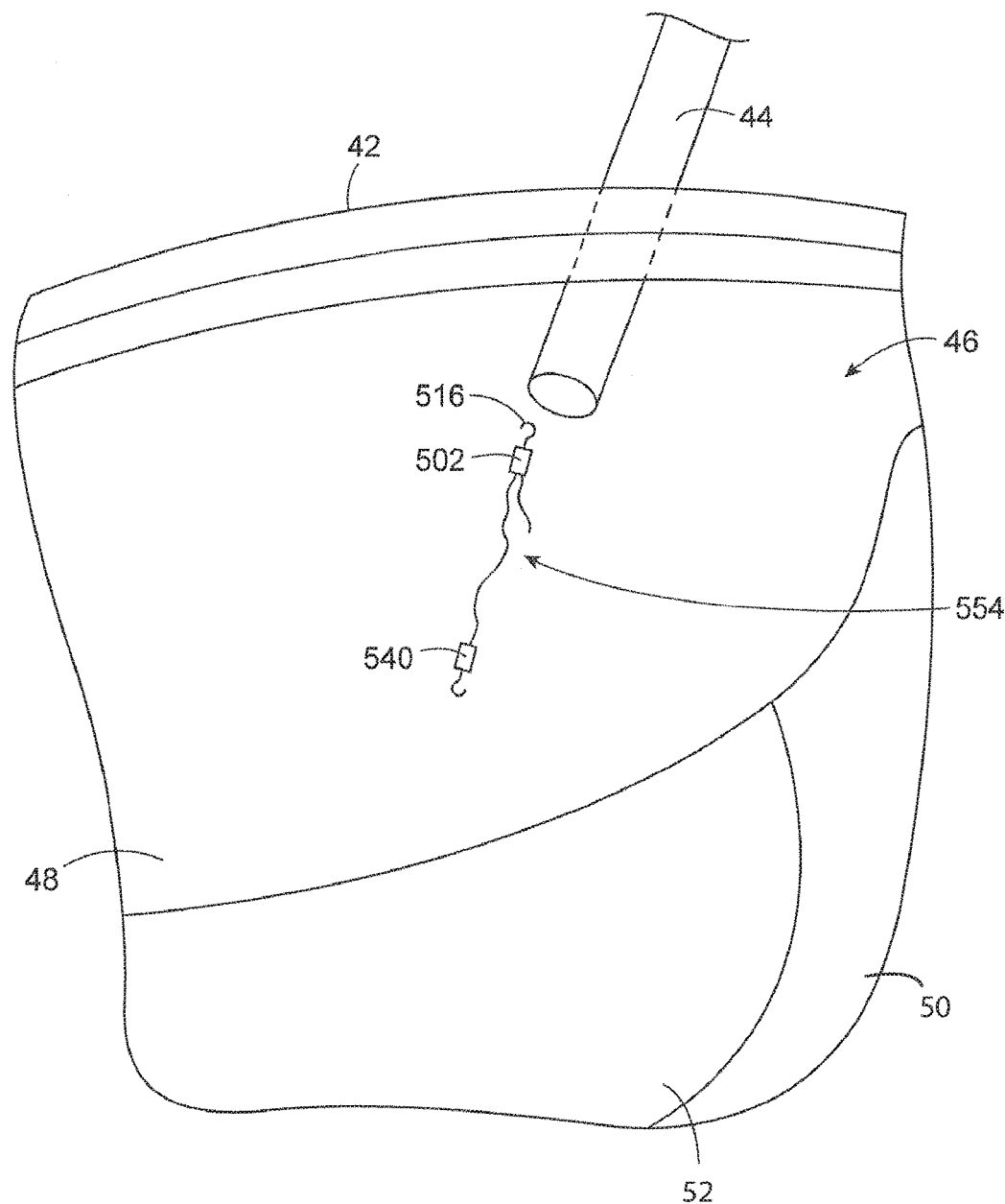
FIGS. 64-67 are representations of a method of using either of the embodiments of the surgical tissue connector apparatus shown in FIGS. 56A-56C or 60A-60C.

Both embodiments of the apparatus have the same method of use. Basically, a portion of the cord is attached to body tissue on an opposite side of the abdominal cavity from the abdominal wall, an additional portion of the cord is attached to the abdominal wall positioning a length or percentage of the cord across the first internal organ, and then the length or percentage of the cord extending across the first organ is decreased thereby causing the decreasing percentage of the cord length to engage across and move the first internal organ away from the second internal organ. This is illustrated schematically in FIG. 64. As in the previously described embodiments, the apparatus 554 is first manually passed through the abdomen wall 42, for example through an incision or a cannula 44 in the abdomen wall and is positioned in the abdominal cavity 46 in the area of the first 48 and second 50 internal organs. In the example shown, the first internal organ 48 represented is the human liver and the second internal organ 50 represented is the human stomach.

Figure 65:
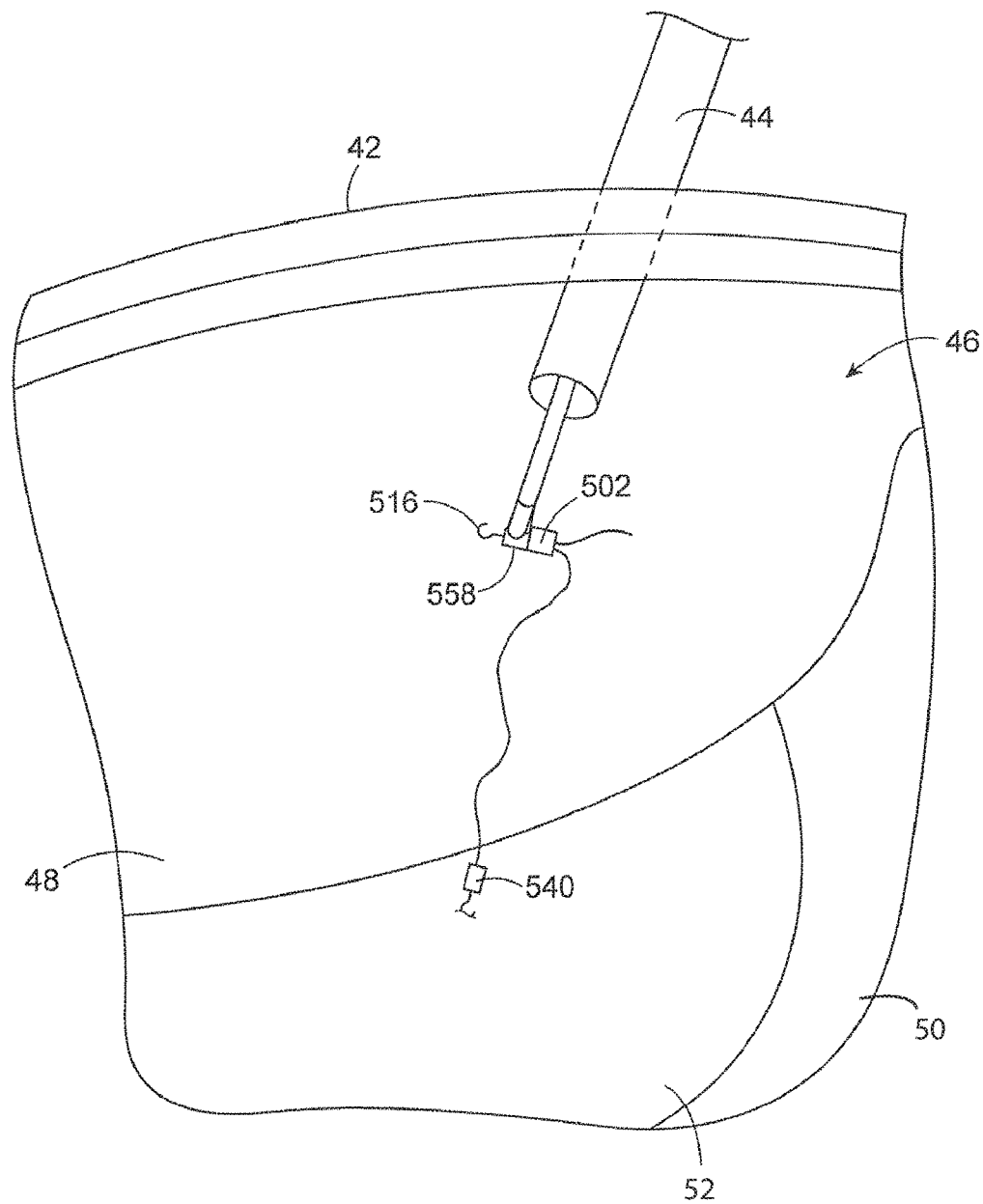
Figure 66:
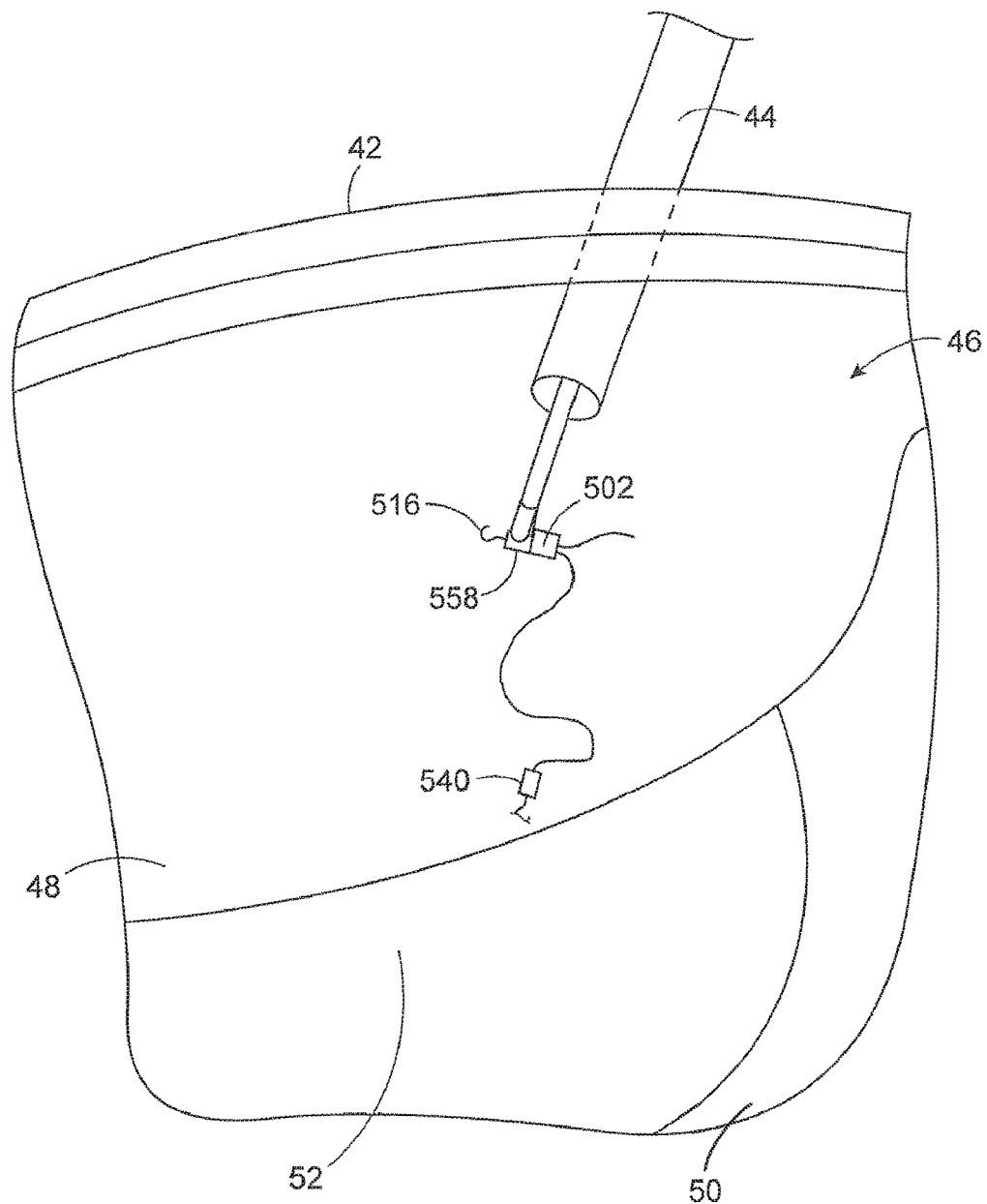

The second tissue connector 540 of the apparatus 554 is then manually connected to tissue 52 adjacent to the first internal organ 48 and between the first 48 and second 50 internal organs. In the example shown in FIG. 65, the tissue 52 is the crus of the diaphragm. Alternatively, the second tissue connector 540 could be connected to the tissue of the first internal organ 48 itself, as shown in FIG. 66. The apparatus 554 is then grasped by its actuator 558 and moved toward the abdominal wall 42. This movement causes the actuator 558 and its associated releasable one-way cord lock to move to their second positions. The movement of the lock allows the knot to move to the second side of the second rod 514 when the cord second portion 532 is pulled in tension. The movement of the knot to the second side of the second rod 514 allows the cord second portion 532 to be pulled from the base second end 510 and increase in length (or increase in percentage) as the apparatus 554 is moved toward the abdominal wall 42. When at the abdominal wall, the tissue connector 516 of the apparatus 500/554 is then connected to the inner abdominal wall 42. This positions the cord second portion 532 extending from the second tissue connector 540 across the first internal organ 48 to the first tissue connector 516 attached to the abdominal wall 42.

The actuator 558 of the apparatus 554 is then released. This results in the spring of the apparatus moving the releasable one-way cord lock to its first position relative to the base 502.

The cord first portion 530 is then grasped and pulled from the base second end 510. This causes the knot to move to the first side of the second rod 514 and causes the length of the cord first portion 530 to increase (or increase in percentage) while decreasing the length of the cord second portion 532 (or decreasing the percentage of the cord second portion). The decreasing length of the cord second portion 532 is pulled tight across the first internal organ 48.

Figure 67:
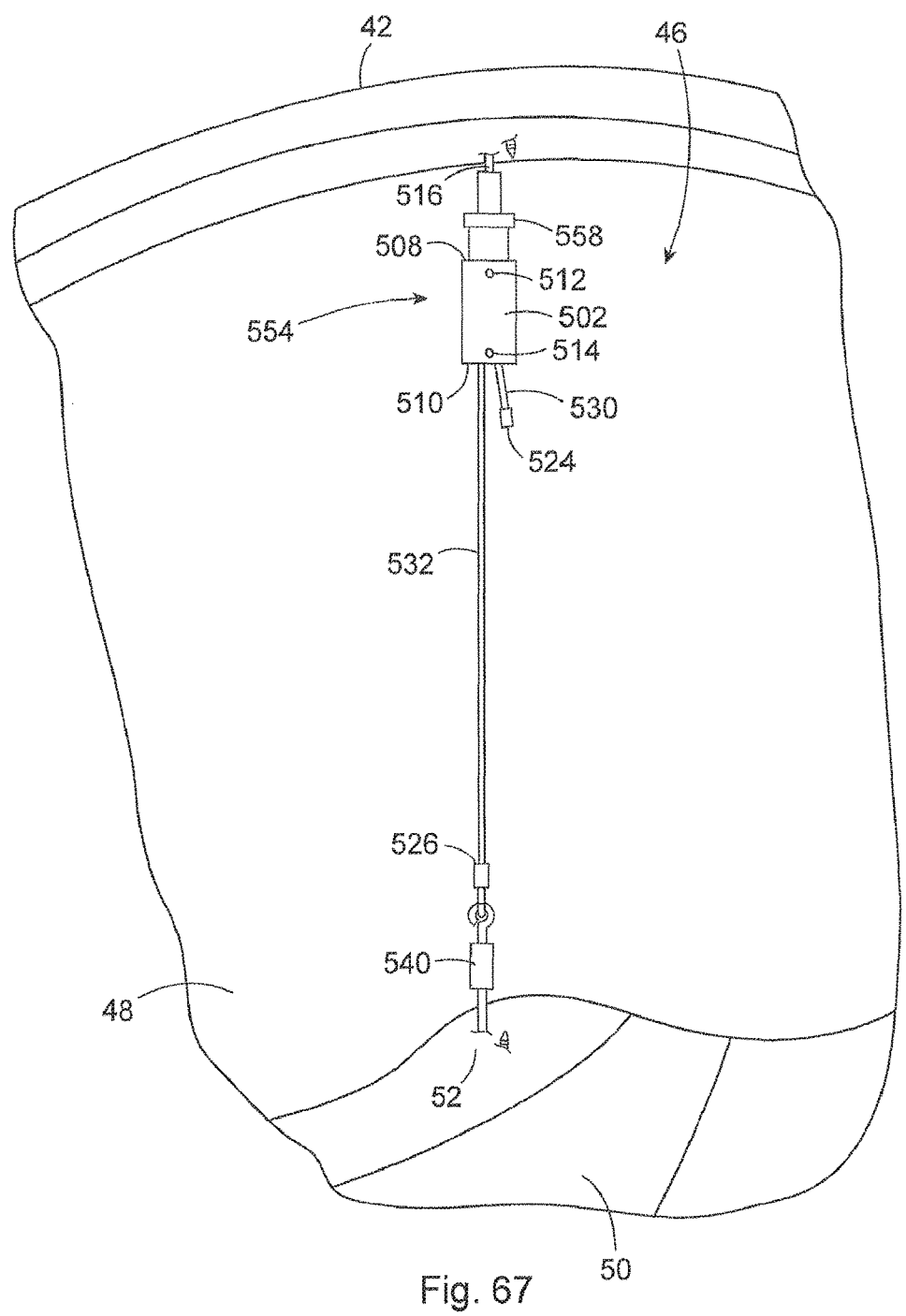

Continuing the pulling force on the cord first portion 530 continues to decrease the length of the cord second portion 532 causing the cord second portion to move the first internal organ 48 toward the position away from the second internal organ 50. When the first internal organ 58 is in the desired position, the grasping and pulling force on the court first portion 530 is released. With the pulling force on the cord first portion 530 having moved the knot to the first radial side of the second rod 514, the lock protrusion prevents the knot from moving back to the second radial side of the second rod 514. With the knot maintained on the first radial side of the second rod 514, the length of the cord second portion cannot be increased. Therefore, the cord second portion 532 holds the first internal organ 48 in its position away from the second internal organ 50 as shown in FIG. 67.

When it is desired to remove the apparatus 554 from the abdominal cavity the actuator 558 is again grasped and moved toward its second position on the base 502. This cases the lock to move to its second position and moves the lock protrusion away from the knot. This again allows the knot to move to the second side of the second rod 514 and allows the cord second portion 532 to be pulled from the base second end 510. This in turn allows the first internal organ 48 to return to its original position relative to the second internal organ 50. The increased length of the cord second portion 532 enables the first tissue connector 516 and second tissue connector 540 to be removed from their connections to the body tissue.

Figure 68:
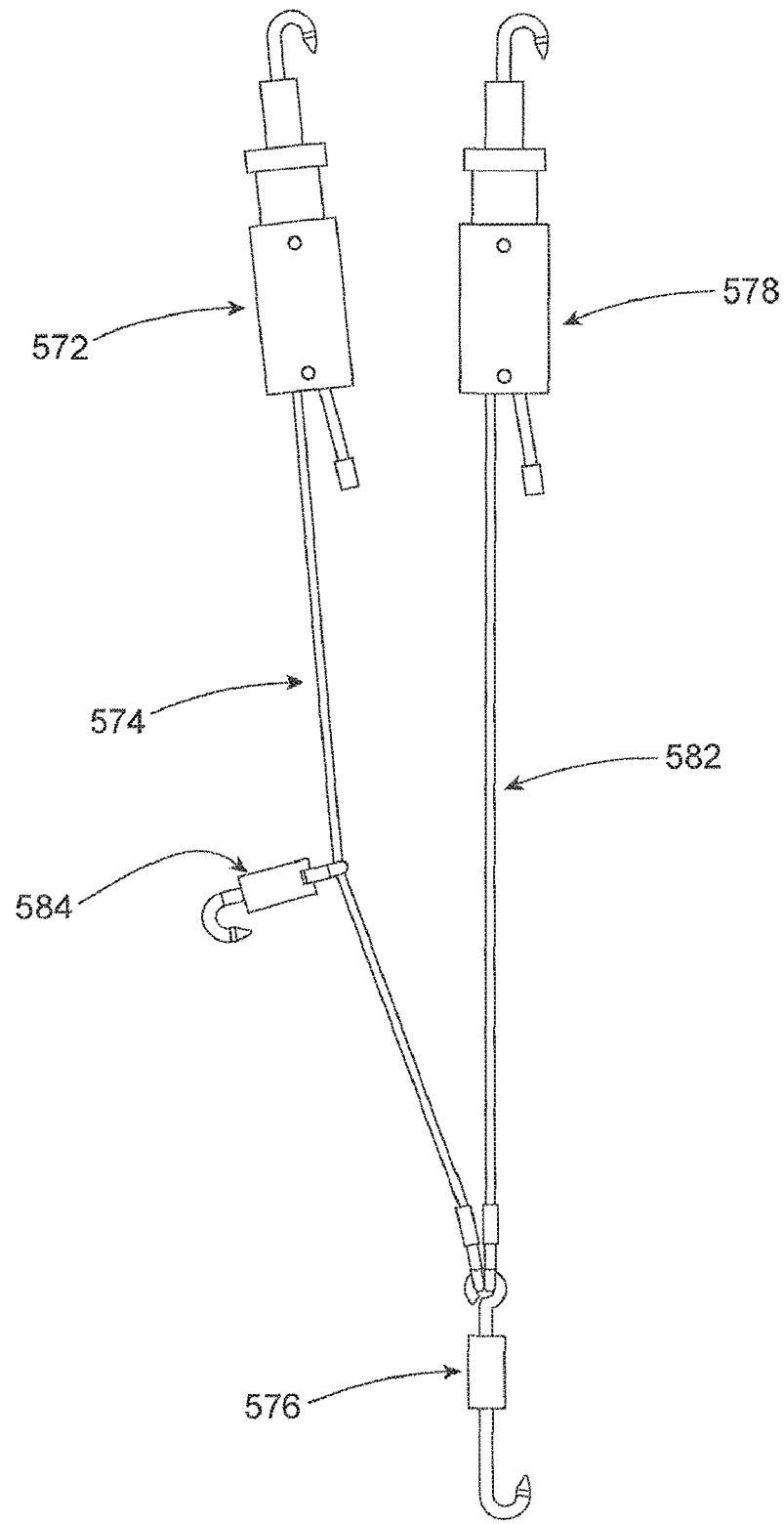
FIG. 68 is a view of a still further embodiment of the apparatus comprising two cord lengths and four tissue connectors.

FIG. 68 shows a still further embodiment of the apparatus of the invention. The apparatus in FIG. 68 comprises a first tissue connector 572, a cord 574 and a second tissue connector 576 that are the same as those of the previously discussed embodiment of the apparatus. In addition, the apparatus of FIG. 68 includes a third tissue connector 578 that is the same as the first tissue connector 572, and a second length of cord 582 that is the same as the first length of cord 574. The apparatus of FIG. 68 also includes a fourth tissue connector 584 that is mounted to the portion of the cord 574 extending between the first tissue connector 572 and the second tissue connector 576 for sliding movement of the fourth tissue connector 584 along the length of cord.

The method of using the apparatus shown in FIG. 68 is similar to that of previously described embodiments. The second tissue connector 576 is connected to body tissue adjacent to the first internal organ or to the first internal organ, and then the first tissue connector 572 is moved intra-abdominally toward the abdominal wall and is connected to the abdominal wall. This causes the first cord 574 to extend across the first internal organ. The third tissue connector 578 is then moved intra-abdominally toward the abdominal wall and is connected to the abdominal wall in a position spaced from the first tissue connector 572. This causes the second cord 582 to extend across the first internal organ. Shortening first 574 and second 582 cords causes the cords to engage with and move the first internal organ upwardly and away from the second internal organ in a manner similar to that of previously described embodiments.

In addition to the above, the fourth tissue connector 584 can be used to laterally displace or move the first internal organ in a sideways direction. This is accomplished by grasping the fourth tissue connector 584 with a surgical grasper and then pushing the first internal organ to one side or the other before securing the fourth tissue connector 584 to body tissue. This results in the fourth tissue connector 584 holding the first internal organ in its sideways displaced position.

As various modifications could be made in the constructions of the apparatus and the methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

We claim:

1. A surgical tissue connector system for moving a first internal body tissue to a position away from a second internal body tissue and then holding the first internal body tissue in the position away from the second internal body tissue, said tissue connector system comprising:
   a first tissue connector that is connectable to body tissue;
   a base comprising a first end secured to the first tissue connector, a second end, and a bore extending within the base;
   a rod extending through the bore of the base;
   a lock slidably disposed within the bore of the base;
   a cord extending from the base secured to said first tissue connector, said cord characterized by a first portion extending from the rod and out of the base at the second end, a second portion extending from the rod and out of the base at the second end, and an intermediate portion comprising a sliding knot wrapped around and engaging the rod;
   an actuator connected to the lock, and operable to move the lock within the bore of the base;
   wherein, in a first configuration, the knot is disposed on a first side of the bore opposite, relative to the rod, an impinging structure of the lock, and is free to slide in a first direction away from the impinging structure when the cord first portion is pulled, and the knot is prevented from sliding in a second direction toward the impinging structure when the cord second portion is pulled; and
   wherein, in a second configuration, the knot is disposed on a second side of the bore, relative to the rod, and on the same side of the bore as the impinging structure of the lock, and the knot is free to slide in a second direction away from the impinging structure when the cord second portion is pulled.

2. The system of claim 1, wherein:
   the lock is slidable within the bore between a first position and a second position, wherein, in the first position, the impinging structure of the lock engages the knot in the first configuration, such that the knot is prevented from moving from the first side of the bore to the second side of the bore to achieve the second configuration.

3. The system of claim 2, wherein:
   in the second position, the impinging structure of the lock does not engage the knot in the first configuration, such that the knot is free to move from the first side of the bore to the second side of the bore to achieve the second configuration, so that the sliding knot may be moved to the second side of the bore by pulling on the cord second portion.

4. The system of claim 2, wherein
   in the second position, the impinging structure of the lock does not engage the knot in the second configuration, such that the knot is free to move from the second side of the bore to the first side of the bore to achieve the first configuration, so that the sliding knot may be moved to the first side of the bore by pulling on the cord first portion.

5. The system of claim 2, further comprising:
a biasing spring operable to apply biasing force to the lock to bias the lock toward the first position and thereby urge the impinging structure to engage the knot.

6. The system of 5, wherein the biasing force of the biasing spring is not sufficient to hold the knot on the second side of the bore when the cord first portion is pulled in the first direction.

7. The device of 6 wherein the cord is operable, by pulling on the cord first portion, to overcome the biasing force of the biasing spring and move the knot from the second side of the bore to the first side of the bore.

8. The system of claim 2, wherein:
the lock is slidable within the bore between the first position and the second position, wherein, in the first position, the impinging structure of the lock engages the knot in the second configuration, such that the knot is prevented from moving from the second side of the bore to the first side of the bore to achieve the first configuration.

9. The system of claim 2, wherein:
the lock is slidable within the bore between the first position and the second position, wherein, in the first position, the impinging structure of the lock engages the knot in the second configuration, such that the knot is inhibited from moving from the second side of the bore to the first side of the bore to achieve the first configuration.

10. The system of claim 1, wherein:
the lock is slidable within the bore between a first position and a second position, wherein, in the first position, the impinging structure of the lock engages the knot in the second configuration, such that the knot is prevented from moving from the second side of the bore to the first side of the bore to achieve the first configuration.

11. The system of claim 1, wherein:
the lock is slidable within the bore between a first position and a second position, wherein, in the first position, the impinging structure of the lock engages the knot in the second configuration, such that the knot is inhibited from moving from the second side of the bore to the first side of the bore to achieve the first configuration.

12. The system of claim 1 further comprising:
a second tissue connector that is connectable to body tissue, said second tissue connector disposed on the second cord portion.

13. A surgical tissue connector system for moving a first internal body tissue to a position away from a second internal body tissue and then holding the first internal body tissue in the position away from the second internal body tissue, said tissue connector system comprising:
a first tissue connector that is connectable to body tissue;
a base comprising a first end secured to the first tissue connector, a second end, and a bore extending within the base;
a rod extending through the bore of the base;
a lock slidably disposed within the bore of the base, between a first position and a second position;
a cord extending from the base secured to said first tissue connector, said cord characterized by a first portion extending from the rod and out of the base at the second end, a second portion extending from the rod and out of the base at the second end, and an intermediate portion comprising a sliding knot wrapped around and engaging the rod;
an actuator connected to the lock, and operable to move the lock within the bore of the base;
wherein, in a first configuration, with the lock in the first position, the knot is disposed on a first side of the bore opposite, relative to the rod, an impinging structure of the lock, and the impinging structure engages the knot, and the knot is free to slide in a first direction away from the impinging structure when the cord first portion is pulled, and the knot is prevented from sliding in a second direction toward the impinging structure when the cord second portion is pulled;
wherein, in a second configuration, with the lock in the first position, the knot is disposed on a second side of the bore, relative to the rod, and on the same side of the bore as the impinging structure of the lock, the impinging structure engages the knot, and the knot is free to slide in a second direction away from the impinging structure when the cord second portion is pulled, and the knot is inhibited from sliding in a first-direction toward the first side of the bore when the cord first portion is pulled; and
wherein, in a third configuration, with the lock in the second position, the impinging structure of the lock does not impinge on the knot, and the knot is free to slide in a first direction toward the first side of the bore when the cord first portion is pulled, and the knot is free to slide in a second direction toward the second side of the bore when the cord second portion is pulled.

14. The system of claim 13, further comprising:
a biasing spring operable to apply biasing force to the lock to bias the lock toward the first position and thereby urge the impinging structure to engage the knot.

15. The system of claim 14, wherein the biasing force of the biasing spring is not sufficient to hold the knot on the second side of the bore, in the second configuration, when the cord first portion is pulled in the first direction.

16. The device of claim 15 wherein, in the second configuration, the cord is operable, by pulling on the cord first portion, to overcome the biasing force of the biasing spring and move the knot from the second side of the bore to the first side of the bore.

17. The system of claim 13 further comprising:
a second tissue connector that is connectable to body tissue, said second tissue connector disposed on the second cord portion.

* * * * *